(12) United States Patent
Rhodes et al.

(10) Patent No.: US 8,509,871 B2
(45) Date of Patent: Aug. 13, 2013

(54) SENSOR HEAD FOR USE WITH IMPLANTABLE DEVICES

(75) Inventors: Rathbun K. Rhodes, Madison, WI (US); Mark A. Tapsak, Orangeville, PA (US); James H. Brauker, Cement City, MI (US); Mark C. Shults, Madison, WI (US)

(73) Assignee: DexCom, Inc., San Diego, CA (US)

( * ) Notice: Subject to any disclaimer, the term of this patent is extended or adjusted under 35 U.S.C. 154(b) by 1299 days.

(21) Appl. No.: 12/260,017

(22) Filed: Oct. 28, 2008

(65) Prior Publication Data

US 2009/0045055 A1 Feb. 19, 2009

Related U.S. Application Data

(60) Division of application No. 11/021,162, filed on Dec. 22, 2004, now Pat. No. 7,471,972, which is a continuation of application No. 09/916,711, filed on Jul. 27, 2001, now abandoned.

(51) Int. Cl.
*A61B 5/05* (2006.01)
(52) U.S. Cl.
USPC ............................ 600/345; 600/347; 600/365
(58) Field of Classification Search
USPC .......................................... 600/345–347, 365
See application file for complete search history.

(56) References Cited

U.S. PATENT DOCUMENTS

| | | | |
|---|---|---|---|
| 1,564,641 A | 12/1925 | St. James | |
| 2,402,306 A | 6/1946 | Turkel | |
| 2,719,797 A | 10/1955 | Rosenblatt et al. | |
| 2,830,020 A | 4/1958 | Christmann et al. | |
| 3,210,578 A | 10/1965 | Sherer | |
| 3,220,960 A | 11/1965 | Lim et al. | |
| 3,381,371 A | 5/1968 | Russell | |
| 3,562,352 A | 2/1971 | Nyilas | |

(Continued)

FOREIGN PATENT DOCUMENTS

| | | |
|---|---|---|
| EP | 0 098 592 | 1/1984 |
| EP | 0 107 634 | 5/1984 |

(Continued)

OTHER PUBLICATIONS

US 7,530,950, 05/2009, Brister et al. (withdrawn).

(Continued)

*Primary Examiner* — Patricia Mallari
*Assistant Examiner* — Michael D'Angelo
(74) *Attorney, Agent, or Firm* — Knobbe Martens Olson & Bear, LLP

(57) ABSTRACT

The present invention provides a sensor head for use in an implantable device that measures the concentration of an analyte in a biological fluid which includes: a non-conductive body; a working electrode, a reference electrode and a counter electrode, wherein the electrodes pass through the non-conductive body forming an electrochemically reactive surface at one location on the body and forming an electronic connection at another location on the body, further wherein the electrochemically reactive surface of the counter electrode is greater than the surface area of the working electrode; and a multi-region membrane affixed to the nonconductive body and covering the working electrode, reference electrode and counter electrode. In addition, the present invention provides an implantable device including at least one of the sensor heads of the invention and methods of monitoring glucose levels in a host utilizing the implantable device of the invention.

15 Claims, 15 Drawing Sheets

(56) References Cited

U.S. PATENT DOCUMENTS

| | | | |
|---|---|---|---|
| 3,607,329 A | 9/1971 | Manjikian | |
| 3,652,475 A | 3/1972 | Wada et al. | |
| 3,746,588 A | 7/1973 | Brown, Jr. | |
| 3,775,182 A | 11/1973 | Patton et al. | |
| 3,791,871 A | 2/1974 | Rowley | |
| 3,826,244 A | 7/1974 | Salcman et al. | |
| 3,838,033 A | 9/1974 | Mindt et al. | |
| 3,898,984 A | 8/1975 | Mandel et al. | |
| 3,929,971 A | 12/1975 | Roy | |
| 3,933,593 A | 1/1976 | Sternberg | |
| 3,943,918 A | 3/1976 | Lewis | |
| 3,957,613 A | 5/1976 | Macur | |
| 3,964,974 A | 6/1976 | Banauch et al. | |
| 3,966,580 A | 6/1976 | Janata et al. | |
| 3,982,530 A | 9/1976 | Storch | |
| 4,024,312 A | 5/1977 | Korpman | |
| 4,037,563 A | 7/1977 | Pflueger et al. | |
| 4,040,908 A | 8/1977 | Clark, Jr. | |
| 4,052,754 A | 10/1977 | Homsy | |
| 4,067,322 A | 1/1978 | Johnson | |
| 4,073,713 A | 2/1978 | Newman | |
| 4,076,656 A | 2/1978 | White et al. | |
| 4,136,250 A | 1/1979 | Mueller et al. | |
| 4,172,770 A | 10/1979 | Semersky et al. | |
| 4,197,840 A | 4/1980 | Beck et al. | |
| 4,215,703 A | 8/1980 | Willson | |
| 4,240,889 A | 12/1980 | Yoda et al. | |
| 4,253,469 A | 3/1981 | Aslan | |
| 4,255,500 A | 3/1981 | Hooke | |
| 4,256,561 A | 3/1981 | Schindler et al. | |
| 4,259,540 A | 3/1981 | Sabia | |
| 4,260,725 A | 4/1981 | Keogh et al. | |
| 4,267,145 A | 5/1981 | Wysong | |
| 4,292,423 A | 9/1981 | Kaufmann et al. | |
| 4,324,257 A | 4/1982 | Albarda et al. | |
| 4,353,888 A | 10/1982 | Sefton | |
| 4,374,013 A | 2/1983 | Enfors | |
| 4,378,016 A | 3/1983 | Loeb | |
| 4,388,166 A | 6/1983 | Suzuki et al. | |
| 4,402,694 A | 9/1983 | Ash et al. | |
| 4,403,847 A | 9/1983 | Chrestensen | |
| 4,403,984 A | 9/1983 | Ash et al. | |
| 4,415,666 A | 11/1983 | D'Orazio et al. | |
| 4,418,148 A | 11/1983 | Oberhardt | |
| 4,419,535 A | 12/1983 | O'hara | |
| 4,431,004 A | 2/1984 | Bessman et al. | |
| 4,431,507 A | 2/1984 | Nankai et al. | |
| 4,436,094 A | 3/1984 | Cerami | |
| 4,442,841 A | 4/1984 | Uehara et al. | |
| 4,453,537 A | 6/1984 | Spitzer | |
| 4,454,295 A | 6/1984 | Wittmann et al. | |
| 4,477,314 A | 10/1984 | Richter et al. | |
| 4,482,666 A | 11/1984 | Reeves | |
| 4,484,987 A | 11/1984 | Gough | |
| 4,493,714 A | 1/1985 | Ueda et al. | |
| 4,494,950 A | 1/1985 | Fischell | |
| 4,506,680 A | 3/1985 | Stokes | |
| RE31,916 E | 6/1985 | Oswin et al. | |
| 4,527,999 A | 7/1985 | Lee | |
| 4,534,355 A | 8/1985 | Potter | |
| 4,545,382 A | 10/1985 | Higgins et al. | |
| 4,554,927 A | 11/1985 | Fussell | |
| 4,571,292 A | 2/1986 | Liu et al. | |
| 4,577,642 A | 3/1986 | Stokes | |
| 4,578,215 A | 3/1986 | Bradley | |
| 4,583,976 A | 4/1986 | Ferguson | |
| 4,602,922 A | 7/1986 | Cabasso et al. | |
| 4,632,968 A | 12/1986 | Yokota et al. | |
| 4,644,046 A | 2/1987 | Yamada | |
| 4,647,643 A | 3/1987 | Zdrahala et al. | |
| 4,650,547 A | 3/1987 | Gough | |
| 4,655,880 A | 4/1987 | Liu | |
| 4,663,824 A | 5/1987 | Kenmochi | |
| 4,671,288 A * | 6/1987 | Gough | 600/347 |
| 4,672,970 A | 6/1987 | Uchida et al. | |
| 4,680,268 A | 7/1987 | Clark, Jr. | |
| 4,684,538 A | 8/1987 | Klemarczyk | |
| 4,685,463 A | 8/1987 | Williams | |
| 4,686,044 A | 8/1987 | Behnke et al. | |
| 4,686,137 A | 8/1987 | Ward, Jr. et al. | |
| 4,689,149 A | 8/1987 | Kanno et al. | |
| 4,689,309 A | 8/1987 | Jones | |
| 4,702,732 A | 10/1987 | Powers et al. | |
| 4,703,756 A | 11/1987 | Gough et al. | |
| 4,711,245 A | 12/1987 | Higgins | |
| 4,711,251 A | 12/1987 | Stokes | |
| 4,721,677 A * | 1/1988 | Clark, Jr. | 600/316 |
| 4,726,381 A | 2/1988 | Jones | |
| 4,731,726 A | 3/1988 | Allen | |
| 4,739,380 A | 4/1988 | Lauks et al. | |
| 4,750,496 A | 6/1988 | Reinhart et al. | |
| 4,753,652 A | 6/1988 | Langer et al. | |
| 4,757,022 A | 7/1988 | Shults et al. | |
| 4,759,828 A | 7/1988 | Young et al. | |
| 4,763,658 A | 8/1988 | Jones | |
| 4,776,944 A | 10/1988 | Janata et al. | |
| 4,781,733 A | 11/1988 | Babcock et al. | |
| 4,781,798 A | 11/1988 | Gough | |
| 4,786,657 A | 11/1988 | Hammar et al. | |
| 4,787,398 A | 11/1988 | Garcia et al. | |
| 4,793,555 A | 12/1988 | Lee et al. | |
| 4,795,542 A | 1/1989 | Ross et al. | |
| 4,803,243 A | 2/1989 | Fujimoto et al. | |
| 4,805,624 A | 2/1989 | Yao et al. | |
| 4,805,625 A | 2/1989 | Wyler | |
| 4,810,470 A | 3/1989 | Burkhardt et al. | |
| 4,813,424 A | 3/1989 | Wilkins | |
| 4,822,336 A | 4/1989 | DiTraglia | |
| 4,823,808 A | 4/1989 | Clegg et al. | |
| 4,832,034 A | 5/1989 | Pizziconi | |
| 4,852,573 A | 8/1989 | Kennedy | |
| 4,858,615 A | 8/1989 | Meinema | |
| 4,861,830 A | 8/1989 | Ward, Jr. | |
| 4,871,440 A | 10/1989 | Nagata et al. | |
| 4,880,883 A | 11/1989 | Grasel et al. | |
| 4,883,057 A | 11/1989 | Broderick | |
| 4,886,740 A | 12/1989 | Vadgama | |
| 4,889,744 A | 12/1989 | Quaid | |
| 4,890,620 A | 1/1990 | Gough | |
| 4,890,621 A | 1/1990 | Hakky | |
| 4,902,294 A | 2/1990 | Gosserez | |
| 4,908,208 A | 3/1990 | Lee et al. | |
| 4,909,908 A | 3/1990 | Ross et al. | |
| 4,919,141 A | 4/1990 | Zier et al. | |
| 4,927,407 A | 5/1990 | Dorman | |
| 4,935,345 A | 6/1990 | Guilbeau et al. | |
| 4,938,860 A | 7/1990 | Wogoman | |
| 4,951,657 A | 8/1990 | Pfister et al. | |
| 4,952,618 A | 8/1990 | Olsen | |
| 4,953,552 A | 9/1990 | DeMarzo | |
| 4,954,381 A | 9/1990 | Cabasso et al. | |
| 4,955,861 A | 9/1990 | Enegren et al. | |
| 4,958,148 A | 9/1990 | Olson | |
| 4,960,594 A | 10/1990 | Honeycutt | |
| 4,961,954 A | 10/1990 | Goldberg et al. | |
| 4,963,595 A | 10/1990 | Ward et al. | |
| 4,970,145 A | 11/1990 | Bennetto et al. | |
| 4,973,320 A | 11/1990 | Brenner et al. | |
| 4,974,929 A | 12/1990 | Curry | |
| 4,975,175 A | 12/1990 | Karube et al. | |
| 4,984,929 A | 1/1991 | Rock et al. | |
| 4,986,671 A | 1/1991 | Sun et al. | |
| 4,988,341 A | 1/1991 | Columbus et al. | |
| 4,988,758 A | 1/1991 | Fukuda et al. | |
| 4,992,794 A | 2/1991 | Brouwers | |
| 4,994,167 A | 2/1991 | Shults et al. | |
| 5,002,572 A | 3/1991 | Picha | |
| 5,002,590 A | 3/1991 | Friesen et al. | |
| 5,007,929 A | 4/1991 | Quaid | |
| 5,010,141 A | 4/1991 | Mueller | |
| 5,034,112 A | 7/1991 | Murase et al. | |
| 5,034,461 A | 7/1991 | Lai et al. | |
| 5,045,601 A | 9/1991 | Capelli et al. | |
| 5,050,612 A | 9/1991 | Matsumura | |

| | | |
|---|---|---|
| 5,059,654 A | 10/1991 | Hou et al. |
| 5,063,081 A | 11/1991 | Cozzette et al. |
| 5,067,491 A | 11/1991 | Taylor, II et al. |
| 5,070,169 A | 12/1991 | Robertson et al. |
| 5,071,452 A | 12/1991 | Avrillon et al. |
| 5,089,112 A | 2/1992 | Skotheim et al. |
| 5,094,876 A | 3/1992 | Goldberg et al. |
| 5,100,689 A | 3/1992 | Goldberg et al. |
| 5,101,814 A | 4/1992 | Palti |
| 5,108,819 A | 4/1992 | Heller et al. |
| 5,113,871 A | 5/1992 | Viljanto et al. |
| 5,115,056 A | 5/1992 | Mueller et al. |
| 5,120,813 A | 6/1992 | Ward, Jr. |
| 5,128,408 A | 7/1992 | Tanaka et al. |
| 5,135,297 A | 8/1992 | Valint et al. |
| 5,137,028 A | 8/1992 | Nishimura |
| 5,147,725 A | 9/1992 | Pinchuk |
| 5,155,149 A | 10/1992 | Atwater et al. |
| 5,160,418 A | 11/1992 | Mullen |
| 5,165,407 A | 11/1992 | Wilson et al. |
| 5,169,906 A | 12/1992 | Cray et al. |
| 5,171,689 A | 12/1992 | Kawaguri et al. |
| 5,183,549 A | 2/1993 | Joseph et al. |
| 5,190,041 A | 3/1993 | Palti |
| 5,200,051 A | 4/1993 | Cozzette et al. |
| 5,202,261 A | 4/1993 | Musho et al. |
| 5,208,313 A | 5/1993 | Krishnan |
| 5,212,050 A | 5/1993 | Mier et al. |
| 5,219,965 A | 6/1993 | Valint et al. |
| 5,221,724 A | 6/1993 | Li et al. |
| 5,235,003 A | 8/1993 | Ward et al. |
| 5,242,835 A | 9/1993 | Jensen |
| 5,243,696 A | 9/1993 | Carr et al. |
| 5,249,576 A | 10/1993 | Goldberger et al. |
| 5,250,439 A | 10/1993 | Musho et al. |
| 5,264,104 A | 11/1993 | Gregg et al. |
| 5,266,179 A | 11/1993 | Nankai et al. |
| 5,269,891 A | 12/1993 | Colin |
| 5,271,736 A | 12/1993 | Picha |
| 5,281,319 A | 1/1994 | Kaneko et al. |
| 5,282,848 A | 2/1994 | Schmitt |
| 5,284,140 A | 2/1994 | Allen et al. |
| 5,285,513 A | 2/1994 | Kaufman et al. |
| 5,286,364 A | 2/1994 | Yacynych et al. |
| 5,296,144 A | 3/1994 | Sternina et al. |
| 5,298,144 A | 3/1994 | Spokane |
| 5,299,571 A | 4/1994 | Mastrototaro |
| 5,304,468 A | 4/1994 | Phillips et al. |
| 5,307,263 A | 4/1994 | Brown |
| 5,310,469 A | 5/1994 | Cunningham et al. |
| 5,312,361 A | 5/1994 | Zadini et al. |
| 5,314,471 A | 5/1994 | Brauker et al. |
| 5,316,008 A | 5/1994 | Suga et al. |
| 5,321,414 A | 6/1994 | Alden et al. |
| 5,322,063 A * | 6/1994 | Allen et al. ............... 600/347 |
| 5,324,322 A | 6/1994 | Grill et al. |
| 5,326,356 A | 7/1994 | Della Valle et al. |
| 5,330,521 A | 7/1994 | Cohen |
| 5,330,634 A | 7/1994 | Wong et al. |
| 5,331,555 A | 7/1994 | Hashimoto et al. |
| 5,334,681 A | 8/1994 | Mueller et al. |
| 5,337,747 A | 8/1994 | Neftel |
| 5,340,352 A | 8/1994 | Nakanishi et al. |
| 5,342,409 A | 8/1994 | Mullett |
| 5,342,693 A | 8/1994 | Winters et al. |
| 5,343,869 A | 9/1994 | Pross et al. |
| 5,344,454 A | 9/1994 | Clarke et al. |
| 5,348,788 A | 9/1994 | White |
| 5,352,348 A | 10/1994 | Young et al. |
| 5,352,351 A | 10/1994 | White |
| 5,354,449 A | 10/1994 | Band et al. |
| 5,356,786 A | 10/1994 | Heller et al. |
| 5,372,133 A | 12/1994 | Hogen Esch |
| 5,376,400 A | 12/1994 | Goldberg et al. |
| 5,380,536 A | 1/1995 | Hubbell et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,397,451 A | 3/1995 | Senda et al. |
| 5,397,848 A | 3/1995 | Yang et al. |
| 5,411,647 A | 5/1995 | Johnson et al. |
| 5,411,866 A | 5/1995 | Luong |
| 5,417,395 A | 5/1995 | Fowler et al. |
| 5,421,923 A | 6/1995 | Clarke et al. |
| 5,425,717 A | 6/1995 | Mohiuddin |
| 5,426,158 A | 6/1995 | Mueller et al. |
| 5,428,123 A | 6/1995 | Ward et al. |
| 5,429,735 A | 7/1995 | Johnson et al. |
| 5,431,160 A | 7/1995 | Wilkins |
| 5,438,984 A | 8/1995 | Schoendorfer |
| 5,453,278 A | 9/1995 | Chan et al. |
| 5,462,051 A | 10/1995 | Oka et al. |
| 5,462,064 A | 10/1995 | D'Angelo et al. |
| 5,462,645 A | 10/1995 | Albery et al. |
| 5,466,356 A | 11/1995 | Schneider et al. |
| 5,466,575 A | 11/1995 | Cozzette et al. |
| 5,469,846 A | 11/1995 | Khan |
| 5,474,552 A | 12/1995 | Palti |
| 5,476,094 A | 12/1995 | Allen et al. |
| 5,476,776 A | 12/1995 | Wilkins |
| 5,482,008 A | 1/1996 | Stafford et al. |
| 5,482,473 A | 1/1996 | Lord et al. |
| 5,484,404 A | 1/1996 | Schulman et al. |
| 5,486,776 A | 1/1996 | Chiang |
| 5,491,474 A | 2/1996 | Suni et al. |
| 5,494,562 A | 2/1996 | Maley et al. |
| 5,496,453 A | 3/1996 | Uenoyama et al. |
| 5,497,772 A * | 3/1996 | Schulman et al. ............ 600/347 |
| 5,502,396 A | 3/1996 | Desarzens et al. |
| 5,507,288 A | 4/1996 | Bocker et al. |
| 5,508,509 A | 4/1996 | Yafuso et al. |
| 5,513,636 A | 5/1996 | Palti |
| 5,518,601 A | 5/1996 | Foos et al. |
| 5,521,273 A | 5/1996 | Yilgor et al. |
| 5,531,878 A | 7/1996 | Vadgama et al. |
| 5,538,511 A | 7/1996 | Van Antwerp |
| 5,540,828 A | 7/1996 | Yacynych |
| 5,541,305 A | 7/1996 | Yokota et al. |
| 5,545,220 A | 8/1996 | Andrews et al. |
| 5,545,223 A | 8/1996 | Neuenfeldt et al. |
| 5,549,675 A | 8/1996 | Neuenfeldt et al. |
| 5,552,112 A | 9/1996 | Schiffmann |
| 5,554,339 A | 9/1996 | Cozzette |
| 5,564,439 A | 10/1996 | Picha |
| 5,568,806 A | 10/1996 | Cheney, II et al. |
| 5,569,186 A | 10/1996 | Lord et al. |
| 5,569,462 A | 10/1996 | Martinson et al. |
| 5,571,395 A | 11/1996 | Park et al. |
| 5,575,930 A | 11/1996 | Tietje-Girault et al. |
| 5,578,463 A | 11/1996 | Berka et al. |
| 5,582,184 A | 12/1996 | Ericson et al. |
| 5,582,497 A | 12/1996 | Noguchi |
| 5,582,697 A | 12/1996 | Ikeda et al. |
| 5,584,813 A | 12/1996 | Livingston et al. |
| 5,584,876 A | 12/1996 | Bruchman et al. |
| 5,586,553 A | 12/1996 | Halili et al. |
| 5,588,560 A | 12/1996 | Benedict et al. |
| 5,589,133 A | 12/1996 | Suzuki |
| 5,589,563 A | 12/1996 | Ward et al. |
| 5,590,651 A | 1/1997 | Shaffer et al. |
| 5,593,440 A | 1/1997 | Brauker et al. |
| 5,593,852 A | 1/1997 | Heller et al. |
| 5,607,565 A | 3/1997 | Azarnia et al. |
| 5,611,900 A | 3/1997 | Worden |
| 5,624,537 A | 4/1997 | Turner et al. |
| 5,628,890 A | 5/1997 | Carter et al. |
| 5,640,954 A | 6/1997 | Pfeiffer |
| 5,653,756 A | 8/1997 | Clarke et al. |
| 5,653,863 A | 8/1997 | Genshaw et al. |
| 5,658,330 A | 8/1997 | Carlisle et al. |
| 5,660,163 A | 8/1997 | Schulman et al. |
| 5,665,222 A | 9/1997 | Heller et al. |
| 5,670,097 A | 9/1997 | Duan et al. |
| 5,676,820 A | 10/1997 | Wang et al. |
| 5,682,884 A | 11/1997 | Hill |
| 5,683,562 A | 11/1997 | Schaffar et al. |
| 5,686,829 A | 11/1997 | Girault |

| Patent No. | Date | Inventor |
|---|---|---|
| 5,695,623 A | 12/1997 | Michel et al. |
| 5,700,559 A | 12/1997 | Sheu et al. |
| 5,703,359 A | 12/1997 | Wampler, III |
| 5,704,354 A | 1/1998 | Preidel et al. |
| 5,706,807 A | 1/1998 | Picha |
| 5,707,502 A | 1/1998 | McCaffrey et al. |
| 5,711,861 A | 1/1998 | Ward et al. |
| 5,713,888 A | 2/1998 | Neuenfeldt et al. |
| 5,733,336 A | 3/1998 | Neuenfeldt et al. |
| 5,735,273 A | 4/1998 | Kurnik et al. |
| 5,738,902 A | 4/1998 | Forrestal et al. |
| 5,741,330 A | 4/1998 | Brauker et al. |
| 5,741,634 A | 4/1998 | Nozoe et al. |
| 5,743,262 A | 4/1998 | Lepper, Jr. et al. |
| 5,746,898 A | 5/1998 | Preidel |
| 5,749,832 A | 5/1998 | Vadgama et al. |
| 5,756,632 A | 5/1998 | Ward et al. |
| 5,760,155 A | 6/1998 | Mowrer et al. |
| 5,766,151 A | 6/1998 | Valley et al. |
| 5,766,839 A | 6/1998 | Johnson et al. |
| 5,776,324 A | 7/1998 | Usala |
| 5,777,060 A | 7/1998 | Van Antwerp |
| 5,779,665 A | 7/1998 | Mastrototaro et al. |
| 5,782,912 A | 7/1998 | Brauker et al. |
| 5,783,054 A | 7/1998 | Raguse et al. |
| 5,786,439 A | 7/1998 | Van Antwerp et al. |
| 5,787,900 A | 8/1998 | Butler et al. |
| 5,791,344 A | 8/1998 | Schulman et al. |
| 5,795,453 A | 8/1998 | Gilmartin |
| 5,795,774 A | 8/1998 | Matsumoto et al. |
| 5,798,065 A | 8/1998 | Picha |
| 5,800,420 A | 9/1998 | Gross |
| 5,800,529 A | 9/1998 | Brauker et al. |
| 5,804,048 A | 9/1998 | Wong et al. |
| 5,807,375 A | 9/1998 | Gross et al. |
| 5,807,406 A | 9/1998 | Brauker et al. |
| 5,807,636 A | 9/1998 | Sheu et al. |
| 5,811,487 A | 9/1998 | Schulz, Jr. et al. |
| 5,820,570 A | 10/1998 | Erickson |
| 5,820,622 A | 10/1998 | Gross et al. |
| 5,823,802 A | 10/1998 | Bartley |
| 5,833,603 A | 11/1998 | Kovacs et al. |
| 5,834,583 A | 11/1998 | Hancock et al. |
| 5,837,377 A | 11/1998 | Sheu et al. |
| 5,837,454 A | 11/1998 | Cozzette et al. |
| 5,837,661 A | 11/1998 | Evans et al. |
| 5,837,728 A | 11/1998 | Purcell |
| 5,840,148 A | 11/1998 | Campbell et al. |
| 5,840,240 A | 11/1998 | Stenoien et al. |
| 5,843,069 A | 12/1998 | Butler et al. |
| 5,851,197 A | 12/1998 | Marano et al. |
| 5,861,019 A | 1/1999 | Sun et al. |
| 5,863,400 A | 1/1999 | Drummond et al. |
| 5,863,972 A | 1/1999 | Beckelmann et al. |
| 5,871,514 A | 2/1999 | Wiklund et al. |
| 5,879,373 A | 3/1999 | Roper et al. |
| 5,882,354 A | 3/1999 | Brauker et al. |
| 5,882,494 A | 3/1999 | Van Antwerp |
| 5,885,566 A | 3/1999 | Goldberg |
| 5,895,235 A | 4/1999 | Droz |
| 5,897,578 A | 4/1999 | Wiklund et al. |
| 5,897,955 A | 4/1999 | Drumheller |
| 5,904,708 A | 5/1999 | Goedeke |
| 5,910,554 A | 6/1999 | Kempe et al. |
| 5,913,998 A | 6/1999 | Butler et al. |
| 5,914,026 A | 6/1999 | Blubaugh, Jr. et al. |
| 5,914,182 A | 6/1999 | Drumheller |
| 5,917,346 A | 6/1999 | Gord |
| 5,919,215 A | 7/1999 | Wiklund et al. |
| 5,928,130 A | 7/1999 | Schmidt |
| 5,931,814 A | 8/1999 | Alex et al. |
| 5,932,299 A | 8/1999 | Katoot |
| 5,944,661 A | 8/1999 | Swette et al. |
| 5,945,498 A | 8/1999 | Hopken et al. |
| 5,947,127 A | 9/1999 | Tsugaya et al. |
| 5,954,643 A | 9/1999 | Van Antwerp et al. |
| 5,954,954 A | 9/1999 | Houck et al. |
| 5,955,066 A | 9/1999 | Sako et al. |
| 5,957,854 A | 9/1999 | Besson et al. |
| 5,957,903 A | 9/1999 | Mirzaee et al. |
| 5,959,191 A | 9/1999 | Lewis et al. |
| 5,961,451 A | 10/1999 | Reber et al. |
| 5,963,132 A | 10/1999 | Yoakum |
| 5,964,261 A | 10/1999 | Neuenfeldt et al. |
| 5,964,804 A | 10/1999 | Brauker et al. |
| 5,964,993 A | 10/1999 | Blubaugh et al. |
| 5,965,380 A | 10/1999 | Heller et al. |
| 5,969,076 A | 10/1999 | Lai et al. |
| 5,972,199 A | 10/1999 | Heller |
| 5,976,085 A | 11/1999 | Kimball et al. |
| 5,977,241 A | 11/1999 | Koloski et al. |
| 5,985,129 A | 11/1999 | Gough et al. |
| 5,989,409 A | 11/1999 | Kurnik et al. |
| 5,999,848 A | 12/1999 | Gord et al. |
| 6,001,067 A | 12/1999 | Shults et al. |
| 6,001,471 A | 12/1999 | Bries et al. |
| 6,002,954 A | 12/1999 | Van Antwerp et al. |
| 6,007,845 A | 12/1999 | Domb |
| 6,011,984 A | 1/2000 | Van Antwerp et al. |
| 6,013,113 A | 1/2000 | Mika |
| 6,016,448 A | 1/2000 | Busacker et al. |
| 6,018,013 A | 1/2000 | Yoshida et al. |
| 6,018,033 A | 1/2000 | Chen et al. |
| 6,022,463 A | 2/2000 | Leader et al. |
| 6,030,827 A | 2/2000 | Davis et al. |
| 6,039,913 A | 3/2000 | Hirt et al. |
| 6,043,328 A | 3/2000 | Domschke et al. |
| 6,049,727 A | 4/2000 | Crothall |
| 6,051,389 A | 4/2000 | Ahl et al. |
| 6,059,946 A | 5/2000 | Yukawa et al. |
| 6,063,637 A | 5/2000 | Arnold et al. |
| 6,066,083 A | 5/2000 | Slater et al. |
| 6,066,448 A | 5/2000 | Wohlstadter et al. |
| 6,071,406 A | 6/2000 | Tsou |
| 6,074,775 A | 6/2000 | Gartstein et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,093,156 A | 7/2000 | Cunningham et al. |
| 6,093,172 A | 7/2000 | Funderburk et al. |
| 6,103,033 A | 8/2000 | Say et al. |
| 6,115,634 A | 9/2000 | Donders et al. |
| 6,117,290 A | 9/2000 | Say |
| 6,119,028 A | 9/2000 | Schulman et al. |
| 6,121,009 A | 9/2000 | Heller et al. |
| 6,122,536 A | 9/2000 | Sun et al. |
| 6,134,461 A | 10/2000 | Say et al. |
| 6,135,978 A | 10/2000 | Houben et al. |
| 6,144,869 A | 11/2000 | Berner et al. |
| 6,144,871 A | 11/2000 | Saito et al. |
| 6,162,611 A | 12/2000 | Heller et al. |
| 6,167,614 B1 | 1/2001 | Tuttle et al. |
| 6,169,155 B1 | 1/2001 | Alvarez et al. |
| 6,175,752 B1 | 1/2001 | Say et al. |
| 6,180,416 B1 | 1/2001 | Kurnik et al. |
| 6,187,062 B1 | 2/2001 | Oweis et al. |
| 6,189,536 B1 | 2/2001 | Martinez et al. |
| 6,200,772 B1 | 3/2001 | Vadgama et al. |
| 6,201,980 B1 | 3/2001 | Darrow et al. |
| 6,206,856 B1 | 3/2001 | Mahurkar |
| 6,208,894 B1 | 3/2001 | Schulman et al. |
| 6,212,416 B1 | 4/2001 | Ward et al. |
| 6,214,185 B1 | 4/2001 | Offenbacher et al. |
| 6,223,083 B1 | 4/2001 | Rosar |
| 6,230,059 B1 | 5/2001 | Duffin |
| 6,231,879 B1 | 5/2001 | Li et al. |
| 6,233,471 B1 | 5/2001 | Berner et al. |
| 6,241,863 B1 | 6/2001 | Monbouquette |
| 6,248,067 B1 | 6/2001 | Causey, III et al. |
| 6,254,586 B1 | 7/2001 | Mann et al. |
| 6,255,592 B1 | 7/2001 | Pennington et al. |
| 6,256,522 B1 | 7/2001 | Schultz |
| 6,259,937 B1 | 7/2001 | Schulman et al. |
| 6,264,825 B1 | 7/2001 | Blackburn et al. |
| 6,268,161 B1 | 7/2001 | Han et al. |
| 6,271,332 B1 | 8/2001 | Lohmann et al. |
| 6,272,364 B1 | 8/2001 | Kurnik |

| | | |
|---|---|---|
| 6,272,382 B1 | 8/2001 | Faltys et al. |
| 6,274,285 B1 | 8/2001 | Gries et al. |
| 6,275,717 B1 | 8/2001 | Gross et al. |
| 6,284,478 B1 | 9/2001 | Heller et al. |
| 6,285,897 B1 | 9/2001 | Kilcoyne et al. |
| 6,293,925 B1 | 9/2001 | Safabash et al. |
| 6,294,281 B1 | 9/2001 | Heller |
| 6,299,578 B1 | 10/2001 | Kurnik et al. |
| 6,300,002 B1 | 10/2001 | Webb et al. |
| 6,303,670 B1 | 10/2001 | Fujino et al. |
| 6,306,594 B1 | 10/2001 | Cozzette |
| 6,309,351 B1 | 10/2001 | Kurnik et al. |
| 6,309,384 B1 | 10/2001 | Harrington et al. |
| 6,309,526 B1 | 10/2001 | Fujiwara et al. |
| 6,312,706 B1 | 11/2001 | Lai et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,488 B1 | 12/2001 | Terry et al. |
| 6,330,464 B1 | 12/2001 | Colvin, Jr. et al. |
| 6,343,225 B1 | 1/2002 | Clark, Jr. |
| 6,358,557 B1 | 3/2002 | Wang et al. |
| 6,360,888 B1 | 3/2002 | McIvor et al. |
| 6,365,670 B1 | 4/2002 | Fry |
| 6,366,794 B1 | 4/2002 | Moussy et al. |
| 6,368,141 B1 | 4/2002 | VanAntwerp et al. |
| 6,368,274 B1 | 4/2002 | Van Antwerp et al. |
| 6,368,658 B1 | 4/2002 | Schwarz et al. |
| 6,372,244 B1 | 4/2002 | Antanavich et al. |
| 6,387,379 B1 | 5/2002 | Goldberg et al. |
| 6,400,974 B1 | 6/2002 | Lesho |
| 6,405,066 B1 | 6/2002 | Essenpreis et al. |
| 6,406,066 B1 | 6/2002 | Uegane |
| 6,407,195 B2 | 6/2002 | Sherman et al. |
| 6,409,674 B1 | 6/2002 | Brockway et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,442,413 B1 | 8/2002 | Silver |
| 6,447,448 B1 | 9/2002 | Ishikawa et al. |
| 6,447,542 B1 | 9/2002 | Weadock |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,484,045 B1 | 11/2002 | Holker et al. |
| 6,484,046 B1 | 11/2002 | Say et al. |
| 6,498,043 B1 | 12/2002 | Schulman et al. |
| 6,498,941 B1 | 12/2002 | Jackson |
| 6,510,329 B2 | 1/2003 | Heckel |
| 6,512,939 B1 | 1/2003 | Colvin et al. |
| 6,514,718 B2 | 2/2003 | Heller et al. |
| 6,520,326 B2 | 2/2003 | McIvor et al. |
| 6,520,997 B1 | 2/2003 | Pekkarinen et al. |
| 6,527,729 B1 | 3/2003 | Turcott |
| 6,528,584 B2 | 3/2003 | Kennedy et al. |
| 6,534,711 B1 | 3/2003 | Pollack |
| 6,537,318 B1 | 3/2003 | Ita et al. |
| 6,541,107 B1 | 4/2003 | Zhang et al. |
| 6,545,085 B2 | 4/2003 | Kilgour et al. |
| 6,546,268 B1 | 4/2003 | Ishikawa et al. |
| 6,547,839 B2 | 4/2003 | Zhang et al. |
| 6,551,496 B1 | 4/2003 | Moles et al. |
| 6,553,241 B2 | 4/2003 | Mannheimer et al. |
| 6,554,982 B1 | 4/2003 | Shin et al. |
| 6,558,320 B1 | 5/2003 | Causey |
| 6,558,321 B1 | 5/2003 | Burd et al. |
| 6,558,351 B1 | 5/2003 | Steil et al. |
| 6,560,471 B1 | 5/2003 | Heller et al. |
| 6,565,509 B1 | 5/2003 | Say et al. |
| 6,569,309 B2 | 5/2003 | Otsuka et al. |
| 6,569,521 B1 | 5/2003 | Sheridan et al. |
| 6,579,498 B1 | 6/2003 | Eglise |
| 6,584,335 B1 | 6/2003 | Haar et al. |
| 6,585,763 B1 | 7/2003 | Keilman et al. |
| 6,591,125 B1 | 7/2003 | Buse et al. |
| 6,596,294 B2 | 7/2003 | Lai et al. |
| 6,607,509 B2 | 8/2003 | Bobroff et al. |
| 6,612,984 B1 | 9/2003 | Kerr, II |
| 6,613,379 B2 | 9/2003 | Ward et al. |
| 6,615,078 B1 | 9/2003 | Burson et al. |
| 6,618,934 B1 | 9/2003 | Feldman et al. |
| 6,633,772 B2 | 10/2003 | Ford et al. |
| 6,642,015 B2 | 11/2003 | Vachon et al. |
| 6,645,181 B1 | 11/2003 | Lavi et al. |
| 6,648,821 B2 | 11/2003 | Lebel et al. |
| 6,654,625 B1 | 11/2003 | Say et al. |
| 6,670,115 B1 | 12/2003 | Zhang |
| 6,683,535 B1 | 1/2004 | Utke |
| 6,689,265 B2 | 2/2004 | Heller et al. |
| 6,694,191 B2 | 2/2004 | Starkweather et al. |
| 6,695,860 B1 | 2/2004 | Ward et al. |
| 6,699,218 B2 | 3/2004 | Flaherty et al. |
| 6,699,383 B2 | 3/2004 | Lemire et al. |
| 6,702,857 B2 | 3/2004 | Brauker et al. |
| 6,702,972 B1 | 3/2004 | Markle |
| 6,721,587 B2 | 4/2004 | Gough |
| 6,730,200 B1 | 5/2004 | Stewart et al. |
| 6,731,976 B2 | 5/2004 | Penn et al. |
| 6,733,655 B1 | 5/2004 | Davies et al. |
| 6,737,158 B1 | 5/2004 | Thompson |
| 6,740,075 B2 | 5/2004 | Lebel et al. |
| 6,741,877 B1 | 5/2004 | Shults et al. |
| 6,742,635 B2 | 6/2004 | Hirshberg |
| 6,743,635 B2 | 6/2004 | Neel et al. |
| 6,773,565 B2 | 8/2004 | Kunimoto et al. |
| 6,784,274 B2 | 8/2004 | van Antwerp et al. |
| 6,789,634 B1 | 9/2004 | Denton |
| 6,793,789 B2 | 9/2004 | Choi et al. |
| 6,793,802 B2 | 9/2004 | Lee et al. |
| 6,801,041 B2 | 10/2004 | Karinka et al. |
| 6,802,957 B2 | 10/2004 | Jung et al. |
| 6,809,653 B1 | 10/2004 | Mann et al. |
| 6,810,290 B2 | 10/2004 | Lebel et al. |
| 6,858,218 B2 | 2/2005 | Lai et al. |
| 6,862,465 B2 | 3/2005 | Shults et al. |
| 6,867,262 B2 | 3/2005 | Angel et al. |
| 6,881,551 B2 | 4/2005 | Heller et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,895,265 B2 | 5/2005 | Silver |
| 6,908,681 B2 | 6/2005 | Terry et al. |
| 6,932,894 B2 | 8/2005 | Mao et al. |
| 6,952,604 B2 | 10/2005 | DeNuzzio et al. |
| 6,965,791 B1 | 11/2005 | Hitchcock et al. |
| 6,969,451 B2 | 11/2005 | Shin et al. |
| 6,972,080 B1 | 12/2005 | Tomioka et al. |
| 6,973,706 B2 | 12/2005 | Say et al. |
| 7,003,336 B2 | 2/2006 | Holker et al. |
| 7,003,341 B2 | 2/2006 | Say et al. |
| 7,008,979 B2 | 3/2006 | Schottman et al. |
| 7,014,948 B2 | 3/2006 | Lee et al. |
| 7,033,322 B2 | 4/2006 | Silver |
| 7,052,131 B2 | 5/2006 | McCabe et al. |
| 7,058,437 B2 | 6/2006 | Buse et al. |
| 7,060,059 B2 | 6/2006 | Keith et al. |
| 7,070,580 B2 | 7/2006 | Nielsen |
| 7,074,307 B2 | 7/2006 | Simpson et al. |
| 7,078,582 B2 | 7/2006 | Stebbings et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,115,884 B1 | 10/2006 | Walt et al. |
| 7,118,667 B2 | 10/2006 | Lee |
| 7,120,483 B2 | 10/2006 | Russell et al. |
| 7,134,999 B2 | 11/2006 | Brauker et al. |
| 7,136,689 B2 | 11/2006 | Shults et al. |
| 7,153,265 B2 | 12/2006 | Vachon |
| 7,166,074 B2 | 1/2007 | Reghabi et al. |
| 7,169,289 B2 | 1/2007 | Schulein et al. |

| Patent No. | Date | Inventor |
|---|---|---|
| 7,172,075 B1 | 2/2007 | ji |
| 7,190,988 B2 | 3/2007 | Say et al. |
| 7,192,450 B2 | 3/2007 | Brauker et al. |
| 7,207,974 B2 | 4/2007 | Safabash et al. |
| 7,225,535 B2 | 6/2007 | Feldman et al. |
| 7,226,978 B2 | 6/2007 | Tapsak et al. |
| 7,229,471 B2 | 6/2007 | Gale et al. |
| 7,241,586 B2 | 7/2007 | Gulati |
| 7,248,906 B2 | 7/2007 | Dirac et al. |
| 7,267,665 B2 | 9/2007 | Steil et al. |
| 7,279,174 B2 | 10/2007 | Pacetti et al. |
| 7,310,544 B2 | 12/2007 | Brister et al. |
| 7,335,286 B2 | 2/2008 | Abel et al. |
| 7,336,984 B2 | 2/2008 | Gough et al. |
| 7,344,499 B1 | 3/2008 | Prausnitz et al. |
| 7,357,793 B2 | 4/2008 | Pacetti |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,399,277 B2 | 7/2008 | Saidara et al. |
| 7,417,164 B2 | 8/2008 | Suri |
| 7,423,074 B2 | 9/2008 | Lai et al. |
| 7,424,318 B2 | 9/2008 | Brister et al. |
| 7,426,408 B2 | 9/2008 | DeNuzzio et al. |
| 7,460,898 B2 | 12/2008 | Brister et al. |
| 7,467,003 B2 | 12/2008 | Brister et al. |
| 7,470,488 B2 | 12/2008 | Lee et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,687,586 B2 | 3/2010 | Ward et al. |
| 7,881,763 B2 | 2/2011 | Brauker et al. |
| 8,050,731 B2 | 11/2011 | Tapsak et al. |
| 8,053,018 B2 | 11/2011 | Tapsak et al. |
| 2002/0016535 A1 | 2/2002 | Martin et al. |
| 2002/0018843 A1 | 2/2002 | Van Antwerp et al. |
| 2002/0022883 A1 | 2/2002 | Burg |
| 2002/0023852 A1 | 2/2002 | McIvor et al. |
| 2002/0025580 A1 | 2/2002 | Vadgama et al. |
| 2002/0042090 A1 | 4/2002 | Heller et al. |
| 2002/0042561 A1 | 4/2002 | Schulman et al. |
| 2002/0055673 A1 | 5/2002 | Van Antwerp et al. |
| 2002/0084196 A1 | 7/2002 | Liamos et al. |
| 2002/0099997 A1 | 7/2002 | Piret |
| 2002/0119711 A1 | 8/2002 | Van Antwerp et al. |
| 2002/0120186 A1* | 8/2002 | Keimel ............... 600/365 |
| 2002/0123087 A1 | 9/2002 | Vachon et al. |
| 2002/0128546 A1 | 9/2002 | Silver |
| 2002/0151796 A1 | 10/2002 | Koulik |
| 2002/0161288 A1 | 10/2002 | Shin et al. |
| 2002/0169369 A1 | 11/2002 | Ward et al. |
| 2002/0177763 A1 | 11/2002 | Burns et al. |
| 2002/0182241 A1 | 12/2002 | Borenstein et al. |
| 2002/0185384 A1 | 12/2002 | Leong et al. |
| 2002/0188185 A1 | 12/2002 | Sohrab |
| 2002/0193885 A1 | 12/2002 | Legeay et al. |
| 2003/0004457 A1 | 1/2003 | Andersson |
| 2003/0006669 A1 | 1/2003 | Pei et al. |
| 2003/0009093 A1 | 1/2003 | Silver |
| 2003/0023317 A1 | 1/2003 | Brauker et al. |
| 2003/0032874 A1 | 2/2003 | Rhodes et al. |
| 2003/0036773 A1 | 2/2003 | Whitehurst et al. |
| 2003/0036803 A1 | 2/2003 | McGhan |
| 2003/0059631 A1 | 3/2003 | Al-Lamee |
| 2003/0065254 A1 | 4/2003 | Schulman et al. |
| 2003/0069383 A1 | 4/2003 | Van Antwerp et al. |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0088166 A1 | 5/2003 | Say et al. |
| 2003/0091433 A1 | 5/2003 | Tam et al. |
| 2003/0096424 A1 | 5/2003 | Mao et al. |
| 2003/0097082 A1 | 5/2003 | Purdy et al. |
| 2003/0100040 A1 | 5/2003 | Bonnecaze et al. |
| 2003/0104273 A1 | 6/2003 | Lee et al. |
| 2003/0125498 A1 | 7/2003 | McCabe et al. |
| 2003/0125613 A1 | 7/2003 | Enegren et al. |
| 2003/0130616 A1 | 7/2003 | Steil et al. |
| 2003/0132227 A1 | 7/2003 | Geisler |
| 2003/0134100 A1 | 7/2003 | Mao et al. |
| 2003/0134347 A1 | 7/2003 | Heller et al. |
| 2003/0138674 A1 | 7/2003 | Zeikus et al. |
| 2003/0157409 A1 | 8/2003 | Huang et al. |
| 2003/0181794 A1 | 9/2003 | Rini et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199745 A1 | 10/2003 | Burson et al. |
| 2003/0199878 A1 | 10/2003 | Pohjonen |
| 2003/0203498 A1 | 10/2003 | Neel et al. |
| 2003/0203991 A1 | 10/2003 | Schottman et al. |
| 2003/0211050 A1 | 11/2003 | Majeti et al. |
| 2003/0211625 A1 | 11/2003 | Cohan |
| 2003/0217966 A1 | 11/2003 | Tapsak et al. |
| 2003/0225324 A1 | 12/2003 | Anderson et al. |
| 2003/0225361 A1 | 12/2003 | Sabra |
| 2003/0225437 A1 | 12/2003 | Ferguson |
| 2003/0228681 A1 | 12/2003 | Ritts et al. |
| 2003/0235817 A1 | 12/2003 | Bartkowiak et al. |
| 2004/0006263 A1 | 1/2004 | Anderson et al. |
| 2004/0010207 A1 | 1/2004 | Flaherty et al. |
| 2004/0015063 A1 | 1/2004 | DeNuzzio et al. |
| 2004/0015134 A1 | 1/2004 | Lavi et al. |
| 2004/0018486 A1 | 1/2004 | Dunn et al. |
| 2004/0030285 A1 | 2/2004 | Lavi et al. |
| 2004/0030294 A1 | 2/2004 | Mahurkar |
| 2004/0039406 A1 | 2/2004 | Jessen |
| 2004/0045879 A1 | 3/2004 | Shults et al. |
| 2004/0063167 A1 | 4/2004 | Kaastrup et al. |
| 2004/0068230 A1 | 4/2004 | Estes et al. |
| 2004/0074785 A1 | 4/2004 | Holker |
| 2004/0077075 A1 | 4/2004 | Jensen et al. |
| 2004/0078219 A1 | 4/2004 | Kaylor |
| 2004/0084306 A1 | 5/2004 | Shin et al. |
| 2004/0106741 A1 | 6/2004 | Kriesel et al. |
| 2004/0106857 A1 | 6/2004 | Gough |
| 2004/0111017 A1 | 6/2004 | Say et al. |
| 2004/0111144 A1 | 6/2004 | Lawin et al. |
| 2004/0120848 A1 | 6/2004 | Teodorczyk |
| 2004/0133131 A1 | 7/2004 | Kuhn et al. |
| 2004/0133164 A1 | 7/2004 | Funderburk et al. |
| 2004/0138543 A1 | 7/2004 | Russell et al. |
| 2004/0143173 A1 | 7/2004 | Reghabi et al. |
| 2004/0146909 A1 | 7/2004 | Duong et al. |
| 2004/0158138 A1 | 8/2004 | Kilcoyne et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2004/0204687 A1 | 10/2004 | Mogensen |
| 2004/0213985 A1 | 10/2004 | Lee et al. |
| 2004/0219664 A1 | 11/2004 | Heller et al. |
| 2004/0224001 A1 | 11/2004 | Pacetti et al. |
| 2004/0228902 A1 | 11/2004 | Benz |
| 2004/0234575 A1 | 11/2004 | Horres et al. |
| 2004/0236200 A1 | 11/2004 | Say et al. |
| 2004/0236251 A1 | 11/2004 | Roe et al. |
| 2004/0242982 A1 | 12/2004 | Sakata et al. |
| 2004/0254433 A1 | 12/2004 | Bandis |
| 2005/0006122 A1 | 1/2005 | Burnette |
| 2005/0013842 A1 | 1/2005 | Qiu et al. |
| 2005/0027182 A1 | 2/2005 | Siddiqui et al. |
| 2005/0031689 A1 | 2/2005 | Shults et al. |
| 2005/0032246 A1 | 2/2005 | Brennan et al. |
| 2005/0033132 A1 | 2/2005 | Shults et al. |
| 2005/0038332 A1 | 2/2005 | Saidara et al. |
| 2005/0051427 A1 | 3/2005 | Brauker et al. |
| 2005/0054909 A1 | 3/2005 | Petisce et al. |
| 2005/0056551 A1 | 3/2005 | White et al. |
| 2005/0056552 A1 | 3/2005 | Simpson et al. |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0090607 A1 | 4/2005 | Tapsak et al. |

| Publication No. | Date | Inventor |
|---|---|---|
| 2005/0044088 A1 | 5/2005 | Agus |
| 2005/0096519 A1 | 5/2005 | DeNuzzio et al. |
| 2005/0107677 A1 | 5/2005 | Ward et al. |
| 2005/0112169 A1 | 5/2005 | Brauker et al. |
| 2005/0112172 A1 | 5/2005 | Pacetti |
| 2005/0112358 A1 | 5/2005 | Potyrailo et al. |
| 2005/0118344 A1 | 6/2005 | Pacetti |
| 2005/0119720 A1 | 6/2005 | Gale et al. |
| 2005/0121322 A1 | 6/2005 | Say |
| 2005/0124873 A1 | 6/2005 | Shults et al. |
| 2005/0133368 A1 | 6/2005 | Davies et al. |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154272 A1 | 7/2005 | Dirac et al. |
| 2005/0173245 A1 | 8/2005 | Feldman et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0181012 A1 | 8/2005 | Saint et al. |
| 2005/0182451 A1 | 8/2005 | Griffin et al. |
| 2005/0183954 A1 | 8/2005 | Hitchcock et al. |
| 2005/0184641 A1 | 8/2005 | Armitage et al. |
| 2005/0192557 A1 | 9/2005 | Brauker et al. |
| 2005/0195930 A1 | 9/2005 | Spital et al. |
| 2005/0196747 A1 | 9/2005 | Stiene |
| 2005/0197554 A1 | 9/2005 | Polcha |
| 2005/0209665 A1 | 9/2005 | Hunter et al. |
| 2005/0211571 A1 | 9/2005 | Schulein et al. |
| 2005/0215871 A1 | 9/2005 | Feldman et al. |
| 2005/0233407 A1 | 10/2005 | Pamidi et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0258037 A1 | 11/2005 | Hajizadeh et al. |
| 2005/0261563 A1 | 11/2005 | Zhou et al. |
| 2005/0266582 A1 | 12/2005 | Modlin et al. |
| 2005/0271546 A1 | 12/2005 | Gerber et al. |
| 2005/0272989 A1 | 12/2005 | Shah et al. |
| 2005/0274665 A1 | 12/2005 | Heilmann et al. |
| 2005/0282997 A1 | 12/2005 | Ward |
| 2006/0003398 A1 | 1/2006 | Heller et al. |
| 2006/0007391 A1 | 1/2006 | McCabe et al. |
| 2006/0008370 A1 | 1/2006 | Massaro et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0047095 A1 | 3/2006 | Pacetti |
| 2006/0058868 A1 | 3/2006 | Gale et al. |
| 2006/0065527 A1 | 3/2006 | Samproni |
| 2006/0067908 A1 | 3/2006 | Ding |
| 2006/0068208 A1 | 3/2006 | Tapsak et al. |
| 2006/0078908 A1 | 4/2006 | Pitner et al. |
| 2006/0079740 A1 | 4/2006 | Silver et al. |
| 2006/0086624 A1 | 4/2006 | Tapsak et al. |
| 2006/0134165 A1 | 6/2006 | Pacetti |
| 2006/0142524 A1 | 6/2006 | Lai et al. |
| 2006/0142525 A1 | 6/2006 | Lai et al. |
| 2006/0142526 A1 | 6/2006 | Lai et al. |
| 2006/0142651 A1 | 6/2006 | Brister et al. |
| 2006/0148985 A1 | 7/2006 | Karthauser |
| 2006/0155180 A1 | 7/2006 | Brister et al. |
| 2006/0159718 A1 | 7/2006 | Rathenow et al. |
| 2006/0171980 A1 | 8/2006 | Helmus et al. |
| 2006/0173444 A1 | 8/2006 | Choy et al. |
| 2006/0177379 A1 | 8/2006 | Asgari |
| 2006/0183178 A1 | 8/2006 | Gulati |
| 2006/0183871 A1 | 8/2006 | Ward et al. |
| 2006/0183984 A1 | 8/2006 | Dobbles et al. |
| 2006/0183985 A1 | 8/2006 | Brister et al. |
| 2006/0189856 A1 | 8/2006 | Petisce et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0204536 A1 | 9/2006 | Shults et al. |
| 2006/0211921 A1 | 9/2006 | Brauker et al. |
| 2006/0222566 A1 | 10/2006 | Brauker et al. |
| 2006/0224108 A1 | 10/2006 | Brauker et al. |
| 2006/0229512 A1 | 10/2006 | Petisce et al. |
| 2006/0235285 A1 | 10/2006 | Brister et al. |
| 2006/0249381 A1 | 11/2006 | Petisce et al. |
| 2006/0249446 A1 | 11/2006 | Yeager |
| 2006/0249447 A1 | 11/2006 | Yeager |
| 2006/0252027 A1 | 11/2006 | Petisce et al. |
| 2006/0253012 A1 | 11/2006 | Petisce et al. |
| 2006/0258761 A1 | 11/2006 | Boock et al. |
| 2006/0258929 A1 | 11/2006 | Goode et al. |
| 2006/0263673 A1 | 11/2006 | Kim et al. |
| 2006/0263839 A1 | 11/2006 | Ward et al. |
| 2006/0269586 A1 | 11/2006 | Pacetti |
| 2006/0270922 A1 | 11/2006 | Brauker et al. |
| 2006/0270923 A1 | 11/2006 | Brauker et al. |
| 2006/0275857 A1 | 12/2006 | Kjaer et al. |
| 2006/0275859 A1 | 12/2006 | Kjaer |
| 2006/0289307 A1 | 12/2006 | Yu et al. |
| 2006/0293487 A1 | 12/2006 | Gaymans et al. |
| 2007/0003588 A1 | 1/2007 | Chinn et al. |
| 2007/0007133 A1 | 1/2007 | Mang et al. |
| 2007/0017805 A1 | 1/2007 | Hodges et al. |
| 2007/0032718 A1 | 2/2007 | Shults et al. |
| 2007/0038044 A1 | 2/2007 | Dobbles et al. |
| 2007/0045902 A1 | 3/2007 | Brauker et al. |
| 2007/0059196 A1 | 3/2007 | Brister et al. |
| 2007/0123963 A1 | 5/2007 | Krulevitch |
| 2007/0129524 A1 | 6/2007 | Sunkara |
| 2007/0135698 A1 | 6/2007 | Shah et al. |
| 2007/0142584 A1 | 6/2007 | Schorzman et al. |
| 2007/0155851 A1 | 7/2007 | Alli et al. |
| 2007/0161769 A1 | 7/2007 | Schorzman et al. |
| 2007/0163880 A1 | 7/2007 | Woo et al. |
| 2007/0166343 A1 | 7/2007 | Goerne et al. |
| 2007/0166364 A1 | 7/2007 | Beier et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |
| 2007/0197889 A1 | 8/2007 | Brister et al. |
| 2007/0197890 A1 | 8/2007 | Boock et al. |
| 2007/0200254 A1 | 8/2007 | Curry |
| 2007/0200267 A1 | 8/2007 | Tsai |
| 2007/0202562 A1 | 8/2007 | Curry |
| 2007/0202672 A1 | 8/2007 | Curry |
| 2007/0203568 A1 | 8/2007 | Gale et al. |
| 2007/0203966 A1 | 8/2007 | Brauker et al. |
| 2007/0208246 A1 | 9/2007 | Brauker et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0229757 A1 | 10/2007 | McCabe et al. |
| 2007/0232879 A1 | 10/2007 | Brister et al. |
| 2007/0233013 A1 | 10/2007 | Schoenberg |
| 2007/0235331 A1 | 10/2007 | Simpson et al. |
| 2007/0242215 A1 | 10/2007 | Schorzman et al. |
| 2007/0244379 A1 | 10/2007 | Boock et al. |
| 2007/0259217 A1 | 11/2007 | Logan |
| 2007/0275193 A1 | 11/2007 | DeSimone et al. |
| 2007/0299385 A1 | 12/2007 | Santini et al. |
| 2007/0299409 A1 | 12/2007 | Whitbourne et al. |
| 2008/0001318 A1 | 1/2008 | Schorzman et al. |
| 2008/0021008 A1 | 1/2008 | Pacetti et al. |
| 2008/0021666 A1 | 1/2008 | Goode et al. |
| 2008/0027301 A1 | 1/2008 | Ward et al. |
| 2008/0031918 A1 | 2/2008 | Lawin et al. |
| 2008/0033269 A1 | 2/2008 | Zhang |

| | | | | | | |
|---|---|---|---|---|---|---|
| 2008/0034972 | A1 | 2/2008 | Gough et al. | FR | 2656423 | 6/1991 |
| 2008/0038307 | A1 | 2/2008 | Hoffmann | FR | 2760962 | 9/1998 |
| 2008/0045824 | A1 | 2/2008 | Tapsak et al. | GB | 1 442 303 | 7/1976 |
| 2008/0071027 | A1 | 3/2008 | Pacetti | GB | 2149918 | 6/1985 |
| 2008/0076897 | A1 | 3/2008 | Kunzler et al. | GB | 2209836 | 5/1989 |
| 2008/0081184 | A1 | 4/2008 | Kubo et al. | JP | 57156004 | 9/1982 |
| 2008/0113207 | A1 | 5/2008 | Pacetti et al. | JP | 57156005 | 9/1982 |
| 2008/0138497 | A1 | 6/2008 | Pacetti et al. | JP | 58163402 | 9/1983 |
| 2008/0138498 | A1 | 6/2008 | Pacetti et al. | JP | 58163403 | 9/1983 |
| 2008/0143014 | A1 | 6/2008 | Tang | JP | 59029693 | 2/1984 |
| 2008/0154101 | A1 | 6/2008 | Jain et al. | JP | 59049803 | 3/1984 |
| 2008/0187655 | A1 | 8/2008 | Markle et al. | JP | 59049805 | 3/1984 |
| 2008/0188722 | A1 | 8/2008 | Markle et al. | JP | 59059221 | 4/1984 |
| 2008/0188725 | A1 | 8/2008 | Markle et al. | JP | 59087004 | 5/1984 |
| 2008/0188731 | A1 | 8/2008 | Brister et al. | JP | 59-211459 | 11/1984 |
| 2008/0194935 | A1 | 8/2008 | Brister et al. | JP | 59209608 | 11/1984 |
| 2008/0194938 | A1 | 8/2008 | Brister et al. | JP | 59209609 | 11/1984 |
| 2008/0208025 | A1 | 8/2008 | Shults et al. | JP | 59209610 | 11/1984 |
| 2008/0213460 | A1 | 9/2008 | Benter et al. | JP | 60245623 | 12/1985 |
| 2008/0214915 | A1 | 9/2008 | Brister et al. | JP | 61238319 | 10/1986 |
| 2008/0214918 | A1 | 9/2008 | Brister et al. | JP | 62074406 | 4/1987 |
| 2008/0242961 | A1 | 10/2008 | Brister et al. | JP | 62083649 | 4/1987 |
| 2008/0262334 | A1 | 10/2008 | Dunn et al. | JP | 62083849 | 4/1987 |
| 2008/0275313 | A1 | 11/2008 | Brister et al. | JP | 62102815 | 5/1987 |
| 2008/0296155 | A1 | 12/2008 | Shults et al. | JP | 62227423 | 10/1987 |
| 2008/0305009 | A1 | 12/2008 | Gamsey et al. | JP | 63130661 | 6/1988 |
| 2008/0305506 | A1 | 12/2008 | Suri | JP | 01018404 | 1/1989 |
| 2008/0306368 | A1 | 12/2008 | Goode et al. | JP | 01018405 | 1/1989 |
| 2008/0312397 | A1 | 12/2008 | Lai et al. | JP | 02002913 | 1/1990 |
| 2009/0004243 | A1 | 1/2009 | Pacetti et al. | JP | 3-293556 | 12/1991 |
| 2009/0012205 | A1 | 1/2009 | Nakada et al. | JP | 05279447 | 10/1993 |
| 2009/0012379 | A1 | 1/2009 | Goode et al. | JP | 8196626 | 8/1996 |
| 2009/0018418 | A1 | 1/2009 | Markle et al. | JP | 2002-189015 | 7/2002 |
| 2009/0018426 | A1 | 1/2009 | Markle et al. | WO | WO 89/02720 | 4/1989 |
| 2009/0030294 | A1 | 1/2009 | Petisce et al. | WO | WO 90/00738 | 1/1990 |
| 2009/0061528 | A1 | 3/2009 | Suri | WO | WO 90/07575 | 7/1990 |
| 2009/0062633 | A1 | 3/2009 | Brauker et al. | WO | WO 91/09302 | 6/1991 |
| 2009/0076356 | A1 | 3/2009 | Simpson | WO | WO 92/07525 | 5/1992 |
| 2009/0076360 | A1 | 3/2009 | Brister et al. | WO | WO 92/13271 | 8/1992 |
| 2009/0081803 | A1 | 3/2009 | Gamsey et al. | WO | WO 93/14185 | 7/1993 |
| 2009/0099436 | A1 | 4/2009 | Brister et al. | WO | WO 93/14693 | 8/1993 |
| 2009/0124879 | A1 | 5/2009 | Brister et al. | WO | WO 93/19701 | 10/1993 |
| 2009/0143660 | A1 | 6/2009 | Brister et al. | WO | WO 93/23744 | 11/1993 |
| 2009/0177143 | A1 | 7/2009 | Markle et al. | WO | WO 94/08236 | 4/1994 |
| 2009/0182217 | A1 | 7/2009 | Li et al. | WO | WO 94/22367 | 10/1994 |
| 2009/0192751 | A1 | 7/2009 | Kamath et al. | WO | WO 96/25089 | 2/1995 |
| 2009/0242399 | A1 | 10/2009 | Kamath et al. | WO | WO 95/07109 | 3/1995 |
| 2009/0242425 | A1 | 10/2009 | Kamath et al. | WO | WO 96/01611 | 1/1996 |
| 2009/0247855 | A1 | 10/2009 | Boock et al. | WO | WO 96/14026 | 5/1996 |
| 2009/0247856 | A1 | 10/2009 | Boock et al. | WO | WO 96/25089 | 8/1996 |
| 2009/0264719 | A1 | 10/2009 | Markle et al. | WO | WO 96/30431 | 10/1996 |
| 2011/0124992 | A1 | 5/2011 | Brauker et al. | WO | WO 96/32076 | 10/1996 |
| 2011/0147300 | A1 | 6/2011 | Xiao et al. | WO | WO 96/36296 | 11/1996 |
| 2011/0253533 | A1 | 10/2011 | Shults et al. | WO | WO 97/01986 | 1/1997 |
| | | | | WO | WO 97/06727 | 2/1997 |
| | FOREIGN PATENT DOCUMENTS | | | WO | WO 97/11067 | 3/1997 |
| EP | 0 127 958 | | 12/1984 | WO | WO 97/43633 | 11/1997 |
| EP | 0 284 518 | | 9/1988 | WO | WO 98/19159 | 5/1998 |
| EP | 0 286 118 | | 10/1988 | WO | WO 98/24358 | 6/1998 |
| EP | 0 291 130 | | 11/1988 | WO | WO 98/38906 | 9/1998 |
| EP | 0 313 951 | | 5/1989 | WO | WO 99/56613 | 4/1999 |
| EP | 0 320 109 | | 6/1989 | WO | WO 00/13003 | 3/2000 |
| EP | 0 353 328 | | 2/1990 | WO | WO 00/19887 | 4/2000 |
| EP | 0 362 145 | | 4/1990 | WO | WO 00/32098 | 6/2000 |
| EP | 0 390 390 | | 10/1990 | WO | WO 00/33065 | 6/2000 |
| EP | 0 396 788 | | 11/1990 | WO | WO 00/49940 | 8/2000 |
| EP | 0 476 980 | | 3/1992 | WO | WO 00/59373 | 10/2000 |
| EP | 0 534 074 | | 3/1993 | WO | WO 00/74753 | 12/2000 |
| EP | 0 535 898 | | 4/1993 | WO | WO 01/12158 | 2/2001 |
| EP | 0 539 625 | | 5/1993 | WO | WO 01/20019 | 3/2001 |
| EP | 0 563 795 | | 10/1993 | WO | WO 01/20334 | 3/2001 |
| EP | 0 647 849 | | 4/1995 | WO | WO 01/43660 | 6/2001 |
| EP | 0 776 628 | | 6/1997 | WO | WO 01/58348 | 8/2001 |
| EP | 0 817 809 | | 1/1998 | WO | WO 01/68901 | 9/2001 |
| EP | 0 838 230 | | 4/1998 | WO | WO 01/69222 | 9/2001 |
| EP | 0 862 648 | | 9/1998 | WO | WO 01/88524 | 11/2001 |
| EP | 0 885 932 | | 12/1998 | WO | WO 01/88534 | 11/2001 |
| EP | 0 967 788 | | 12/1999 | WO | WO 02/053764 | 7/2002 |
| EP | 0 995 805 | | 4/2000 | WO | WO 02/058537 | 8/2002 |

| | | |
|---|---|---|
| WO | WO 03/063700 | 8/2003 |
| WO | WO 03/082091 | 9/2003 |
| WO | WO 03/101862 | 12/2003 |
| WO | WO 2005/045394 | 5/2005 |
| WO | WO 2005/026689 | 10/2005 |
| WO | WO 2006/017358 | 2/2006 |
| WO | WO 2006/018425 | 2/2006 |
| WO | WO 2006/105146 | 10/2006 |
| WO | WO 2007/114943 | 10/2007 |

OTHER PUBLICATIONS

Bellucci et al. Jan. 1986. Electrochemical behaviour of graphite-epoxy composite materials (GECM) in aqueous salt solutions, Journal of Applied Electrochemistry, 16(1):15-22.
Bobbioni-Harsch et al. 1993. Lifespan of subcutaneous glucose sensors and their performances during dynamic glycaemia changes in rats, J. Biomed. Eng. 15:457-463.
Davies, et al. 1992. Polymer membranes in clinical sensor applications. I. An overview of membrane function, Biomaterials, 13(14):971-978.
Heller, A. 1992. Electrical Connection of Enzyme Redox Centers to Electrodes. J. Phys. Chem. 96:3579-3587.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Kawagoe et al. 1991. Enzyme-modified organic conducting salt microelectrode, Anal. Chem. 63:2961-2965.
Maidan et al. 1992. Elimination of Electrooxidizable Interferent-Produced Currents in Amperometric Biosensors, Analytical Chemistry, 64:2889-2896.
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'- bipyridine)chloroosmium(+/2+) complexed poly(1-vinylimidazole) films, Analytical Chemistry, 65:3512-3517.
Poitout, et al. 1991. In Vitro and In Vivo Evaluation in Dogs of a Miniaturized Glucose Sensor, ASAIO Transactions, 37:M298-M300.
Reach et al. 1992. Can continuous glucose monitoring be used for the treatment of diabetes? Analytical Chemistry 64(5):381-386.
Sakakida et al. 1993. Ferrocene-Mediated Needle Type Glucose Sensor Covered with Newly Designed Biocompatible Membran, Sensors and Actuators B 13-14:319-322.
Shichiri et al. 1989. Membrane Design for Extending the Long-Life of an Implantable Glucose Sensor. Diab. Nutr. Metab. 2:309-313.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Office Action dated May 26, 2009 in U.S. Appl. No. 09/447,227.
Office Action dated Feb. 4, 2009 in U.S. Appl. No. 11/021,046.
Office Action dated Jun. 6, 2005 in U.S. Appl. No. 10/646,333.
Office Action dated Feb. 24, 2006 in U.S. Appl. No. 10/646,333.
Office Action dated Mar. 5, 2009 in U.S. Appl. No. 10/896,637.
Office Action dated Jul. 20, 2009 in U.S. Appl. No. 10/896,637.
Office Action dated Jan. 22, 2009 in U.S. Appl. No. 11/692,154.
Office Action dated Jul. 8, 2009 in U.S. Appl. No. 11/692,154.
Office Action dated Mar. 16, 2009 in U.S. Appl. No. 10/838,909.
Office Action dated Jun. 23, 2009 in U.S. Appl. No. 10/885,476.
Office Action dated May 26, 2009 in U.S. Appl. No. 11/077,759.
Office Action dated Apr. 6, 2009 in U.S. Appl. No. 11/077,883.
Office Action dated Jan. 26, 2009 in U.S. Appl. No. 11/078,230.
Office Action dated Mar. 5, 2009 in U.S. Appl. No. 11/078,232.
Office Action dated Jul. 21, 2009 in U.S. Appl. No. 11/078,232.
Office Action dated Feb. 10, 2009 in U.S. Appl. No. 11/077,713.
Office Action dated Apr. 16, 2009 in U.S. Appl. No. 11/077,714.
Office Action dated Mar. 11, 2009 in U.S. Appl. No. 11/077,643.
Office Action dated Jun. 22, 2009 in U.S. Appl. No. 11/360,262.
Office Action dated Feb. 23, 2009 in U.S. Appl. No. 11/439,630.
Office Action dated Jul. 21, 2009 in U.S. Appl. No. 11/157,365.
Office Action dated Jun. 30, 2008 in U.S. Appl. No. 11/360,252.
Office Action dated Jan. 29, 2009 in U.S. Appl. No. 11/360,252.
Office Action dated Jul. 23, 2009 in U.S. Appl. No. 11/360,252.
Office Action dated Jun. 29, 2009 in U.S. Appl. No. 11/333,837.
Office Action dated Jun. 15, 2009 in U.S. Appl. No. 11/360,250.
Abel et al. 2002. Biosensors for in vivo glucose measurement: can we cross the experimental stage. Biosens Bioelectron 17:1059-1070.
Armour et al. Dec. 1990. Application of Chronic Intravascular Blood Glucose Sensor in Dogs. Diabetes 39:1519-1526.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Baker et al. 1993. Dynamic concentration challenges for biosensor characterization. Biosensors & Bioelectronics 8:433-441.
Bani Amer, M. M. 2002. An accurate amperometric glucose sensor based glucometer with eliminated cross-sensitivity. J Med Eng Technol 26(5):208-213.
Bard et al. 1980. Electrochemical Methods. John Wiley & Sons, pp. 173-175.
Beach et al. 1999. Subminiature implantable potentiostat and modified commercial telemetry device for remote glucose monitoring. IEEE Transactions on Instrumentation and Measurement 48(6):1239-1245.
Bindra et al. 1989. Pulsed amperometric detection of glucose in biological fluids at a surface-modified gold electrode. Anal Chem 61:2566-2570.
Bindra et al. 1991. Design and In Vitro Studies of a Needle-Type Glucose Senso for Subcutaneous Monitoring. Anal. Chem 63:1692-96.
Bode et al. 1999. Continuous glucose monitoring used to adjust diabetes therapy improves glycosylated heoglobin: A pilot study. Diabetes Research and Clinical Practice 46:183-190.
Bode, B. W. 2000. Clinical utility of the continuous glucose monitoring system. Diabetes Technol Ther, 2(Suppl 1):S35-41.
Bode et al. 2000. Using the continuous glucose monitoring system to improve the management of type 1 diabetes. Diabetes Technology & Therapeutics, 2(Suppl 1):S43-48.
Bott, A. W. 1997. A Comparison of Cyclic Voltammetry and Cyclic Staircase Voltammetry Current Separations 16:1, 23-26.
Bowman, L.; Meindl, J. D. 1986. The packaging of implantable integrated sensors. IEEE Trans Biomed Eng BME33(2):248-255.
Brauker et al. 1995. Neovascularization of synthetic membranes directed by membrane Microarchitecture. J. Biomed Mater Res 29:1517-1524.
Brauker et al. Jun. 27, 1996. Local Inflammatory Response Around Diffusion Chambers Containing Xenografts Transplantation 61(12):1671-1677.
Brauker et al. 1998. Sustained expression of high levels of human factor IX from human cells implanted within an immunoisolation device into athymic rodents. Hum Gene Ther 9:879-888.
Brauker et al. 2001. Unraveling Mysteries at the Biointerface: Molecular Mediator of Inhibition of Blood vessel Formation in the Foreign Body Capsule Revealed. Surfacts Biomaterials 6. 1;5.
Bremer et al. 2001. Benchmark data from the literature for evaluation of new glucose sensing technologies. Diabetes Technology & Therapeutics 3(3):409-418.
Brooks et al. "Development of an on-line glucose sensor for fermentation monitoring," Biosensors, 3:45-56 (1987/88).
Brunner et al. 1998. Validation of home blood glucose meters with respect to clinical and analytical approaches. Diabetes Care 21(4):585-590.
Cai et al. 2004. A wireless, remote query glucose biosensor based on a pH-sensitive polymer. Anal Chem 76(4):4038-4043.
Cox et al. 1985. Accuracy of perceiving blood glucose in IDDM. Diabetes Care 8(6):529-536.
D'Arrigo et al. 2003. Porous-Si based bioreactors for glucose monitoring and drugs production. Proc. of SPIE 4982:178-184.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR® (Catalog).

El-Sa'ad et al. 1990. Moisture Absorption by Epoxy Resins: the Reverse Thermal Effect. Journal of Materials Science 25:3577-3582.

Ernst et al. 2002. Reliable glucose monitoring through the use of microsystem technology. Anal. Bioanal. Chem. 373:758-761.

Fare et al. 1998. Functional characterization of a conducting polymer-based immunoassay system. Biosensors & Bioelectronics 13(3-4):459-470.

Feldman et al. 2003. A continuous glucose sensor based on wired enzyme technology—results from a 3-day trial in patients with type 1 diabetes. Diabetes Technol Ther 5(5):769-779.

Fischer et al. 1989. Oxygen Tension at the Subcutaneous Implantation Site of Glucose Sensors. Biomed. Biochem 11/12:965-972.

Frohnauer et al. 2001. Graphical human insulin time-activity profiles using standardized definitions. Diabetes Technology & Therapeutics 3(3):419-429.

Frost et al. 2002. Implantable chemical sensors for real-time clinical monitoring: Progress and challenges. Current Opinion in Chemical Biology 6:633-641.

Garg et al. 2004. Improved Glucose Excursions Using an Implantable Real-Time continuous Glucose Sensor in Adults with Type I Diabetes. Diabetes Care 27:734-738.

Geller et al. 1997. Use of an immunoisolation device for cell transplantation and tumor immunotherapy. Ann NY Acad Sci 831:438-451.

Gerritsen et al. 1999. Performance of subcutaneously implanted glucose sensors for continuous monitoring. The Netherlands Journal of Medicine 54:167-179.

Gerritsen et al. 2001. Influence of inflammatory cells and serum on the performance of implantable glucose sensors. J Biomed Mater Res 54:69-75.

Gerritsen, M. 2000. Problems associated with subcutaneously implanted glucose sensors. Diabetes Care 23(2):143-145.

Gilligan et al. 2004, Feasibility of continuous long-term glucose monitoring from a subcutaneous glucose sensor in humans. Diabetes Technol Ther 6:378-386.

Gilligan et al. 1994. Evaluation of a subcutaneous glucose sensor out to 3 months in a dog model. Diabetes Care 17(8):882-887.

Gough et al. 2000. Immobilized glucose oxidase in implantable glucose sensor technology. Diabetes Technology & Therapeutics 2(3):377-380.

Gross et al. 2000. Efficacy and reliability of the continuous glucose monitoring system. Diabetes Technology & Therapeutics, 2(Suppl 1):S19-26.

Gross et al. 2000. Performance evaluation of the MiniMed® continuous glucose monitoring system during patient home use. Diabetes Technology & Therapeutics 2(1):49-56.

Hall et al. 1998. Electrochemical oxidation of hydrogen peroxide at platinum electrodes. Part II: Effect of potential. Electrochimica Acta 43(14-15):2015-2024.

Hall et al. 1998. Electrochemical oxidation of hydrogen peroxide at platinum electrodes. Part I: An adsorption-controlled mechanism. Electrochimica Acta, 43(5-6):579-588.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Heller, "Electrical wiring of redox enzymes," Acc. Chem. Res., 23:128-134 (1990).

Heller, A. 1999. Implanted electrochemical glucose sensors for the management of diabetes. Annu Rev Biomed Eng 1:153-175.

Heller, A. 2003. Plugging metal connectors into enzymes. Nat Biotechnol 21:631-2.

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hrapovic et al. 2003. Picoamperometric detection of glucose at ultrasmall platinum-based biosensors: preparation and characterization. Anal Chem 75:3308-3315.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116.

Hunter, I., Jones, L., Kanigan, T., Brenan, C., Sanbol, L. Sosnowski, L. 2000. Minimally Invasive Glucose Sensor and Insulin Delivery System. MIT Home Automation and Healthcare Consortium. Progress Report No. 25.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.

Jensen et al. 1997. Fast wave forms for pulsed electrochemical detection of glucose by incorporation of reductive desorption of oxidation products. Analytical Chemistry 69(9):1776-1781.

Jeutter, D. C. 1982. A transcutaneous implanted battery recharging and biotelemeter power switching system. IEEE Trans Biomed Eng 29:314-321.

Johnson et al. 1992. In vivo evaluation of an electroenzymatic glucose sensor implanted in subcutaneous tissue. Biosensors & Bioelectronics, 7:709-714.

Jovanovic, L. 2000. The role of continuous glucose monitoring in gestational diabetes mellitus. Diabetes Technology & Therapeutics, 2 Suppl 1, S67-71.

Kang et al. 2003. In vitro and short-term in vivo characteristics of a Kel-F thin film modified glucose sensor. Anal Sci 19:1481-1486.

Kargol et al. 2001. Studies on the structural properties of porous membranes: measurement of linear dimensions of solutes. Biophys Chem 91:263-271.

Kaufman. 2000. Role of the continuous glucose monitoring system in pediatric patients. Diabetes Technology & Therapeutics 2(1):S-49-S-52.

Kerner et al. "The function of a hydrogen peroxide-detecting electroenzymatic glucose electrode is markedly impaired in human sub-cutaneous tissue and plasma," Biosensors & Bioelectronics, 8:473-482 (1993).

Kiechle, F.L. 2001. The impact of continuous glucose monitoring on hospital point-of-care testing programs. Diabetes Technol Ther 3:647-649.

Koschinsky et al. 1998. New approach to technical and clinical evaluation of devices for self-monitoring of blood glucose. Diabetes Care 11(8): 619-619.

Koschinsky et al. 2001. Sensors for glucose monitoring: Technical and clinical aspects. Diabetes Metab. Res. Rev. 17:113-123.

Kraver et al. 2001. A mixed-signal sensor interface microinstrument. Sensors and Actuators A 91:266-277.

Kruger et al. 2000. Psychological motivation and patient education: A role for continuous glucose monitoring. Diabetes Technology & Therapeutics, 2(Suppl 1):S93-97.

Lee et al. 1999. Effects of pore size, void volume, and pore connectivity on tissue responses. Society for Biomaterials 25th Annual Meeting, 171.

Lerner et al. 1984. An implantable electrochemical glucose sensor. Ann. N. Y. Acad. Sci. 428:263-278.

Leypoldt et al. 1984. Model of a two-substrate enzyme electrode for glucose. Anal. Chem. 56:2896-2904.

Lyman D. 1960. Polyurethanes. I. The Solution Polymerization of Diisocyanates with Ethylene Glycol. J. Polymer Sci XLV:45:49.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Maran et al. 2002. Continuous subcutaneous glucose monitoring in diabetic patients: A multicenter analysis. Diabetes Care 25(2):347-352.

Mar., W. F. 2002. Dealing with the delay. Diabetes Technol Ther 4(1):49-50.

Mastrototaro et al. "An electroenzymatic glucose sensor fabricated on a flexible substrate," Sensors and Actuators B, 5:139-44 (1991).

Mastrototaro et al. 2003. Reproducibility of the continuous glucose monitoring system matches previous reports and the intended use of the product. Diabetes Care 26:256; author reply p. 257.

Mastrototaro, J. J. 2000. The MiniMed continuous glucose monitoring system. Diabetes Technol Ther 2(Suppl 1):S13-8.

Matsumoto et al. 2001. A long-term lifetime amperometric glucose sensor with a perfluorocarbon polymer coating. Biosens Bioelectron 16:271-276.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

McKean, et al. Jul. 7, 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

Miller, A. 1988. Human monocyte/macrophage activation and interleukin 1 generation by biomedical polymers. J Biomed Mater Res 23:713-731.

Miller et al. 1989. In vitro stimulation of fibroblast activity by factors generated from human monocytes activated by biomedical polymers. Journal of J Biomed Mater Res 23:911-930.

Miller et al. 1989. Generation of IL1-like activity in response to biomedical polymer implants: a comparison of in vitro and in vivo models. J Biomed Mater Res 23:1007-1026.

Moatti-Sirat, D et al. 1992. Evaluating in vitro and in vivo the interference of ascorbate and acetaminophen on glucose detection by a needle-type glucose sensor. Biosensors and Bioelectronics 7:345-352.

Moatti-Sirat et al. 1992. Towards continuous glucose monitoring: in vivo evaluation of a miniaturized glucose sensor implanted for several days in rat subcutaneous tissue. Diabetologia 35:224-230.

Moussy et al. 2000. Biomaterials community examines biosensor biocompatibility Diabetes Technol Ther 2:473-477.

Mowery et al. 2000. Preparation and characterization of hydrophobic polymeric films that are thromboresistant via nitric oxide release. Biomaterials 21:9-21.

Myler et al. 2002. Ultra-thin-polysiloxane-film-composite membranes for the optimisation of amperometric oxidase enzyme electrodes. Biosens Bioelectron 17:35-43.

Nam et al. 2000. A novel fabrication method of macroporous biodegradable polymer scaffolds using gas foaming salt as a porogen additive. J Biomed Mater Res 53:1-7.

Ohara et al. 1994. "Wired" enzyme electrodes for amperometric determination of glucose or lactate in the presence of interfering substances. Anal Chem 66:2451-2457.

Okuda et al. 1971. Mutarotase effect on micro determinations of D-glucose and its anomers with β-D-glucose oxidase. Anal Biochem 43:312-315.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Patel et al. 2003. Amperometric glucose sensors based on ferrocene containing polymeric electron transfer systems—a preliminary report. Biosens Bioelectron 18:1073-6.

Phillips and Smith. 1988. Bromedical Applications of Polyurethanes: Implications of Failure Mechanisms. J. Biomat. Appl. 3:202-227.

Pichert et al. 2000. Issues for the coming age of continuous glucose monitoring Diabetes Educ 26(6):969-980.

Pickup et al. "Implantable glucose sensors: choosing the appropriate sensor strategy," Biosensors, 3:335-346 (1987/88).

Pickup et al. "In vivo molecular sensing in diabetes mellitus: an implantable glucose sensor with direct electron transfer," Diabetologia, 32:213-217 (1989).

Pitzer et al. 2001. Detection of hypoglycemia with the GlucoWatch biographer. Diabetes Care 24(5):881-885.

Poitout et al. 1993. A glucose monitoring system for on line estimation in man of blood glucose concentration using a miniaturized glucose sensor implanted in the subcutaneous tissue and a wearable control unit. Diabetologia 36:658-663.

Postlethwaite et al. 1996. Interdigitated array electrode as an alternative to the rotated ring-disk electrode for determination of the reaction products of dioxygen reduction. Analytical Chemistry 68:2951-2958.

Quinn et al. 1997. Biocompatible, glucose-permeable hydrogel for in situ coating of implantable biosensors. Biomaterials 18:1665-1670.

Ratner, B.D. 2002. Reducing capsular thickness and enhancing angiogenesis around implant drug release systems. J Control Release 78:211-218.

Reach et al. 1986. A Method for Evaluating in vivo the Functional Characteristics of Glucose Sensors. Biosensors 2:211-220.

Reach, Gerard. 2001. Letters to the Editor Re: Diabetes Technology & Therapeutics, 2000;2:49-56. Diabetes Technology & Therapeutics 3(1):129-130.

Rebrin et al. "Automated feedback control of subcutaneous glucose concentration in diabetic dogs," Diabetologia, 32:573-76 (1989).

Rhodes et al. 1994. Prediction of pocket-portable and implantable glucose enzyme electrode performance from combined species permeability and digital simulation analysis. Analytical Chemistry 66(9):1520-1529.

Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.

Sansen et al. 1990. A smart sensor for the voltammetric measurement of oxygen or glucose concentrations. Sensors and Actuators B 1:298-302.

Schmidt et al. 1993. Glucose concentration in subcutaneous extracellular space. Diabetes Care 16(5):695-700.

Schoemaker et al. 2003. The SCGM1 system: Subcutaneous continuous glucose monitoring based on microdialysis technique. Diabetes Technology & Therapeutics 5(4):599-608.

Schuler et al. 1999. Modified gas-permeable silicone rubber membranes for covalent immobilisation of enzymes and their use in biosensor development. Analyst 124:1181-1184.

Selam, J. L. 1997. Management of diabetes with glucose sensors and implantable insulin pumps. From the dream of the 60s to the realities of the 90s. ASAIO J, 43:137-142.

Service, R. F. 2002. Can sensors make a home in the body? Science 297:962-3.

Shaw et al. "In vitro testing of a simply constructed, highly stable glucose sensor suitable for implantation in diabetic patients," Biosensors & Bioelectronics, 6:401-406 (1991).

Shichiri et al. 1982. Wearable artificial endocrine pancrease with needle-type glucose sensor. Lancet 2:1129-1131.

Shichiri et al. 1985. Needle-type Glucose Sensor for Wearable Artificial Endocrine Pancreas in Implantable Sensors 197-210.

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Shults et al. 1994. A telemetry-instrumentation system for monitoring multiple subcutaneously implanted glucose sensors. IEEE Transactions on Biomedical Engineering 41(10):937-942.

Sieminski et al. 2000. Biomaterial-microvasculature interactions. Biomaterials 21:2233-2241.

Skyler, J. S. 2000. The economic burden of diabetes and the benefits of improved glycemic control: The potential role of a continuous glucose monitoring system. Diabetes Technology & Therapeutics 2 Suppl 1:S7-12.

Sriyudthsak et al. 1996. Enzyme-epoxy membrane based glucose analyzing system and medical applications. Biosens Bioelectron 11:735-742.

Steil et al. 2003. Determination of plasma glucose during rapid glucose excursions with a subcutaneous glucose sensor. Diabetes Technology & Therapeutics 5(1):27-31.

Sternberg et al. 1988. Study and Development of Multilayer Needle-type Enzyme-based Glucose Microsensors. Biosensors 4:27-40.

Stokes. 1988. Polyether Polyurethanes: Biostable or Not? J. Biomat. Appl. 3:228-259.

Tanenberg et al. 2000. Continuous glucose monitoring system: A new approach to the diagnosis of diabetic gastroparesis. Diabetes Technology & Therapeutics, 2 Suppl 1:S73-80.

Tang et al. 1993. Fibrin(ogen) mediates acute inflammatory responses to biomaterials. J Exp Med 178:2147-2156.

Tang et al. 1995. Inflammatory responses to biomaterials. Am J Clin Pathol 103:466-471.

Tang et al. 1996. Molecular determinants of acute inflammatory responses to biomaterials. J Clin Invest 97:1329-1334.

Tang et al. 1998. Mast cells mediate acute inflammatory responses to implanted biomaterials. Proc Natl Acad Sci U S A 95:8841-8846.

Thome-Duret et al. 1996. Use of a subcutaneous glucose sensor to detect decreases in glucose concentration prior to observation in blood, Anal. Chem. 68:3822-3826.

Thomé-Duret et al. 1998. Continuous glucose monitoring in the free-moving rat. Metabolism, 47:799-803.

Tibell et al. 2001. Survival of macroencapsulated allogeneic parathyroid tissue one year after transplantation in nonimmunosuppressed humans. Cell Transplant 10:591-9.

Tierney et al. 2000. The GlucoWatch® biographer: A frequent, automatic and noninvasive glucose monitor. Ann. Med. 32:632-641.

Tierney et al. 2000. Effect of acetaminophen on the accuracy of glucose measurements obtained with the GlucoWatch biographer. Diabetes Technol Ther 2:199-207.

Trecroci, D. 2002. A Glimpse into the Future—Continuous Monitoring of Glucose with a Microfiber. Diabetes Interview 42-43.

Tse and Gough. 1987. Time-Dependent Inactivation of Immobilized Glucose Oxidase and Catalase. Biotechnol. Bioeng. 29:705-713.

Turner and Pickup, "Diabetes mellitus: biosensors for research and management," *Biosensors*, 1:85-115 (1985).

Updike et al. 1967. The enzyme electrode. Nature, 214:986-988.

Updike et al. 1982. Implanting the glucose enzyme electrode: Problems, progress, and alternative solutions. Diabetes Care, 5(3):207-212.

Updike et al. 1988. Laboratory Evaluation of New Reusable Blood Glucose Sensor. Diabetes Care, 11:801-807.

Updike et al. 1994. Enzymatic glucose sensor: Improved long-term performance in vitro and in vivo. ASAIO Journal, 40(2):157-163.

Updike et al. 2000. A subcutaneous glucose sensor with improved longevity, dynamic range, and stability of calibration. Diabetes Care 23(2):208-214.

Velho et al. 1989. In vitro and in vivo stability of electrode potentials in needle-type glucose sensors. Influence of needle material. Diabetes 38:164-171.

Wagner et al. 1998. Continuous amperometric monitoring of glucose in a brittle diabetic chimpanzee with a miniature subcutaneous electrode. Proc. Natl. Acad. Sci. A, 95:6379-6382.

Wang et al. 1994. Highly Selective Membrane-Free, Mediator-Free Glucose Biosensor. Anal. Chem. 66:3600-3603.

Wang et al. 1997. Improved ruggedness for membrane-based amperometric sensors using a pulsed amperometric method. Anal Chem 69:4482-4489.

Ward et al. 2000. Rise in background current over time in a subcutaneous glucose sensor in the rabbit: Relevance to calibration and accuracy. Biosensors & Bioelectronics, 15:53-61.

Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.

Ward et al. 2002. A new amperometric glucose microsensor: In vitro and short-term in vivo evaluation. Biosensors & Bioelectronics, 17:181-189.

Wientjes, K. J. C. 2000. Development of a glucose sensor for diabetic patients (Ph.D. Thesis).

Wilkins et al. 1995. Glucose monitoring: state of the art and future possibilities. Med Eng Phys 18:273-288.

Wilkins et al. 1995. Integrated implantable device for long-term glucose monitoring. Biosens. Bioelectron 10:485-494.

Wilson et al. 1992. Progress toward the development of an implantable sensor for glucose. Clin. Chem. 38(9):1613-1617.

Wilson et al. 2000. Enzyme-based biosensors for in vivo measurements. Chem. Rev., 100:2693-2704.

Wood, W. et al. Mar. 1990. Hermetic Sealing with Epoxy. Mechanical Engineering 1-3.

Wu et al. 1999. In site electrochemical oxygen generation with an immunoisolation device. Annals New York Academy of Sciences, pp. 105-125.

Yang et al. 1998. Development of needle-type glucose sensor with high selectivity. Science and Actuators B 46:249-256.

Office Action dated Sep. 5, 2006 in U.S. Appl. No. 09/916,711.
Office Action dated Feb. 14, 2006 in U.S. Appl. No. 09/916,711.
Office Action dated Jul. 1, 2005 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Feb. 11, 2004 in U.S. Appl. No. 09/916,711.
Office Action dated Sep. 24, 2003 in U.S. Appl. No. 09/916,711.
Office Action dated Jun. 19, 2008 in U.S. Appl. No. 11/021,162.
IPER for PCT/US02/23903 filed Jul. 26, 2002.
ISR for PCT/US02/23903 filed Jul. 26, 2002.
WO for PCT/US02/23903 filed Jul. 26, 2002.
Office Action dated Dec. 7, 1998 in U.S. Appl. No. 08/811,473.
Office Action dated Jul. 17, 2007 in U.S. Appl. No. 09/447,227.
Office Action dated Mar. 9, 2007 in U.S. Appl. No. 09/447,227.
Office Action dated Aug. 1, 2006 in U.S. Appl. No. 09/447,227.
Office Action dated Apr. 4, 2006 in U.S. Appl. No. 09/447,227.
Office Action dated Sep. 22, 2005 in U.S. Appl. No. 09/447,227.
Office Action dated Nov. 28, 2003 in U.S. Appl. No. 09/447,227.
Office Action dated Jul. 9, 2003 in U.S. Appl. No. 09/447,227.
Office Action dated Jan. 16, 2003 in U.S. Appl. No. 09/447,227.
Office Action dated Jul. 15, 2002 in U.S. Appl. No. 09/447,227.
Office Action dated Jan. 17, 2002 in U.S. Appl. No. 09/447,227.
Office Action dated Aug. 15, 2001 in U.S. Appl. No. 09/447,227.
Office Action dated Jun. 6, 2003 in U.S. Appl. No. 10/646,333.
Office Action dated Sep. 22, 2004 in U.S. Appl. No. 10/646,333.
Office Action dated May 22, 2006 in U.S. Appl. No. 10/896,772.
Office Action dated Dec. 14, 2005 in U.S. Appl. No. 10/896,772.
Office Action dated Jul. 19, 2005 in U.S. Appl. No. 10/896,772.
Office Action dated Jan. 11, 2005 in U.S. Appl. No. 10/896,772.
Office Action dated May 11, 2006 in U.S. Appl. No. 10/897,377.
Office Action dated Oct. 18, 2005 in U.S. Appl. No. 10/897,377.
Office Action dated Feb. 9, 2006 in U.S. Appl. No. 10/897,312.
Office Action dated Jan. 27, 2006 in U.S. Appl. No. 11/007,635.
Office Action mailed May 18, 2007 in U.S. Appl. No. 11/543,707.
Office Action mailed May 23, 2007 in U.S. Appl. No. 11/543,539.
Office Action mailed May 18, 2007 in U.S. Appl. No. 11/543,683.
Office Action mailed Jun. 5, 2007 in U.S. Appl. No. 11/543,734.
Office Action dated May 17, 2007 in U.S. Appl. No. 11/077,759.
Office Action dated Oct. 31, 2006 in U.S. Appl. No. 11/077,715.
Office Action dated Apr. 10, 2007 in U.S. Appl. No. 11/077,715.
Office Action dated Jul. 26, 2007 in U.S. Appl. No. 11/077,715.
Office Action dated Jul. 27, 2007 in U.S. Appl. 11/077,714.
Office Action dated Apr. 10, 2007 in U.S. Appl. 11/077,714.
Office Action dated Oct. 11, 2006 in U.S. Appl. 11/077,714.
Office Action dated Jan. 30, 2007 in U.S. Appl. No. 11/077,763.

Aussedat et al. 1997. A user-friendly method for calibrating a subcutaneous glucose sensor-based hypoglycaemic alarm. Biosensors & Bioelectronics 12(11):1061-1071.

Cass et al. "Ferrocene-mediated enzyme electrodes for amperometric determination of glucose," Anal. Chem., 36:667-71 (1984).

Chia et al. 2004. Glucose sensors: toward closed loop insulin delivery. Endocrinol Metab Clin North Am 33:175-95.

Clark et al. 1987. Configurational cyclic voltammetry: increasing the specificity and reliablity of implanted electrodes, IEEE/Ninth Annual Conference of the Engineering in Medicine and Biollogy Society, pp. 0782-0783.

El Deheigy et al. 1986. Optimization of an implantable coated wire glucose sensor. J. Biomed Eng. 8: 121-129.

Fischer et al. 1995. Hypoglycaemia-warning by means of subcutaneous electrochemical glucose sensors: an animal study, Horm. Metab. Rese. 27:53.

Godsland et al. 2001. Maximizing the Success Rate of Minimal Model Insulin Sensitivity Measurement in Humans: The Importance of Basal Glucose Levels. The Biochemical Society and the Medical Research Society, 1-9.

Guo et al., Modification of cellulose acetate ultrafiltration membrane by gamma ray radiation, Shuichuli Jishi Bianji Weiyuanhui, 23(6):315-318, 1998 (Abstract only).
Harrison et al. 1988. Characterization of perfluorosulfonic acid polymer coated enzyme electrodes and a miniaturized integrated potentiostat for glucose analysis in whole blood. Anal. Chem. 60:2002-2007.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes Care*, 17(5): 387-396.
Johnson (1991). "Reproducible electrodeposition of biomolecules for the fabrication of miniature electroenzymatic biosensors," Sensors and Actuators B, 5:85-89.
Moatti-Sirat et al., Reduction of acetaminophen interference in glucose sensors by a composite Nafion membrane: demonstration in rats and man, Diabetologia 37(6):610-616, Jun. 1994.
Morff et al. 1990. Microfabrication of reproducible, economical, electroenzymatic glucose sensors, Annual International Conference of the IEEE Engineering in Medicine and Biology Society, 12(2):0483-0484.
Pishko et al. "Amperometric glucose microelectrodes prepared through immobilization of glucose oxidase in redox hydrogels," Anal. Chem., 63:2268-72 (1991).
Shichiri et al. 1983. Glycaemic Control in Pancreatectomized Dogs with a Wearable Artificial Endocrine Pancreas. Diabetologia 24:179-184.
Sokol et al. 1980, Immobilized-enzyme rate-determination method for glucose analysis, Clin. Chem. 26(1):89-92.
Thome et al. 1995. Can the decrease in subcutaneous glucose concentration precede the decrease in blood glucose level? Proposition for a push-pull kinetics hypothesis, Horm. Metab. Res. 27:53.
Thomé-Duret et al. 1996. Modification of the sensitivity of glucose sensor implanted into subcutaneous tissue. Diabetes Metabolism, 22:174-178.
Thompson et al., In Vivo Probes: Problems and Perspectives, Department of Chemistry, University of Toronto, Canada, pp. 255-261, 1986.
Updike et al. 1979. Continuous glucose monitor based on an immobilized enzyme electrode detector. J Lab Clin Med, 93(4):518-527.
Updike et al. 1997. Principles of long-term fully impleated sensors with emphasis on radiotelemetric monitoring of blood glucose form inside a subcutaneous foreign body capsule (FBC). In Fraser, ed., Biosensors in the Body. New York. John Wiley & Sons, pp. 117-137.
Ward et al. 1999. Assessment of chronically implanted subcutaneous glucose sensors in dogs: The effect of surrounding fluid masses. ASAIO Journal, 45:555-561.
Yang et al (1996). "A glucose biosensor based on an oxygen electrode: In-vitro performances in a model buffer solution and in blood plasma," Biomedical Instrumentation & Technology, 30:55-61.
Zhang et al (1993). Electrochemical oxidation of H2O2 on Pt and Pt + Ir electrodes in physiological buffer and its applicability to H2O2-based biosensors. J. Electroanal. Chem., 345:253-271.
Zhu et al. (1994). "Fabrication and characterization of glucose sensors based on a microarray H2O2 electrode." Biosensors & Bioelectronics, 9: 295-300.
Office Action dated Dec. 11, 2008 in U.S. Appl. No. 09/447,227.
Office Action dated Jun. 12, 2008 in U.S. Appl. No. 09/447,227.
Office Action dated Jan. 23, 2008 in U.S. Appl. No. 09/447,227.
Office Action dated Dec. 26, 2007 in U.S. Appl. No. 11/021,046.
Office Action dated Jun. 23, 2008 in U.S. Appl. No. 11/021,046.
Office Action dated Mar. 7, 2007 in U.S. Appl. No. 10/153,356.
Office Action dated Aug. 29, 2006 in U.S. Appl. No. 10/153,356.
Office Action dated Mar. 10, 2006 in U.S. Appl. No. 10/153,356.
Office Action dated Oct. 6, 2005 in U.S. Appl. No. 10/153,356.
Office Action dated Mar. 15, 2005 in U.S. Appl. No. 10/153,356.
Office Action dated Aug. 12, 2004 in U.S. Appl. No. 10/153,356.
Office Action dated Feb. 17, 2004 in U.S. Appl. No. 10/153,356.
Office Action dated Oct. 8, 2008 in U.S. Appl. No. 10/896,627.
Office Action dated Dec. 12, 2007 in U.S. Appl. No. 11/543,707.
Office Action mailed Dec. 12, 2007 in U.S. Appl. No. 11/543,539.
Office Action mailed Dec. 12, 2007 in U.S. Appl. No. 11/543,683.
Office Action mailed Dec. 17, 2007 in U.S. Appl. No. 11/543,734.
Office Action dated Jan. 15, 2008 in U.S. Appl. No. 11/034,344.
Office Action dated Nov. 1, 2007 in U.S. Appl. No. 11/034,343.
Office Action dated Jul. 10, 2008 in U.S. Appl. No. 11/034,343.
Office Action dated Dec. 30, 2008 in U.S. Appl. No. 11/034,343.
Office Action dated Sep. 21, 2007 in U.S. Appl. No. 10/838,912.
Office Action dated Mar. 24, 2008 in U.S. Appl. No. 10/838,912.
Office Action dated Jul. 16, 2008 in U.S. Appl. No. 10/838,912.
Office Action in U.S. Appl. No. 10/838,909 mailed Jun. 5, 2008.
Office Action dated Dec. 15, 2008 in U.S. Appl. No. 10/838,658.
Office Action dated Dec. 24, 2008 in U.S. Appl. No. 10/885,476.
Office Action dated Mar. 31, 2008 in U.S. Appl. No. 11/077,759.
Office Action dated Jul. 10, 2008 in U.S. Appl. No. 11/077,759.
Office Action dated Jan. 28, 2008 in U.S. Appl. No. 11/077,715.
Office Action dated May 12, 2008 in U.S. Appl. No. 11/077,715.
Office Action dated Nov. 12, 2008, in U.S. Appl. No. 11/077,715.
Office Action dated Oct. 9, 2007 in U.S. Appl. No. 11/077,883.
Office Action dated Jun. 24, 2008 in U.S. Appl. No. 11/077,883.
Office Action dated Sep. 18, 2008 in U.S. Appl. No. 11/077,883.
Office Action dated Jun. 30, 2008 in U.S. Appl. No. 11/078,230.
Office Action dated Sep. 18, 2007 in U.S. Appl. No. 11/078,230.
Office Action dated Sep. 5, 2008 in U.S. Appl. No. 11/078,230.
Office Action dated May 5, 2008 in U.S. Appl. No. 11/078,232.
Office Action dated Nov. 12, 2008 in U.S. Appl. No. 11/078,232.
Office Action dated May 5, 2008 in U.S. Appl. No. 11/077,713.
Office Action dated Jun. 27, 2008 in U.S. Appl. No. 11/077,693.
Office Action dated Dec. 26, 2008 in U.S. Appl. No. 11/077,693.
Office Action dated Jan. 10, 2008 in U.S. Appl. 11/077,714.
Office Action dated Sep. 16, 2008 in U.S. Appl. 11/077,714.
Office Action dated Apr. 21, 2008 in U.S. Appl. No. 11/077,643.
Office Action dated Oct. 1, 2008 in U.S. Appl. No. 11/077,643.
Office Action dated Jul. 26, 2007 in U.S. Appl. No. 11/411,656.
Office Action dated Sep. 18, 2008 in U.S. Appl. No. 11/439,630.
Office Action dated Jan. 3, 2008 in U.S. Appl. No. 11/157,746.
Office Action dated May 1, 2008 in U.S. Appl. No. 11/157,746.
Office Action dated Jun. 26, 2008 in U.S. Appl. No. 11/157,365.
Office Action dated Jan. 7, 2009 in U.S. Appl. No. 11/157,365.
Office Action dated Aug. 11, 2008 in U.S. Appl. No. 11/360,819.
Office Action dated Dec. 26, 2008 in U.S. Appl. No. 11/360,819.
Office Action dated Nov. 28, 2008 in U.S. Appl. No. 11/333,837.
Office Action dated Nov. 28, 2008 in U.S. Appl. No. 11/360,250.
Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Alan. Chem. 64(18):2160-2163.
Abel et al. 1984. Experience with an implantable glucose sensor as a prerequisite of an artifical beta cell, Biomed. Biochim. Acta 43(5):577-584.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers. com Nov. 7, 2006 http://www. Answers.com/topic/xenogenic.
Bailey et al. 2007. Reduction in hemoglobin A1c with real-time continuous glucose monitoring: results from a 12-week observational study. Diabetes Technology & Therapeutics 9(3):203-210.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bisenberger et al. 1995. A triple-step potential waveform at enzyme multisensors with thick-film gold electrodes for detection of glucose and sucrose. Sensors and Actuators, B 28:181-189.

Bland et al. 1990. A note on the use of the intraclass correlation coefficient in the evaluation of agreement between two methods of measurement. Comput. Biol. Med. 20(5):337-340.

Boedeker Plastics, Inc. 2009. Polyethylene Specifications Data Sheet, http://www.boedeker.com/polye_p.htm [Aug. 19, 2009 3:36:33 PM].

Boland et al. 2001. Limitations of conventional methods of self-monitoring of blood glucose. Diabetes Care 24(11):1858-1862.

Braunwald, 2008. Biomarkers in heart failure. *N. Engl. J. Med.*, 358: 2148-2159.

Bruckel et al. 1989. In vivo measurement of subcutaneous glucose concentrations with an enzymatic glucose sensor and a wick method. Klin Wochenschr 67:491-495.

Campanella et al. 1993. Biosensor for direct determination of glucose and lactate in undiluted biological fluids. Biosensors & Bioelectronics 8:307-314.

Candas et al (1994). "An adaptive plasma glucose controller based on a nonlinear insulin/glucose model." *IEEE Transactions on Biomedical Engineering*, 41(2): 116-124.

Cassidy et al., Apr. 1993. Novel electrochemical device for the detection of cholesterol or glucose, Analyst, 118:415-418.

Chase et al. 2001. Continuous subcutaneous glucose monitoring in children with type 1 diabetes. Pediatrics 107:222-226.

Chatterjee et al. 1997. Poly(ether Urethane) and poly(ether urethane urea) membranes with high $H_2S/CH_4$ selectivity, Journal of Membrane Science 135:99-106.

Ciba® Irgacure 2959 Photoinitiator Product Description, Ciba Specialty Chemicals Inc., Basel, Switzerland.

Claremont et al. 1986. Subcutaneous implantation of a ferrocene-mediated glucose sensor in pigs. Diabetologia 29:817-821.

Claremont et al. Jul. 1986. Potentially-impintable, ferrocene-mediated glucose sensor. J. Biomed. Eng. 8:272-274.

Clark et al., 1981. One-minute electrochemical enzymic assay for cholesterol in biological materials, Clin. Chem. 27(12):1978-1982.

Clark et al. 1988. Long-term stability of electroenzymatic glucose sensors implanted in mice. Trans Am Soc Artif Intern Organs 34:259-265.

CLSI. Performance metrics for continuous interstitial glucose monitoring; approved guideline, CLSI document POCT05-A. Wayne, PA: Clinical and Laboratory Standards Institute: 2008 28(33), 72 pp.

Colangelo et al. 1967. Corrosion rate measurements in vivo, Journal of Biomedical Materials Research, 1:405-414.

Colowick et al. 1976. Methods in Enzymlology, vol. XLIV, Immobilized Enzymes. New York: Academic Press.

Csoregi et al., 1994. Design, characterization, and one-point in vivo calibration of a subcutaneously implanted glucose electrode. Anal Chem. 66(19):3131-3138.

Danielsson et al. 1988. Enzyme thermistors, Methods in Enzymology, 137:181-197.

Dassau et al., In silico evaluation platform for artifical pancreatic β-cell development-a dynamic simulator for closed loop control with hardware-in-the-loop, Diabetes Technology & Therapeutics, 11(3):1-8, 2009.

Davis et al. 1983. Bioelectrochemical fuel cell and sensor based on a quinoprotein, alcohol dehydrogenase. *Enzyme Microb. Technol.*, vol. 5, September, 383-388.

Durliat et al. 1976. Spectrophotometric and electrochemical determinations of L(+)-lactate in blood by use of lactate dehydrogenase from yeast, Clin. Chem. 22(11):1802-1805.

Edwards Lifesciences. Accuracy for your and your patients. Marketing materials, 4 pp. 2002.

El-Khatib et al. 2007. Adaptive closed-loop control provides blood-glucose regulation using dual subcutaneous insulin and glucagon infusion in diabetic swine, Journal of Diabetes Science and Technology, 1(2):181-192.

Fahy et al., An analysis: hyperglycemic intensive care patients need continuous glocuse monitoring—easier said than done, Journal of Diabetese Science and Technology, 2(2):201-204, Mar. 2008.

Fischer et al. 1987. Assessment of subcutaneous glucose concentration: validation of the wick technique as a reference for implanted electrochemical sensors in normal and diabetic dogs, Diabetologia 30:940-945.

Freedman et al. 1991. Statistics, Second Edition, W.W. Norton & Company, p. 74.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA@ blood chemistry monitor for glucose in healthy and diabetic volunteers, Journal of Diabetese Science and Technology, 2(2):182-193, Mar. 2008.

Gao et al. 1989. Determination of Interfacial parameters of cellulose acetate membrane materials by HPLC, *J. Liquid Chromatography*, VI. 12, n. 11, 2083-2092.

Gouda et al., Jul. 4, 2003. Thermal inactiviation of glucose oxidase, The Journal of Biological Chemistry, 278(27):24324-24333.

Gough et al. 2003. Frequency characterization of blood glucose dynamics. Annals of Biomedical Engineering 31:91-97.

Guerci et al., Clinical performance of CGMS in type 1 diabetic patents treated by continuous subcutaneous insulin infusion using insulin analogs, Diabetes Care, 26:582-589, 2003.

Hamilton Syringe Selection Guide. 2006. Syringe Selection. www.hamiltoncompany.com.

Hoel, Paul G. 1976. Elementary Statistics, Fourth Edition. John Wiley & Sons, Inc.. pp. 113-114.

http://www.merriam-webster.com/dictionary, definition for "aberrant," Aug. 19, 2008, p. 1.

Huang et al. A 0.5mV passive telemetry IC for biomedical applications. Swiss Federal Institute of Technology. 4 pp.

Kacaniklic May-Jun. 1994. Electroanalysis, 6(5-6):381-390.

Kamath et al. Calibration of a continuous glucose monitor: effect of glucose rate of change, Eighth Annual Diabetes Technology Meeting, Nov. 13-15, 2008, p. A88.

Kaufman et al. 2001. A pilot study of the continuous glucose monitoring system. Diabetes Care 24(12):2030-2034.

Keedy et al. 1991. Determination of urate in undiluted whole blood by enzyme electrode. *Biosensors & Bioelectronics*, 6: 491-499.

Kerner et al. 1988. A potentially implantable enzyme electrode for amperometric measurement of glucose, Horm Metab Res Suppl. 20:8-13.

Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kurtz et al. 2005. Recommendations for blood pressure measurement in humans and experimental animals, Part 2: Blood pressure measurement in experimental animals, A statement for professionals from the subcommittee of professional and public education of.

Ladd et al., Structure Determination by X-ray Crystallography, 3rd ed. Plenum, 1996, Ch. 1, pp. xxi-xxiv and 1-58.

Lehmann et al. May 1994. Retrospective valication of a physiological model of glucose-iunsulin interaaction in tyhpe 1 diabetes mellitus, Med. Eng. Phys. 16:193-202.

Lewandowski et al. 1988. Evaluation of a miniature blood glucose sensor. Trans Am Soc Artif Intern Organs 34:255-258.

Linke et al. 1994. Amperometric biosensor for in vivo glucose sensing based on glucose oxidase immobilized in a redox hydrogel. Biosensors & Bioelectronics 9:151-158.
Lowe, 1984. Biosensors, Trends in Biotechnology, 2(3):59-65.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Lyandres et al. (2008). Progress toward an in vivo surface-enhanced raman spectroscopy glucose sensor. *Diabetes Technology & Therapeutics*, 10(4): 257-265.
Marena et al. 1993. The artifical endocrine pancreas in clinical practice and research. Panminerva Medica 35(2):67-74.
Mascini et al. 1989. Glucose electrochemical probe with extended linearity for whole blood. *J Pharm Biomed Anal* 7(12): 1507-1512.
Matsumoto et al. 1998. A micro-planar amperometeric glucose sensor unsusceptible to interference species. Sensors and Actuators B 49:68-72.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diab. Thechnol. & Therapeut., 10:149-159.
Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.
Merriam-Webster Online Dictionary. The term "nominal." http://www.m-w.com/dictionary/nominal.
Meyerhoff et al. 1992. On line continuous monitoring of subcutaneous tissue glucose in men by combining portable glucosensor with microdialysis. Diabetologia 35:1087-1092.
Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.
Muslu. 1991. Trickling filter performance. Apllied Biochemistry and Biotechnology 37:211-224.
Nafion® 117 Solution Product Description, Product No. 70160, Sigma-Aldrich Corp., St. Louis, MO.
Oxford English Dictionary Online. Definition of "impending". http://www.askoxford.com/results/?view=dev dict&field-12668446 Impending& branch= Jan. 11, 2010.
Park et al. 2002. Gas separation properties of polysiloxane/polyether mixed soft segment urethane urea membranes, *J. Membrane Science*, 204: 257-269.
Peacock et al. 2008. Cardiac troponin and outcome in acute heart failure. N. Engl. J. Med., 358: 2117-2126.
Pegoraro et al. 1995. Gas transport properties of siloxane polyurethanes, Journal of Applied Polymer Science, 57:421-429.
Pfeiffer et al. 1992. On line continuous monitoring of subcutaneous tissue glucose is feasible by combining portable glucosensor with microdialysis. Horm. Metab. Res. 25:121-124.
Pfeiffer, E.F. 1990. The glucose sensor: the missing link in diabetes therapy, Horm Metab Res Suppl. 24:154-164.
Pickup et al. 1989. Potentially-implantable, amperometric glucose sensors with mediated electron transfer: improving the operating stability. Biosensors 4:109-119.
Pickup et al. 1993. Developing glucose sensors for in vivo use. Elsevier Science Publishers Ltd (UK), TIBTECH vol. 11: 285-291.
Pinner et al., Cross-linking of cellulose acetate by ionizing radiation, Nature, vol. 184, 1303-1304, Oct. 24, 1959.
Poitout et al. 1994. Development of a glucose sensor for glucose monitoring in man: the disposable implant concept. Clinical Materials 15:241-246.
Prabhu et al. 1981. Electrochemical studies of hydrogen peroxide at a platinum disc electrode, Electrochimica Acta 26(6):725-729.

Quinn et al. 1995. Kinetics of glucose delivery to subcutaneous tissue in rats measured with 0.3-mm amperometric microsensors. The American Physiological Society E155-E161.
Rabah et al., 1991. Electrochemical wear of graphite anodes during electrolysis of brine, Carbon, 29(2):165-171.
Reach, G. 2001. Which threshold to detect hypoglycemia? Value of receiver-operator curve analysis to find a compromise between sensitivity and specificity. Diabetes Care 24(5):803-804.
Rebrin et al. 1992. Subcutaenous glucose monitoring by means of electrochemical sensors: fiction or reality? J. Biomed. Eng. 14:33-40.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rigla et al. 2008. Real-time continuous glucose monitoring together with telemedical assitance improves glycemic control and glucose stability in pump-treated patients. Diab. Thechnol. & Therapeut., 10: 194-199.
Rivers et al., Central venous oxygen saturation monitoring in the critically ill patient, Current Opinion in Critical Care, 7:204-211, 2001.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Salardi et al. 2002. The glucose area under the profiles obtained with continuous glucose monitoring system relationships with HbA1c in pediatric type 1 diabetic patients. Diabetes Care 25(10):1840-1844.
San Diego Plastics, Inc. 2009. Polyethylene Data Sheet, http://www.sdplastics.com/polyeth.html.
Schmidtke et al., Measurement and modeling of the transient difference between blood and subcutaneous glucose concentrations in the rat after injection of insulin. *Proc Natl Aced Sci U S A* 1998, 95, 294-299.
Schoonen et al. 1990 Development of a potentially wearable glucose sensor for patients with diabetes mellitus: design and in-vitro evaluation. Biosensors & Bioelectronics 5:37-46.
Service et al. 1970. Mean amplitude of glycemic excursions, a measure of diabetic instability. Diabetes, 19: 644-655.
Service et al. 1987. Measurements of glucose control. Diabetes Care, 10: 225-237.
Sharkawy et al. 1996. Engineering the tissue which encapsulates subcutaneous implants. I. Diffusion properties, J Biomed Mater Res, 37:401-412.
Slater-Maclean et al. 2008. Accuracy of glycemic measurements in the critically ill. Diab. Thechnol. & Therapeut., 10:169-177.
Stern et al., 1957. Electrochemical polarization: 1. A theoretical analysis of the shape of polarization curves, Journal of the Electrochemical Society, 104(1):56-63.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrance Science, 75(93-105).
Tatsuma et al. 1991. Oxidase/peroxidase bilayer-modified electrodes as sensors for lactate, pyruvate, cholesteral and uric acid, Analytica Chimica Acta, 242:85-89.
Torjman et al., Glucose monitoring in acute care: technologies on the horizon, Journal of Deabetes Science and Technology, 2(2):178-181, Mar. 2008.
Turner et al. 1984. Carbon Monoxide: Acceptor Oxidoreductase from *Pseudomonas* Thermocarboxydovorans Strain C2 and its use in a Carbon Monoxide Sensor. Analytica Chimica Acta, 163: 161-174.
Unger et al. 2004. Glucose control in the hospitalized patient. Emerg Med 36(9):12-18.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Van den Berghe 2004. Tight blood glucose control with insulin in "real-life" intensive care. Mayo Clin Proc 79(8):977-978.

Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.
Yamasaki et al. 1989. Direct measurement of whole blood glucose by a needle-type sensor. Clinica Chimica Acta. 93:93-98.
Yamasaki, Yoshimitsu. Sep. 1984. The development of a needle-type glucose sensor for wearable artificial endocrine pancreas. Medical Journal of Osaka University 35(1-2):25-34.
Yang, et al. 2004. A Comparison of Physical Properties and Fuel Cell Performance of Nafion and Zirconium Phosphate/Nafion Composite Membranes. Journal of Membrane Science 237:145-161.
Ye et al. 1993. High Current Density 'Wired' Quinoprotein Glucose Dehydrogenase Electrode. Anal. Chem. 65:238-241.
Zamzow et al. Development and evaluation of a wearable blood glucose monitor. pp. M588-M591, 1990.
Zethelius et al. 2008. Use of multiple biomarkers to improve the prediction of death from cardiovascular causes. N. Engl. J. Med., 358: 2107-2116.
Zhang et al. 1994. Elimination of the acetaminophen interference in an implantable glucose sensor. Analytical Chemistry 66(7):1183-1188.
Zhu et al. 2002. Planar amperometric glucose sensor based on glucose oxidase immobilized by chitosan film on prussian blue layer. Sensors, 2:127-136.
Office Action dated Aug. 19, 2009 in U.S. Appl. No. 11/021,046.
Office Action dated Jul. 23, 2009 in U.S. Appl. No. 11/404,481.
Office Action dated Dec. 10, 2008 in U.S. Appl. No. 11/280,672.
Office Action dated Jun. 2, 2009 in U.S. Appl. No. 11/280,672.
Office Action dated Oct. 29, 2009 in U.S. Appl. No. 11/280,672.
Office Action dated Sep. 23, 2005 in U.S. Appl. No. 10/896,639.
Office Action dated Apr. 6, 2006 in U.S. Appl. No. 10/896,639.
Office Action dated Aug. 22, 2006 in U.S. Appl. No. 10/896,639.
Office Action dated Apr. 11, 2007 in U.S. Appl. No. 10/896,639.
Office Action dated Oct. 5, 2007 in U.S. Appl. No. 10/896,639.
Office Action dated Dec. 3, 2008 in U.S. Appl. No. 11/675,063.
Office Action dated Jun. 10, 2009 in U.S. Appl. No. 11/675,063.
Office Action dated Dec. 6, 2005 in U.S. Appl. No. 10/695,636.
Office Action dated May 22, 2006 in U.S. Appl. No. 10/695,636.
Office Action dated Mar. 14, 2007 in U.S. Appl. No. 10/695,636.
Office Action dated Sep. 12, 2008 in U.S. Appl. No. 10/991,353.
Office Action dated Mar. 4, 2009 in U.S. Appl. No. 10/991,353.
Office Action dated Jul. 31, 2009 in U.S. Appl. No. 10/991,353.
Office Action dated Jul. 30, 2009 in U.S. Appl. No. 10/838,658.
Office Action dated Nov. 12, 2009 in U.S. Appl. No. 11/077,883.
Office Action dated Sep. 2, 2009 in U.S. Appl. No. 11/077,713.
Office Action dated Sep. 4, 2009 in U.S. Appl. No. 11/077,693.
Office Action dated Sep. 2, 2009 in U.S. Appl. No. 11/078,072.
Office Action dated Aug. 21, 2009 in U.S. Appl. No. 11/360,299.
Office Action dated Sep. 2, 2009 in U.S. Appl. No. 11/439,630.
Office Action dated Jun. 26, 2008 in U.S. Appl. No. 11/335,879.
Office Action dated Jan. 13, 2009 in U.S. Appl. No. 11/335,879.
Office Action dated Jun. 16, 2009 in U.S. Appl. No. 11/335,879.
Office Action dated Oct. 29, 2009 in U.S. Appl. No. 11/360,819.
Office Action dated Jan. 23, 2009 in U.S. Appl. No. 11/404,417.
Office Action dated Nov. 20, 2009 in U.S. Appl. No. 11/360,250.
Jaffari et al. 1995. Recent advances in amperometric glucose biosensors for in vivo monitoring, Physiol. Meas. 16: 1-15.
Jobst et al., (1996) Thin-Film Microbiosensors for Glucose-Lactate Monitoring, Anal Chem. 8(18): 3173-3179.
Jovanovic et al. 1997. The Thermogravimetric analysis of some polysiloxanes. Polym Degrad Stability 61: 87-93.
Moussy et al. 1993. Performance of subcutaneously implanted needle-type glucose sensors employing a novel trilayer coating, Anal Chem. 85: 2072-2077.
Moussy, Francis (Nov. 2002) Implantable Glucose Sensor: Progress and Problems, Sensors, 1:270-273.
Samuels, M.P. 2004. The effects of flight and altitude. Arch Dis Child. 89: 448-455.
Ward et al. 2004. A wire-based dual-analyte sensor for Glucose and Lactate: In Vitro and In Vivo Evaluation, Diab Tedh Therapeut. 6(3): 389-401.
Electronic File History for U.S. Appl. No. 09/916,711, filed Jul. 27, 2001 (Abandoned) containing Office Action(s) dated Sep. 24, 2003, Feb. 11, 2004, Jul. 23, 2004, Dec. 23, 2004, Jul. 1, 2005, Sep. 23, 2005 and Feb. 14, 2006 and Applicant(s) Response(s) filed Nov. 24, 2003, Apr. 26, 2004, Oct. 18, 2004, Nov. 22, 2004, Mar. 25, 2005, Sep. 7, 2005, Sep. 30, 2005 and Jun. 15, 2006.
Electronic File History for U.S. Serial No. Electronic File History for U.S. Appl. No. 11/021,162, filed Dec. 22, 2004 (U.S. Patent 7,471,972, issued Dec. 30, 2008) containing Office Action(s) dated Jun. 19, 2008 and Sep. 24, 2008 and Applicant(s) Response(s) filed Jan. 16, 2007 and Sep. 15, 2008.
Ciba® Irgacure® 2959 Photoinitiator, Product Description. Apr. 2, 1998. Ciba Specialty Chemicals Inc., Basel, Switzerland. 3 pages. [corrected cite].
Direct 30/30® Blood Glucose Sensor, (Markwell Medical) Catalog, ©1990, ELCO Diagnostics Company. 1 page. [corrected cite].
DuPont[1] Dimension AR®. 1998. The chemistry analyzer that makes the most of your time, money and effort. Catalog. Dade International, Chemistry Systems. Newark, DE. 18 pages. [corrected cite].
Huang et al., Sep. 1997, A 0.5mW Passive Telemetry IC for Biomedical Applications, Proceedings of the 23rd European Solid-State Circuits Conference (ESSCIRC '97), pp. 172-175, Southampton, UK. [corrected cite].
Hunter et al. Mar. 31, 2000. Minimally Invasive Glucose Sensor and Insulin Delivery System. MIT Home Automation and Healthcare Consortium. Progress Report No. 2-5. 17 pages. [corrected cite].
Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310. [corrected cite].
Merriam-Webster Online Dictionary. Apr. 23, 2007. Definition of "nominal". http://www.merriam-webster.com/dictionary/nominal. [corrected cite].
Nafion® 117 Solution Product Description, Product No. 70160, Sigma-Aldrich Corp., St. Louis, MO. Downloaded from https://www.signaaldrich.com/cgi-bin/hsrun/Suite7/Suite/HAHTpage/Suite.HsExternal Prod . . . on Apr. 7, 2005. [corrected cite].

* cited by examiner

SENSOR HEAD FOR USE WITH IMPLANTABLE DEVICES

CROSS-REFERENCE TO RELATED APPLICATIONS

This application is a division of Ser. No. 11/021,162, filed Dec. 22, 2004, which is a continuation of Ser. No. 09/916,711, filed Jul. 27, 2001, now abandoned. Each of the aforementioned applications is incorporated by reference herein in its entirety, and each is hereby expressly made a part of this specification.

FIELD OF THE INVENTION

The present invention relates generally to novel sensor heads utilized with implantable devices, devices including these sensor heads and methods for determining analyte levels using these implantable devices. More particularly, the invention relates to sensor heads, implantable devices including these sensor heads and methods for monitoring glucose levels in a biological fluid using these devices.

BACKGROUND OF THE INVENTION

Amperometric electrochemical sensors require a counter electrode to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

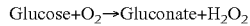

Because for each glucose molecule metabolized, there is a proportional change in the product $H_2O_2$, one can monitor the change in $H_2O_2$ to determine glucose concentration. Oxidation of $H_2O_2$ by the working electrode is balanced by reduction of ambient oxygen, enzyme generated $H_2O_2$, or other reducible species at the counter electrode. In vivo glucose concentration may vary from about one hundred times or more that of the oxygen concentration. Consequently, oxygen becomes a limiting reactant in the electrochemical reaction and when insufficient oxygen is provided to the sensor, the sensor will be unable to accurately measure glucose concentration. Those skilled in the art have come to interpret oxygen limitations resulting in depressed function as being a problem of availability of oxygen to the enzyme.

As shown in FIG. 1, the sensor head 10 includes a working electrode 21 (anode), counter electrode 22 (cathode), and reference electrode 20 which are affixed to the head by both brazing 26 the electrode metal to the ceramic and potting with epoxy 28. The working electrode 21 (anode) and counter-electrode 22 (cathode) of a glucose oxidase-based glucose sensor head 10 require oxygen in different capacities. Prior art teaches an enzyme-containing membrane that resides above an amperometric electrochemical sensor. In FIG. 1, region 32 includes an immobilized enzyme, i.e. glucose oxidase. Within the enzyme layer above the working electrode 21, oxygen is required for the production of $H_2O_2$ from glucose. The $H_2O_2$ produced from the glucose oxidase reaction further reacts at surface 21a of working electrode 21 and produces two electrons. The products of this reaction are two protons ($2H_+$), two electrons ($2e^-$), and one oxygen molecule ($O_2$) (Fraser, D. M. "An Introduction to In Vivo Biosensing: Progress and problems." In "Biosensors and the Body," D. M. Fraser, ed., 1997, pp. 1-56 John Wiley and Sons, New York).

In theory, the oxygen concentration near the working electrode 21, which is consumed during the glucose oxidase reaction, is replenished by the second reaction at the working electrode. Therefore, the net consumption of oxygen is zero. In practice, neither all of the $H_2O_2$ produced by the enzyme diffuses to the working electrode surface nor does all of the oxygen produced at the electrode diffuse to the enzyme domain.

With further reference to FIG. 1, the counter electrode 22 utilizes oxygen as an electron acceptor. The most likely reducible species for this system are oxygen or enzyme generated peroxide (Fraser, D. M. supra). There are two main pathways by which oxygen may be consumed at the counter electrode 22. These are a four-electron pathway to produce hydroxide and a two-electron pathway to produce hydrogen peroxide. The two-electron pathway is shown in FIG. 1. Oxygen is further consumed above the counter electrode by the glucose oxidase in region 32. Due to the oxygen consumption by both the enzyme and the counter electrode, there is a net consumption of oxygen at the surface 22a of the counter electrode. Theoretically, in the domain of the working electrode there is significantly less net loss of oxygen than in the region of the counter electrode. In addition, there is a close correlation between the ability of the counter electrode to maintain current balance and sensor function. Taken together, it appears that counter electrode function becomes limited before the enzyme reaction becomes limited when oxygen concentration is lowered.

Those practicing in the field of implantable glucose oxidase sensors have focused on improving sensor function by increasing the local concentration of oxygen in the region of the working electrode. (Fraser, D. M. supra).

We have observed that in some cases, loss of glucose oxidase sensor function may not be due to a limitation of oxygen in the enzyme layer near the working electrode, but may instead be due to a limitation of oxygen at the counter electrode. In the presence of increasing glucose concentrations, a higher peroxide concentration results, thereby increasing the current at the working electrode. When this occurs, the counter electrode limitation begins to manifest itself as this electrode moves to increasingly negative voltages in the search for reducible species. When a sufficient supply of reducible species, such as oxygen, are not available, the counter electrode voltage reaches a circuitry limit of −0.6V resulting in compromised sensor function (see FIG. 3).

FIG. 3 shows simultaneous measurement of counter-electrode voltage and sensor output to glucose levels from a glucose sensor implanted subcutaneously in a canine host. It can be observed that as glucose levels increase, the counter electrode voltage decreases. When the counter electrode voltage reaches −0.6V, the signal to noise ratio increases significantly. This reduces the accuracy of the device. FIG. 4 shows a further example of another glucose sensor in which the counter-electrode reaches the circuitry limit. Again, once the counter electrode reaches −0.6V, the sensitivity and/or signal to noise ratio of the device is compromised. In both of these examples, glucose levels reached nearly 300 mg/dl. However, in FIG. 3 the sensor showed a greater than three-fold higher current output than the sensor in FIG. 4. These data suggest that there may be a limitation of reducible species at the counter electrode, which may limit the sensitivity of the device as the glucose levels increase. In contrast, FIG. 5 shows a glucose sensor in which the counter electrode voltage did not reach −0.6V. In FIG. 5 it can be observed that the sensor was able to maintain a current balance between the working and counter electrodes, thereby enabling accurate measurements throughout the course of the experiment. The results shown in FIGS. 3, 4 and 5 led the present inventors to postulate that by keeping the counter electrode from reaching the circuitry limit, one could maintain sensitivity and accuracy of the device.

Two approaches have been utilized by others to relieve the counter electrode limitation described above. The first approach involves the widening of the potential range over which the counter electrode can move in the negative direction to avoid reaching circuitry limitations. Unfortunately, this approach increases undesirable products that are produced at lower potentials. One such product, hydrogen, may form at the counter electrode, which may then diffuse back to the working electrode. This may contribute to additional current resulting in erroneously high glucose concentration readings. Additionally, at these increasingly negative potentials, the probability of passivating or poisoning the counter electrode greatly increases. This effectively reduces the counter electrode surface area requiring a higher current density at the remaining area to maintain current balance. Furthermore, increased current load increases the negative potentials eventually resulting in electrode failure.

The second approach is utilizing the metal case of the device as a counter electrode (see U.S. Pat. No. 4,671,288, Gough or U.S. Pat. No. 5,914,026, Blubaugh). This provides an initial excess in surface area which is expected to serve the current balancing needs of the device over its lifetime. However, when the counter electrode reaction is a reduction reaction, as in Blubaugh, the normally present metal oxide layer will be reduced to bare metal over time leaving the surface subject to corrosion, poisoning, and eventual cascade failure. This problem is magnified when considering the various constituents of the body fluid that the metal casing is exposed to during in vivo use. To date, there has been no demonstration of long-term performance of such a device with this counter electrode geometry.

Consequently, there is a need for a sensor that will provide accurate analyte measurements, that reduces the potential for cascade failure due to increasing negative potentials, corrosion and poisoning, and that will function effectively and efficiently in low oxygen concentration environments.

SUMMARY OF THE INVENTION

In one aspect of the present invention, a sensor head for use in a device that measures the concentration of an analyte in a biological fluid is provided that includes a non-conductive body; a working electrode, a reference electrode and a counter electrode, wherein the electrodes pass through the non-conductive body forming an electrochemically reactive surface at one location on the body and forming an electronic connection at another location on the body, and further wherein the electrochemically reactive surface of the counter electrode is greater than the surface area of the working electrode; and a multi-region membrane affixed to the non-conductive body and covering the working electrode, reference electrode and counter electrode.

In another aspect of the present invention, a sensor head for use in an implantable analyte measuring device is provided which includes the same sensor head components as those described above.

The sensor heads of the present invention include a multi-region membrane that controls the number of species that are able to reach the surface of the electrodes. In particular, such a membrane allows the passage of desired substrate molecules (e.g. oxygen and glucose) and rejects other larger molecules that may interfere with accurate detection of an analyte. The sensor heads of the present invention also provide a larger counter electrode reactive surface that balances the current between the working and counter electrodes, thereby minimizing negative potential extremes that may interfere with accurate analyte detection.

In another aspect of the present invention, an implantable device for measuring an analyte in a biological fluid is provided including at least one of the sensor heads described above. In still another aspect of the present invention, a method of monitoring glucose levels is disclosed which includes the steps of providing a host, and an implantable device as provided above and implanting the device in the host.

Further encompassed by the invention is a method of measuring glucose in a biological fluid including the steps of providing a host and a implantable device described above, which includes a sensor head capable of accurate continuous glucose sensing; and implanting the device in the host.

The sensor head, membrane architectures, devices and methods of the present invention allow for the collection of continuous information regarding desired analyte levels (e.g. glucose). Such continuous information enables the determination of trends in glucose levels, which can be extremely important in the management of diabetic patients.

Definitions

In order to facilitate an understanding of the present invention, a number of terms are defined below.

The term "sensor head" refers to the region of a monitoring device responsible for the detection of a particular analyte. The sensor head generally comprises a non-conductive body, a working electrode (anode), a reference electrode and a counter electrode (cathode) passing through and secured within the body forming an electrochemically reactive surface at one location on the body and an electronic connective means at another location on the body, and a multi-region membrane affixed to the body and covering the electrochemically reactive surface. The counter electrode has a greater electrochemically reactive surface area than the working electrode. During general operation of the sensor a biological sample (e.g., blood or interstitial fluid) or a portion thereof contacts (directly or after passage through one or more membranes or domains) an enzyme (e.g., glucose oxidase); the reaction of the biological sample (or portion thereof) results in the formation of reaction products that allow a determination of the analyte (e.g. glucose) level in the biological sample. In preferred embodiments of the present invention, the multi-region membrane further comprises an enzyme domain, and an electrolyte phase (i.e., a free-flowing liquid phase comprising an electrolyte-containing fluid described further below).

The term "analyte" refers to a substance or chemical constituent in a biological fluid (e.g., blood, interstitial fluid, cerebral spinal fluid, lymph fluid or urine) that can be analyzed. A preferred analyte for measurement by the sensor heads, devices and methods of the present invention is glucose.

The term "electrochemically reactive surface" refers to the surface of an electrode where an electrochemical reaction takes place. In the case of the working electrode, the hydrogen peroxide produced by the enzyme catalyzed reaction of the analyte being detected reacts creating a measurable electronic current (e.g. detection of glucose analyte utilizing glucose oxidase produces $H_2O_2$ peroxide as a by product, $H_2O_2$ reacts with the surface of the working electrode producing two protons ($2H_+$), two electrons ($2e^-$) and one molecule of oxygen ($O_2$) which produces the electronic current being detected). In the case of the counter electrode, a reducible species, e.g. $O_2$ is reduced at the electrode surface in order to balance the current being generated by the working electrode.

The term "electronic connection" refers to any electronic connection known to those in the art that may be utilized to interface the sensor head electrodes with the electronic circuitry of a device such as mechanical (e.g., pin and socket) or soldered.

The term "domain" refers to regions of the membrane of the present invention that may be layers, uniform or non-uniform gradients (e.g. anisotropic) or provided as portions of the membrane.

The term "multi-region membrane" refers to a permeable membrane that may be comprised of two or more domains and constructed of biomaterials of a few microns thickness or more which are permeable to oxygen and may or may not be permeable to glucose. One of the membranes may be placed over the sensor body to keep host cells (e.g., macrophages) from gaining proximity to, and thereby damaging, the enzyme membrane or forming a barrier cell layer and interfering with the transport of analyte across the tissue-device interface.

The phrase "distant from" refers to the spatial relationship between various elements in comparison to a particular point of reference. For example, some embodiments of a biological fluid measuring device comprise a multi-region membrane that may be comprised of a number of domains. If the electrodes of the sensor head are deemed to be the point of reference, and one of the multi-region membrane domains is positioned farther from the electrodes, than that domain is distant from the electrodes.

The term "oxygen antenna domain" and the like refers to a domain composed of a material that has higher oxygen solubility than aqueous media so that it concentrates oxygen from the biological fluid surrounding the biointerface membrane. The domain can then act as an oxygen reservoir during times of minimal oxygen need and has the capacity to provide on demand a higher oxygen gradient to facilitate oxygen transport across the membrane. This enhances function in the enzyme reaction domain and at the counter electrode surface when glucose conversion to hydrogen peroxide in the enzyme domain consumes oxygen from the surrounding domains. Thus, this ability of the oxygen antenna domain to apply a higher flux of oxygen to critical domains when needed improves overall sensor function.

The term "solid portions" and the like refer to a material having a structure that may or may not have an open-cell configuration but in either case prohibits whole cells from traveling through or residing within the material.

The term "substantial number" refers to the number of cavities or solid portions having a particular size within a domain in which greater than 50 percent of all cavities or solid portions are of the specified size, preferably greater than 75 percent and most preferably greater than 90 percent of the cavities or solid portions have the specified size.

The term "co-continuous" and the like refers to a solid portion wherein an unbroken curved line in three dimensions exists between any two points of the solid portion.

The term "host" refers to both humans and animals.

The term "accurately" means, for example, 90% of measured glucose values are within the "A" and "B" region of a standard Clarke error grid when the sensor measurements are compared to a standard reference measurement. It is understood that like any analytical device, calibration, calibration validation and recalibration are required for the most accurate operation of the device.

The phrase "continuous glucose sensing" refers to the period in which monitoring of plasma glucose concentration is continuously performed, for example, about every 10 minutes.

DETAILED DESCRIPTION OF THE PREFERRED EMBODIMENT

Figure 1:
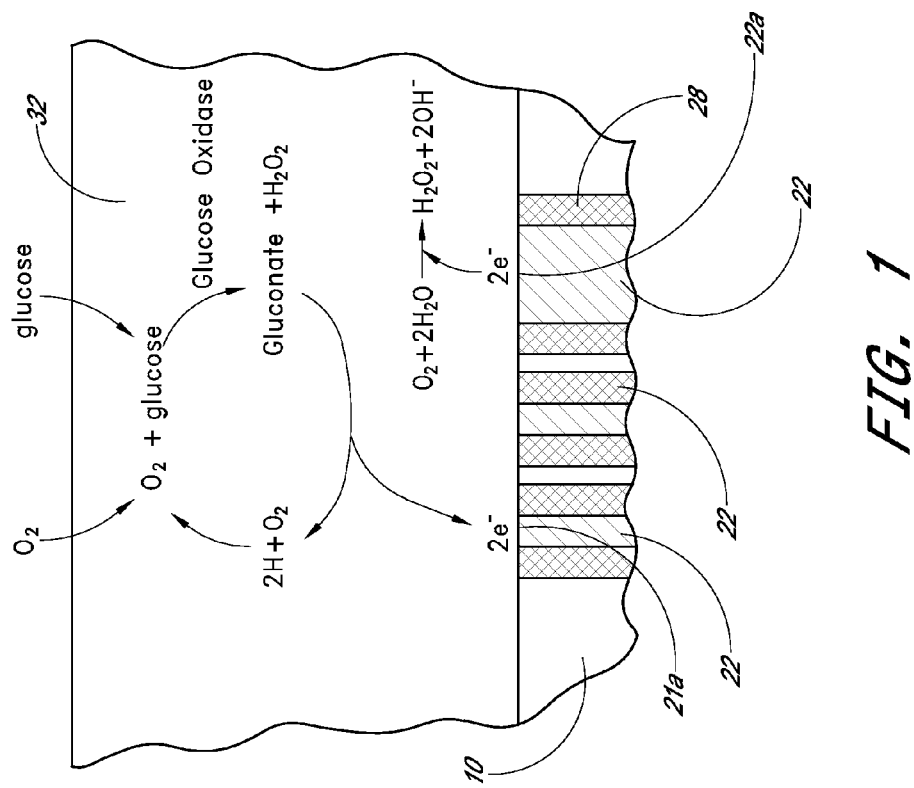
FIG. 1 Illustration of thermodynamically favored reactions at the working electrode and counter electrode at the desired voltage potentials.

In a preferred embodiment, the sensor heads, devices and methods of the present invention may be used to determine the level of glucose or other analytes in a host. The level of glucose is a particularly important measurement for individuals having diabetes in that effective treatment depends on the accuracy of this measurement.

The present invention increases the effectiveness of counter electrode function by a method that does not depend on increasing the local concentration of oxygen. In a preferred embodiment, the counter electrode has an electrochemical reactive surface area greater than twice the surface area of the working electrode thereby substantially increasing the electrodes ability to utilize oxygen as a substrate. Further enhancement of the counter electrode's activity may be achieved if the electrode were made of gold. In a second preferred embodiment, the counter electrode has a textured surface, with surface topography that increases the surface area of the electrode while the diameter of the electrode remains constant. In a third preferred embodiment, the proximity of the glucose oxidase enzyme to the counter electrode may be decreased. Since the enzyme depletes oxygen locally, the counter electrode would best be situated at a location distant from the enzyme. This could be achieved by depleting the enzyme from or inactivating the enzyme located in the region near and over the counter electrode by methods known to those skilled in the art such as laser ablation, or chemical ablation. Alternatively, the membrane could be covered with an additional domain where glucose is selectively blocked from the area over the counter electrode.

In particular, the present invention reduces the potential for electrode poisoning by positioning all electrodes underneath a multi-region membrane so that there is control of the species reaching the electrode surfaces. These membranes allow passage of dissolved oxygen to support the counter electrode reactions at reasonable negative potentials while rejecting larger molecules which when reduced would coat the surface of the counter electrode eventually leading to cascade failure. The positioning of the counter electrode underneath the membrane assures that all currents are passing through the same conductive media, thereby reducing voltage losses due to membrane or solution resistance. In addition, the counter electrode will be able to collect enough species for the balancing current while minimizing the need to move towards negative potential extremes.

Although the description that follows is primarily directed at glucose monitoring sensor heads, devices and methods for their use, the sensor heads, devices and methods of the present invention are not limited to glucose measurement. Rather, the devices and methods may be applied to detect and quantitate other analytes present in biological fluids (including, but not limited to, amino acids and lactate), especially those analytes that are substrates for oxidase enzymes [see, e.g., U.S. Pat. No. 4,703,756 to Gough et al., hereby incorporated by reference].

I. Nature of the Foreign Body Capsule

Devices and probes that are implanted into subcutaneous tissue will almost always elicit a foreign body capsule (FBC) as part of the body's response to the introduction of a foreign material. Therefore, implantation of a glucose sensor results in an acute inflammatory reaction followed by building of fibrotic tissue. Ultimately, a mature FBC comprising primarily a vascular fibrous tissue forms around the device (Shanker and Greisler, Inflammation and Biomaterials in Greco R S, ed. Implantation Biology: The Host Response and Biomedical Devices, pp 68-80, CRC Press (1994)).

In general, the formation of a FBC has precluded the collection of reliable, continuous information, reportedly because of poor vascularization (Updike, S. J. et al., "Principles of Long-term Fully Implanted Sensors with Emphasis on Radiotelemetric Monitoring of Blood Glucose from inside a Subcutaneous Foreign Body Capsule (FBC)" in "Biosensors and the Body," D. M. Fraser, ed., 1997, pp. 117-38, John Wiley and Sons, New York). Thus, those skilled in the art have previously attempted to minimize FBC formation by, for example, using a short-lived needle geometry or sensor coatings to minimize the foreign body.

In contrast to the prior art, the teachings of the present invention recognize that FBC formation is the dominant event surrounding long-term implantation of any sensor and must be managed to support, rather than hinder or block, sensor performance. It has been observed that during the early periods following implantation of an analyte sensing device, particularly a glucose sensing device, that glucose sensors function well. However, after a few days to two or more weeks of implantation, these devices lose their function.

We have observed that this lack of sensor function is most likely due to cells (barrier cells) that associate with the outer surface of the device and physically block the transport of glucose into the device (i.e. form a barrier cell layer). Increased vascularization would not be expected to overcome this blockage. The present invention contemplates the use of particular biointerface membrane architectures that interfere with barrier cell layer formation on the membrane's surface. The present invention also contemplates the use of these membranes with a variety of implantable devices (e.g. analyte measuring devices particularly glucose measuring devices).

II. The Sensor Head

In one embodiment of the sensor head of the invention, the body is made of a non-conductive material such as ceramic, glass, or polymer.

In a preferred embodiment, the sensor head interface region may include several different layers and/or membranes that cover and protect the electrodes of an implantable analyte-measuring device. The characteristics of these layers and/or membranes are now discussed in more detail. The layers and/or membranes prevent direct contact of the biological fluid sample with the electrodes, while permitting selected substances (e.g., analytes) of the fluid to pass therethrough for reaction in an enzyme rich domain with subsequent electrochemical reaction of formed products at the electrodes.

It is well known in the art that electrode surfaces exposed to a wide range of biological molecules may suffer poisoning of catalytic activity and possible corrosion that could result in failure. However, utilizing the unique multi-region membrane architectures of the present invention, the active electrochemical surfaces of the sensor electrodes are preserved, retaining activity for extended periods of time in vivo. By limiting access to the electrochemically reactive surface of the electrodes to a small number of molecular species such as, for example, molecules having a molecular weight of about 34 Daltons (the molecular weight of peroxide) or less, only a small subset of the many molecular species present in biological fluids are permitted to contact the sensor. Use of such membranes has enabled sustained function of devices for over one year in vivo.

A. Multi-Region Membrane

The multi-region membrane is constructed of two or more regions. The multi-region membrane may be provided in a number of different architectures. In one architecture, the multi-region membrane includes a first region distant from the electrochemically reactive surfaces, a second region less distant from the electrochemically reactive surfaces and a third region adjacent to the electrochemically reactive surfaces. The first region includes a cell disruptive domain distant from the electrochemically reactive surfaces and a cell impermeable domain less distant from the electrochemically reactive surfaces. The second region is a glucose exclusion domain and the third region includes a resistance domain distant from the electrochemically reactive surfaces, an immobilized enzyme domain less distant from the electrochemically reactive surfaces, an interference domain less distant from the electrochemically reactive surfaces than the immobilized enzyme domain and a hydrogel domain adjacent to the electrochemically reactive surfaces.

In another architecture, the multi-region membrane includes a first region distant from the electrochemically reactive surfaces and a further region less distant from the electrochemically reactive surfaces. The first region includes a cell disruptive domain and a cell impermeable domain as described above. The "further region" includes a resistance domain, immobilized enzyme domain, interference domain, and hydrogel domain and serves as the equivalent of the "third region" described above. In certain embodiments of the sensor head, the multi-region membrane further includes an oxygen antenna domain. Each of these domains will now be described in further detail.

i. Cell Disruptive Domain

The domain of the multi-region membrane positioned most distal to the electrochemically reactive surfaces corresponds to the cell disruptive domain. This domain includes a material that supports tissue in-growth and may be vascularized. The cell disruptive domain prevents formation of the barrier cell layer on the surface of the membrane, which as described above, blocks the transport of glucose into the sensor device. A useful cell disruptive domain is described in a U.S. application entitled "Membrane for use with Implantable Devices" which was filed on the same day as the present application. The cell disruptive domain may be composed of an open-cell configuration having cavities and solid portions. Cells may enter into the cavities, however, they can not travel through or wholly exist within the solid portions. The cavities allow most substances to pass through, including, e.g., macrophages.

The open-cell configuration yields a co-continuous solid domain that contains greater than one cavity in three dimensions substantially throughout the entirety of the membrane. In addition, the cavities and cavity interconnections may be formed in layers having different cavity dimensions.

A linear line can be used to define a dimension across a cavity or solid portion the length of which is the distance between two points lying at the interface of the cavity and solid portion. In this way, a substantial number of the cavities are not less than 20 microns in the shortest dimension and not more than 1000 microns in the longest dimension. Preferably, a substantial number of the cavities are not less than 25 microns in the shortest dimension and not more than 500 microns in the longest dimension.

Furthermore, the solid portion has not less than 5 microns in a substantial number of the shortest dimensions and not more than 2000 microns in a substantial number of the longest dimensions. Preferably, the solid portion is not less than 10 microns in a substantial number of the shortest dimensions and not more than 1000 microns in a substantial number of the longest dimensions and most preferably, not less than 10 microns in a substantial number of the shortest dimensions and not more than 400 microns in a substantial number of the longest dimensions.

The solid portion may be made of polytetrafluoroethylene or polyethylene-co-tetrafluoroethylene, for example. Preferably, the solid portion includes polyurethanes or block copolymers and, most preferably, includes silicone.

When non-woven fibers are utilized as the solid portion of the present invention, the non-woven fibers may be greater than 5 microns in the shortest dimension. Preferably, the non-woven fibers are about 10 microns in the shortest dimension and most preferably, the non-woven fibers are greater than or equal to 10 microns in the shortest dimension.

The non-woven fibers may be constructed of polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones, and block copolymers thereof including, for example, di-block, tri-block, alternating, random and graft copolymers (block copolymers are discussed in U.S. Pat. Nos. 4,803,243 and 4,686,044, hereby incorporated by reference). Preferably, the non-woven fibers are comprised of polyolefins or polyester or polycarbonates or polytetrafluoroethylene.

A subset of the cell disruptive domain is the oxygen antenna domain. This domain can act as an oxygen reservoir during times of minimal oxygen need and has the capacity to provide on demand a higher oxygen gradient to facilitate oxygen transport across the membrane. This domain may be composed of a material such as silicone, that has higher oxygen solubility than aqueous media so that it concentrates oxygen from the biological fluid surrounding the biointerface membrane. This enhances function in the enzyme reaction domain and at the counter electrode surface when glucose conversion to hydrogen peroxide in the enzyme domain consumes oxygen from the surrounding domains. Thus, this ability of the oxygen antenna domain to apply a higher flux of oxygen to critical domains when needed improves overall sensor function. Preferably, this domain is composed of silicone and has a thickness of about 100 microns.

The thickness of the cell disruptive domain is usually not less than about 20 microns and not more than about 2000 microns.

ii. Cell Impermeable Domain

The cell impermeable of the first region is positioned less distal to the electrochemically reactive surfaces than the cell disruptive domain of the same region. This domain is impermeable to host cells, such as macrophages. Cell impermeable domains are described in U.S. Pat. No. 6,001,067, herein incorporated by reference, and in copending, commonly owned U.S. application entitled "Membrane for use with Implantable Devices", Ser. No. 09/916,386, filed on even date herewith. The inflammatory response that initiates and sustains a FBC is associated with disadvantages in the practice of sensing analytes. Inflammation is associated with invasion of inflammatory response cells (e.g. macrophages) which have the ability to overgrow at the interface and form barrier cell layers, which may block transport of glucose across the biointerface membrane. These inflammatory cells may also biodegrade many artificial biomaterials (some of which were, until recently, considered nonbiodegradable). When activated by a foreign body, tissue macrophages degranulate, releasing from their cytoplasmic myeloperoxidase system hypochlorite (bleach) and other oxidative species. Hypochlorite and other oxidative species are known to break down a variety of polymers, including ether based polyurethanes, by a phenomenon referred to as environmental stress cracking. Alternatively, polycarbonate based polyurethanes are believed to be resistant to environmental stress cracking and have been termed biodurable. In addition, because hypochlorite and other oxidizing species are short-lived chemical species in vivo, biodegradation will not occur if macrophages are kept a sufficient distance from the enzyme active membrane.

The present invention contemplates the use of cell impermeable biomaterials of a few microns thickness or more (i.e., a cell impermeable domain) in most of its membrane architectures. This domain of the biointerface membrane is permeable to oxygen and may or may not be permeable to glucose and is constructed of biodurable materials (e.g. for period of several years in vivo) that are impermeable by host cells (e.g. macrophages) such as for example polymer blends of polycarbonate based polyurethane and PVP.

The thickness of the cell impermeable domain is not less than about 10 microns and not more than about 100 microns.

iii. Glucose Exclusion Domain

The glucose exclusion domain includes a thin, hydrophobic membrane that is non-swellable and blocks diffusion of glucose while being permeable to oxygen. The glucose exclusion domain serves to allow analytes and other substances that are to be measured or utilized by the sensor to pass through, while preventing passage of other substances. Preferably, the glucose exclusion domain is constructed of a material such as, for example, silicone.

The glucose exclusion domain has a preferred thickness not less than about 130 microns, more preferably not less than about 5 and not more than about 75 microns and most preferably not less than 15 microns and not more than about 50 microns.

iv. Resistance Domain

In one embodiment of the sensor head the "third region" or "further region" of the multi-region membrane includes a resistance domain. When present, the resistance domain is located more distal to the electrochemically reactive surfaces relative to other domains in this region. As described in further detail below, the resistance domain controls the flux of oxygen and glucose to the underlying enzyme domain. There is a molar excess of glucose relative to the amount of oxygen in samples of blood. Indeed, for every free oxygen molecule in extracellular fluid, there are typically more than 100 glucose molecules present [Updike et al., Diabetes Care 5:207-21 (1982)]. However, an immobilized enzyme-based sensor using oxygen ($O_2$) as cofactor must be supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane over the enzyme domain, linear response to glucose levels can be obtained only up to about 40 mg/dL; however, in a clinical setting, linear response to glucose levels are desirable up to at least about 500 mg/dL.

The resistance domain includes a semipermeable membrane that controls the flux of oxygen and glucose to the underlying enzyme domain (i.e., limits the flux of glucose), rendering the necessary supply of oxygen in non-rate-limiting excess. As a result, the upper limit of linearity of glucose measurement is extended to a much higher value than that which could be achieved without the resistance domain. The devices of the present invention contemplate resistance domains including polymer membranes with oxygen-to-glucose permeability ratios of approximately 200:1; as a result, one-dimensional reactant diffusion is adequate to provide excess oxygen at all reasonable glucose and oxygen concentrations found in the subcutaneous matrix [Rhodes et al., Anal. Chem., 66:1520-1529 (1994)].

In preferred embodiments, the resistance domain is constructed of a polyurethane urea/polyurethane-block-polyethylene glycol blend and has a thickness of not more than about 45 microns, more preferably not less than about 15 microns, and not more than about 40 microns and, most preferably, not less than about 20 microns, and not more than about 35 microns.

v. Immobilized Enzyme Domain

When the resistance domain is combined with the cell-impermeable domain, it is the immobilized enzyme domain which corresponds to the outermost domain of the "third region" or "further region", i.e. it is located more distal to the electrochemically reactive surfaces as compared to the other domains in this region. In one embodiment, the enzyme domain includes glucose oxidase. In addition to glucose oxidase, the present invention contemplates the use of a domain impregnated with other oxidases, e.g., galactose oxidase or uricase, for an enzyme-based electrochemical glucose sensor to perform well, the sensor's response must neither be limited by enzyme activity nor cofactor concentration. Because enzymes, including glucose oxidase, are subject to deactivation as a function of ambient conditions, this behavior needs to be accounted for in constructing sensors for long-term use.

Preferably, the domain is constructed of aqueous dispersions of colloidal polyurethane polymers including the enzyme. Preferably, the coating has a thickness of not less than about 2.5 microns and not more than about 12.5 microns, preferably about 6.0 microns.

vi. Interference Domain

The interference domain in the "third region" or "further region" is located less distant from the electrochemically reactive surfaces than the immobilized enzyme domain in this same region. It includes a thin membrane that can limit diffusion of molecular weight species greater than 34 kD. The interference domain serves to allow analytes and other substances that are to be measured by the electrodes to pass through, while preventing passage of other substances, including potentially interfering substances. The interference domain is preferably constructed of a polyurethane.

The interference domain has a preferred thickness of not more than about 5 microns, more preferably not less than about 0.1 microns, and not more than about 5 microns and, most preferably, not less than about 0.5 microns, and not more than about 3 microns.

vii. Hydrogel Domain

The hydrogel domain is located adjacent to the electrochemically reactive surfaces. To ensure electrochemical reaction, the hydrogel domain includes a semipermeable coating that maintains hydrophilicity at the electrode region of the sensor interface. The hydrogel domain enhances the stability of the interference domain of the present invention by protecting and supporting the membrane that makes up the interference domain. Furthermore, the hydrogel domain assists in stabilizing operation of the device by overcoming electrode start-up problems and drifting problems caused by inadequate electrolyte. The buffered electrolyte solution contained in the hydrogel domain also protects against pH-mediated damage that may result from the formation of a large pH gradient between the hydrophobic interference domain and the electrode (or electrodes) due to the electrochemical activity of the electrode(s).

Preferably, the hydrogel domain includes a flexible, water-swellable, substantially solid gel-like film having a "dry film" thickness of not less than about 2.5 microns and not more than about 12.5 microns; preferably, the thickness is about 6.0 microns. "Dry film" thickness refers to the thickness of a cured film cast from a coating formulation onto the surface of the membrane by standard coating techniques Suitable hydrogel domains are formed of a curable copolymer of a urethane polymer and a hydrophilic film-forming polymer. Particularly preferred coatings are formed of a polyurethane polymer having anionic carboxylate functional groups and non-ionic hydrophilic polyether segments, which is crosslinked in the present of polyvinylpyrrolidone and cured at a moderate temperature of about 50° C.

B. Electrolyte Phase

The electrolyte phase is a free-fluid phase including a solution containing at least one compound, usually a soluble chloride salt, that conducts electric current. The electrolyte phase flows over the electrodes and is in contact with the hydrogel domain. The devices of the present invention contemplate the use of any suitable electrolyte solution, including standard, commercially available solutions.

Generally speaking, the electrolyte phase should have the same or less osmotic pressure than the sample being analyzed. In preferred embodiments of the present invention, the electrolyte phase includes normal saline.

C. Membrane Architectures

Prior art teaches that an enzyme containing membrane that resides above an amperometric electrochemical sensor can possess the same architecture throughout the electrode surfaces. However, the function of converting glucose into hydrogen peroxide by glucose oxidase may only by necessary above the working electrode. In fact, it may be beneficial to limit the conversion of glucose into hydrogen peroxide above the counter electrode. Therefore, the present invention contemplates a number of membrane architectures that include a multi-region membrane wherein the regions include at least one domain.

Figure 2A:
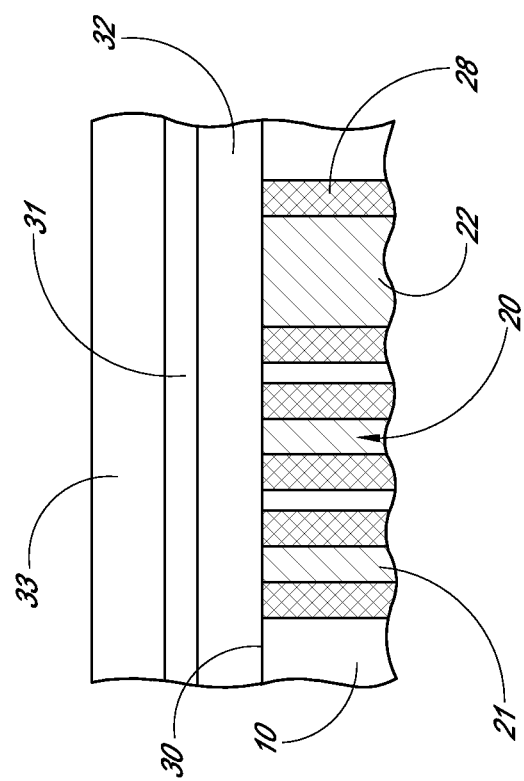
FIG. 2A depicts a cross-sectional exploded view of a sensor head of the present invention wherein the multi-region membrane comprises three regions.

Referring now to FIG. 2A, which shows one desired embodiment of the general architecture of a three region membrane, first region 33 is permeable to oxygen and glucose and includes a cell disruptive domain distant from the electrodes and a cell impermeable domain less distant from the electrodes. The second region 31 is permeable to oxygen and includes a glucose exclusion domain and region three 32 includes a resistance domain, distant from the electrochemically reactive surfaces, an immobilized enzyme domain less distant from the electrochemically reactive surfaces, an interference domain less distant from the electrochemically reactive surfaces than the immobilized enzyme and a hydrogel domain adjacent to the electrochemically reactive surfaces. The multi-region membrane is positioned over the sensor interface 30 of the non-conductive body 10, covering the working electrode 21, the reference electrode 20 and the counter electrode 22. The electrodes are brazed to the sensor head and back filled with epoxy 28.

Figure 2B:
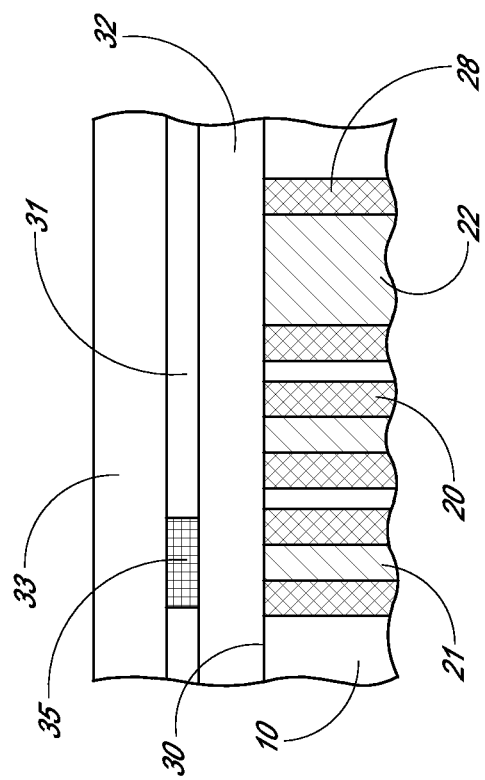
FIG. 2B depicts a cross-sectional exploded view of a sensor head of the present invention wherein a portion of the second membrane region does not cover the working electrode.

In FIG. 2B, the glucose exclusion domain has been positioned over the electrochemically reactive surfaces such that it does not cover the working electrode 21. To illustrate this, a hole 35 has been created in the second region 31 and positioned directly above the working electrode 21. In this way, glucose is blocked from entering the underlying enzyme membrane above the counter electrode 22 and $O_2$ is conserved above the counter electrode because it is not being consumed by the glucose oxidation reaction. The glucose-blocking domain is made of a material that allows sufficient $O_2$ to pass to the counter electrode. The glucose-blocking domain may be made of a variety of materials such as silicone or silicone containing copolymers. Preferably, the glucose-blocking domain is made of silicone.

Figure 2C:
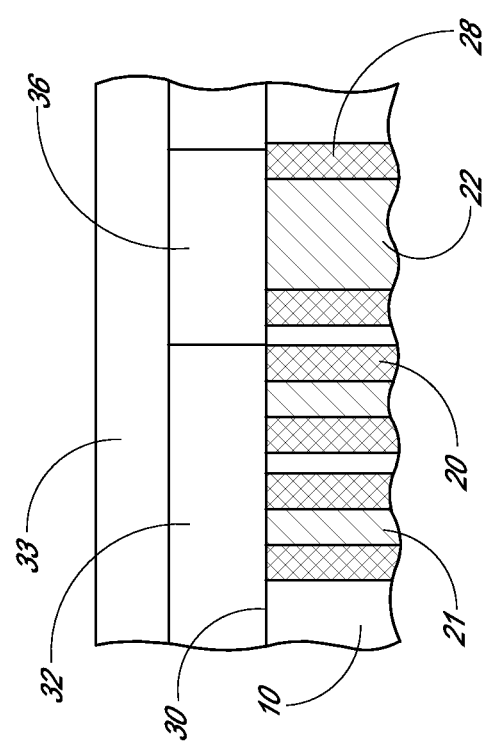
FIG. 2C depicts a cross-sectional exploded view of a sensor head of the present invention which includes two distinct regions, wherein the region adjacent the electrochemically reactive surfaces includes a portion positioned over the counter electrode which corresponds to a silicone domain.

In FIG. 2C, the multi-region membrane is shown as being constructed of two regions: a first region 33 which includes a cell disruptive domain and a cell impermeable domain; and a further region 32. Region 32 is defined herein as including an enzyme immobilized domain, interference domain, and hydrogel domain and may also include a resistance domain. Region 32 is referred to as the "third region" in embodiments where the multi-region membrane includes three regions. In the embodiment shown, a silicone domain plug 36 positioned over the counter electrode 22 in order to eliminate the consumption of $O_2$ above the counter electrode by the oxidation of glucose with glucose oxidase. The enzyme immobilized domain can be fabricated as previously described, then a hole punched into the domain. The silicone domain plug 36 may be cut to fit the hole, and then adhered into place, for example, with silicone adhesive (e.g., MED-1511, NuSil, Carpinteria, Calif.).

Figure 2D:
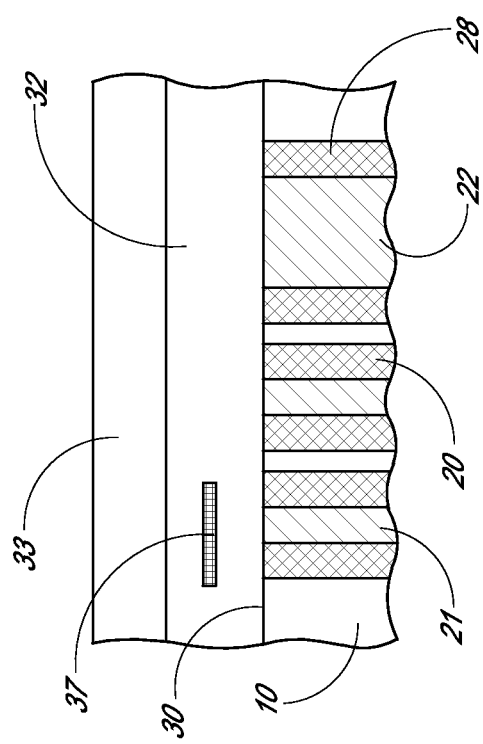
FIG. 2D depicts a cross-sectional exploded view of a sensor head of the present invention wherein an active enzyme of the immobilized enzyme domain is positioned only over the working electrode.

In FIG. 2D, the immobilized enzyme domain of the multi-region membrane can be fabricated such that active enzyme 37 is positioned only above the working electrode 21. In this architecture, the immobilized enzyme domain may be prepared so that the glucose oxidase only exists above the working electrode 21. During the preparation of the multi-region membrane, the immobilized enzyme domain coating solution can be applied as a circular region similar to the diameter of the working electrode. This fabrication can be accomplished in a variety of ways such as screen printing or pad printing. Preferably, the enzyme domain is pad printed during the enzyme membrane fabrication with equipment as available from Pad Print Machinery of Vermont (Manchester, Vt.). These architectures eliminate the consumption of $O_2$ above the counter electrode 22 by the oxidation of glucose with glucose oxidase.

Figure 2E:
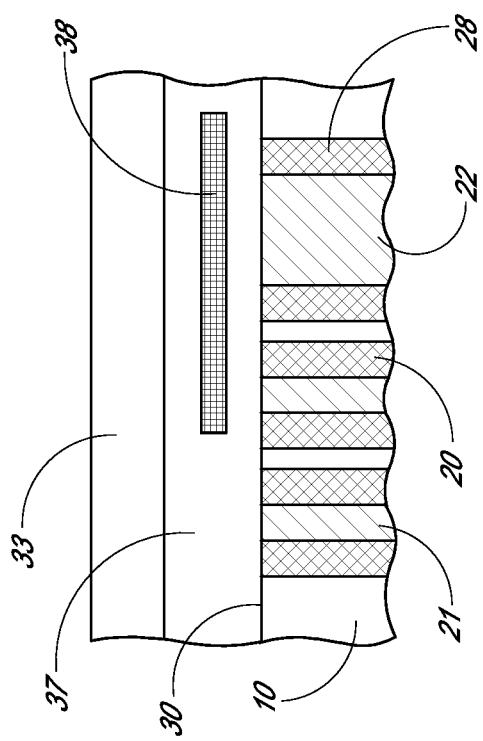
FIG. 2E depicts a cross-sectional exploded view of a sensor head of the present invention wherein the enzyme positioned over the counter electrode has been inactivated.

In FIG. 2E, the immobilized enzyme of the multi-region membrane in region 32 may be deactivated 38 except for the area covering the working electrode 21. In some of the previous membrane architectures, the glucose oxidase is distributed homogeneously throughout the immobilized enzyme domain. However, the active enzyme need only reside above the working electrode. Therefore, the enzyme may be deactivated 38 above the counter 22 and reference 20 electrodes by irradiation. A mask that covers the working electrode 21, such as those used for photolithography can be placed above the membrane. In this way, exposure of the masked membrane to ultraviolet light deactivates the glucose oxidase in all regions except that covered by the mask.

Figure 2F:
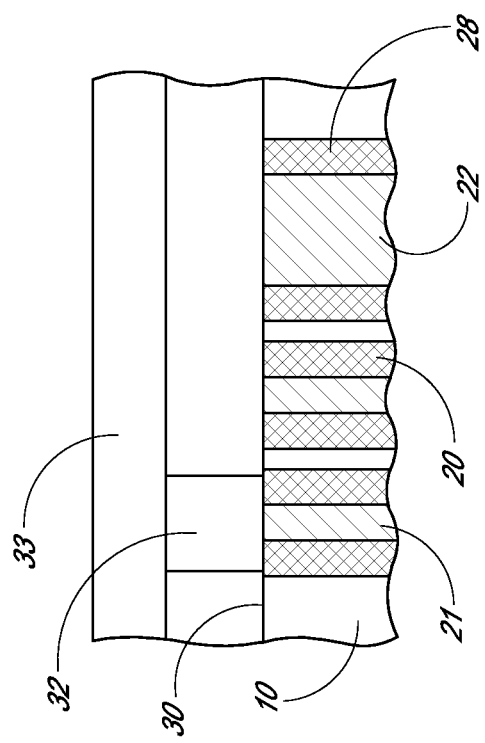
FIG. 2F depicts a cross-sectional exploded view of a sensor head of the present invention wherein the membrane region containing immobilized enzyme is positioned only over the working electrode.
Figure 3:
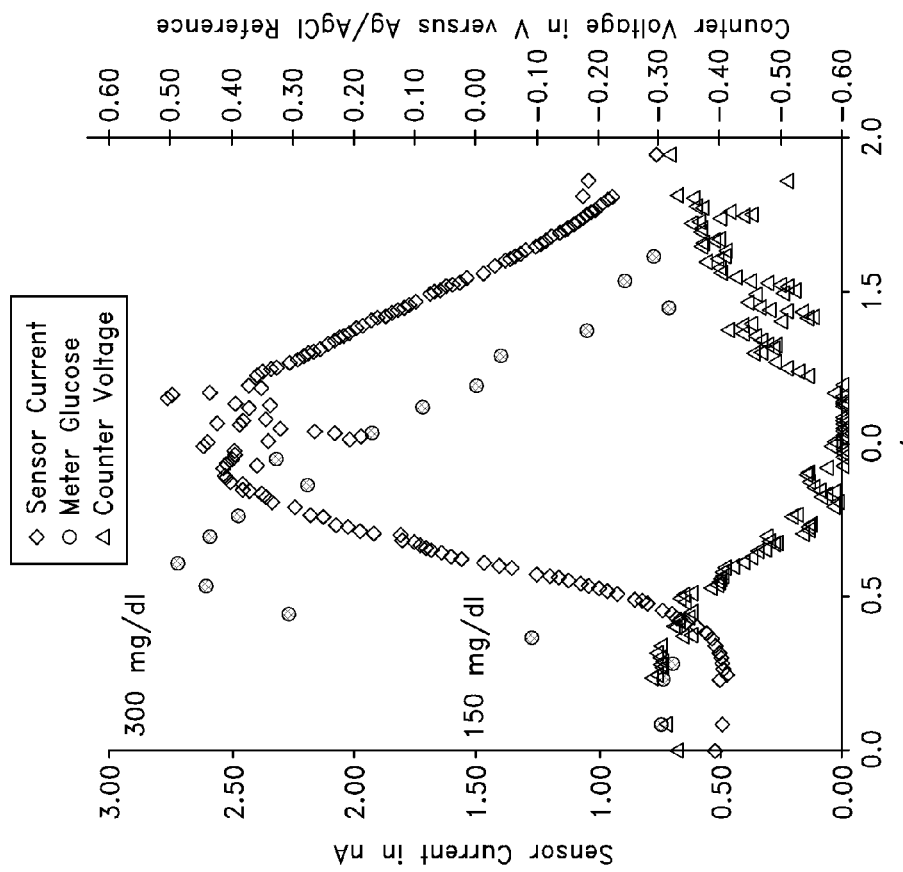
FIG. 3 Illustration of an implantable glucose sensor's ability to measure glucose concentration during an infusion study in a canine when the counter electrode voltage drops to the electronic circuitry limit at approximately 0.75 hours wherein the sensor current output reaches 2.50 nA.
Figure 4:
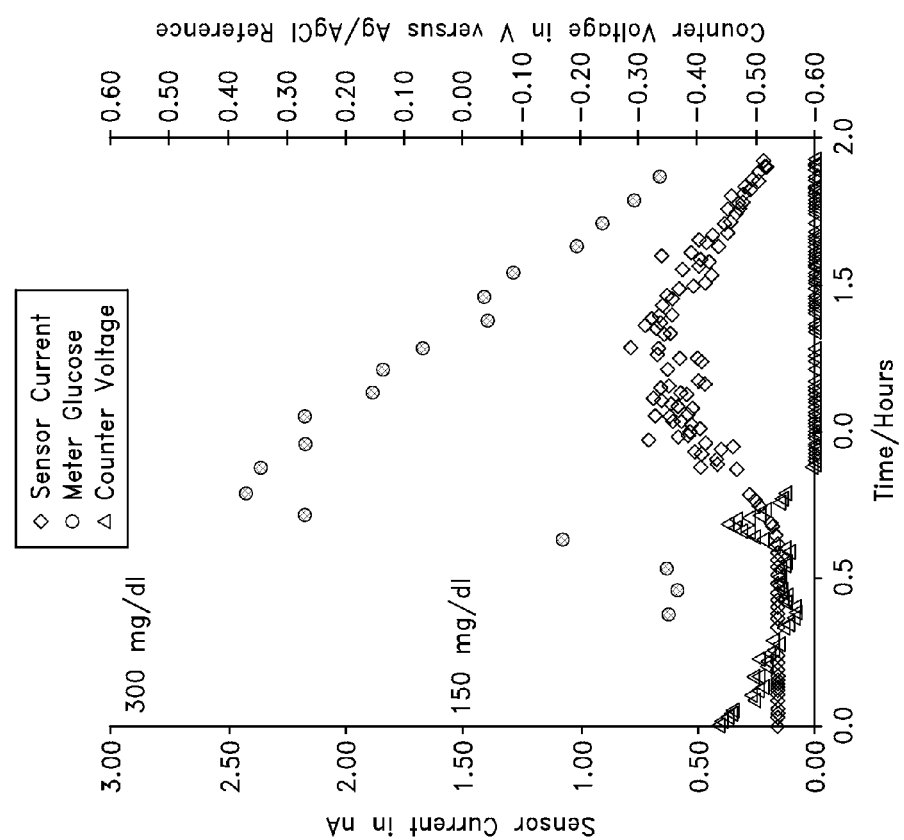
FIG. 4 Illustration of an implantable glucose sensor's ability to measure glucose concentration during an infusion study in a canine when the counter electrode voltage drops to the electronic circuitry limit after 0.5 hours wherein the sensor current output reaches 0.50 nA.
Figure 5:
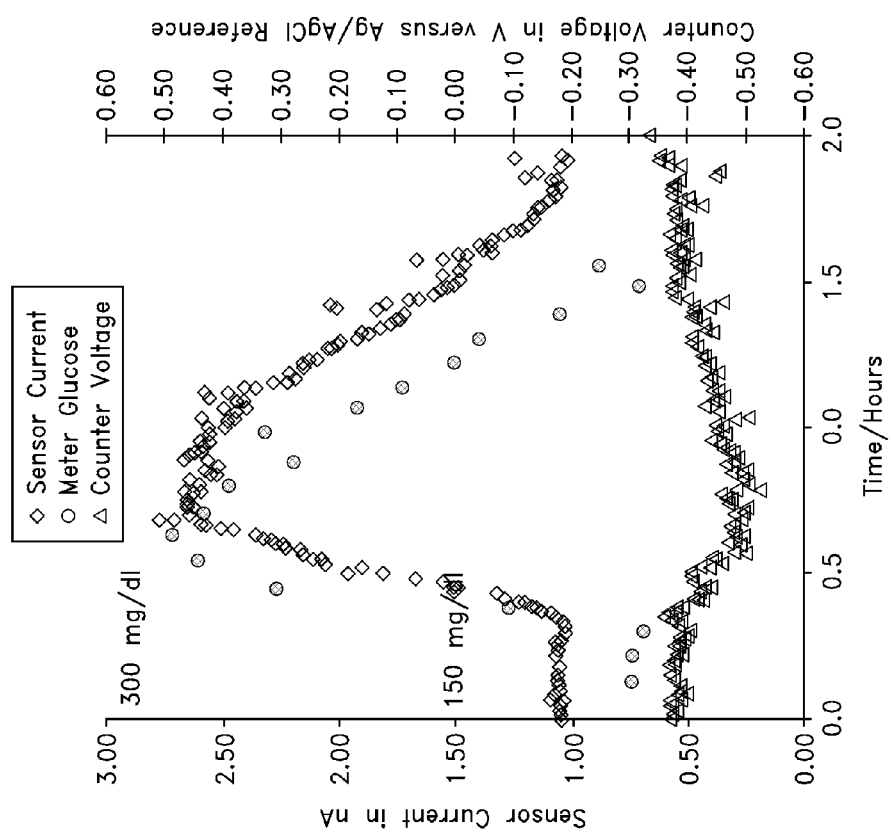
FIG. 5 Illustration of an implantable glucose sensor's ability to measure glucose concentration during an infusion study in a canine when the counter electrode voltage is maintained above the electronic circuitry limit.

FIG. 2F shows an architecture in which the third region 32 which includes immobilized enzyme only resides over the working electrode 21. In this architecture, consumption of $O_2$ above the counter electrode 22 by the oxidation of glucose with glucose oxidase is eliminated.

D. The Electrode Assembly

The electrode assembly of this invention comprises a non-conductive body and three electrodes affixed within the body having electrochemically reactive surfaces at one location on the body and an electronic connection means at another location on the body and may be used in the manner commonly employed in the making of amperometric measurements. A sample of the fluid being analyzed is placed in contact with a reference electrode, e.g., silver/silver-chloride, a working electrode which is preferably formed of platinum, and a counter electrode which is preferably formed of gold or platinum. The electrodes are connected to a galvanometer or polarographic instrument and the current is read or recorded upon application of the desired D.C. bias voltage between the electrodes.

The ability of the present device electrode assembly to accurately measure the concentration of substances such as glucose over a broad range of concentrations in fluids including undiluted whole blood samples enables the rapid and accurate determination of the concentration of those substances. That information can be employed in the study and control of metabolic disorders including diabetes.

The present invention contemplates several structural architectures that effectively increase the electrochemically reactive surface of the counter electrode. In one embodiment, the diameter of wire used to create the counter electrode is at least twice the diameter of the working electrode. In this architecture, it is preferable that the electrochemically reactive surface of the counter electrode be not less than about 2 and not more than about 100 times the surface area of the working electrode. More preferably, the electrochemically reactive surface of the counter electrode is not less than about 2 and not more than about 50, not less than about 2 and not more than about 25 or not less than about 2 and not more than about 10 times the surface area of the working electrode. In another embodiment, the electrochemically reactive surface is larger that the wire connecting this surface to the sensor head. In this architecture, the electrode could have a cross-sectional view that resembles a "T". The present invention contemplates a variety of configurations of the electrode head that would provide a large reactive surface, while maintaining a relatively narrow connecting wire. Such configurations could be prepared by micromachining with techniques such as reactive ion etching, wet chemical etching and focused ion beam machining as available from Norsam Technologies (Santa Fe, N.Mex.).

In another embodiment, the diameter of the counter electrode is substantially similar to the working electrode; however, the surface of the counter electrode has been modified to increase the surface area such that it has at least twice the surface area of the working electrode. More specifically the counter electrodes surface may be textured, effectively increasing its surface area without significantly increasing its diameter. This may be accomplished by a variety of methods known to those skilled in the art including, such as acid etching. The electrochemically reactive surface may be provided in a variety of shapes and sizes (e.g. round, triangular, square or free form) provided that it is at least twice the surface area of the working electrode.

In all of the architectures described, the electrodes are prepared from a 0.020" diameter wire having the desired modified reactive surface. The electrodes are secured inside the non-conductive body by brazing. The counter electrode is preferably made of gold or platinum.

III. Analyte Measuring Device

Figure 6A:
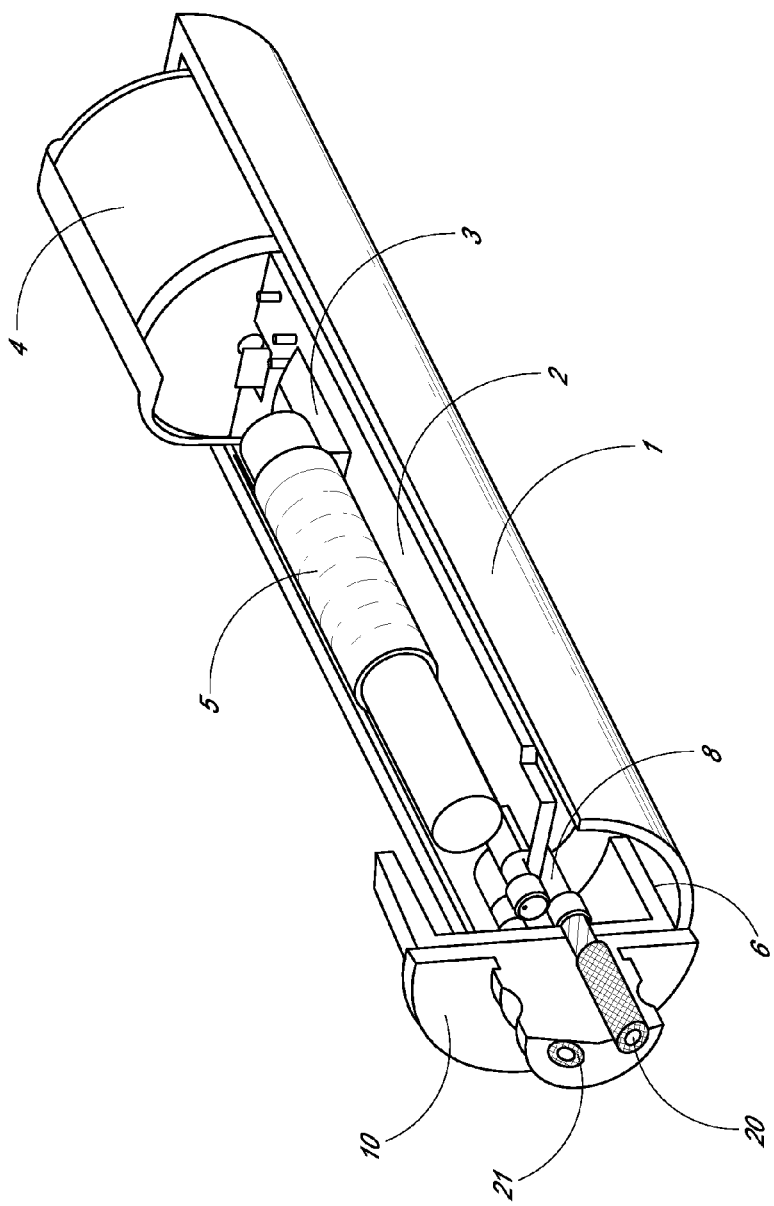
FIG. 6A shows a schematic representation of a cylindrical analyte measuring device including a sensor head according to the present invention.

A preferred embodiment of an analyte measuring device including a sensor head according to the present invention is shown in FIG. 6A. In this embodiment, a ceramic body 1 and ceramic head 10 houses the sensor electronics that include a circuit board 2, a microprocessor 3, a battery 4, and an antenna 5. Furthermore, the ceramic body 1 and head 10 possess a matching taper joint 6 that is sealed with epoxy. The electrodes are subsequently connected to the circuit board via a socket 8.

Figure 6B:
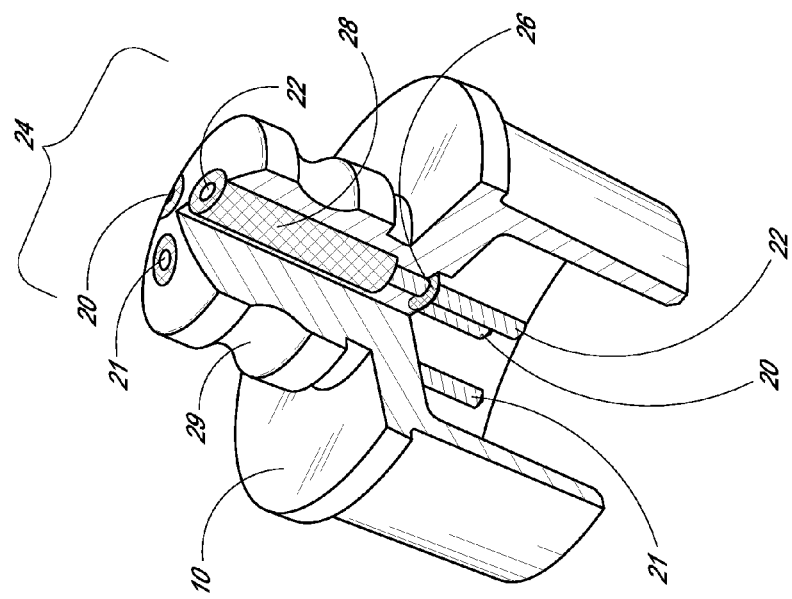
FIG. 6B is an exploded view of the sensor head of the device shown in FIG. 6A.

As indicated in detail in FIG. 6B, three electrodes protrude through the ceramic head 10, a platinum working electrode 21, a platinum counter electrode 22 and a silver/silver chloride reference electrode 20. Each of these is hermetically brazed 26 to the ceramic head 10 and further secured with epoxy 28. The sensing region 24 is covered with a multi-region membrane described above and the ceramic head 10 contains a groove 29 so that the membrane may be affixed into place with an o-ring.

IV. Experimental

The following examples serve to illustrate certain preferred embodiments and aspects of the present invention and are not to be construed as limiting the scope thereof.

In the preceding description and the experimental disclosure which follows, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade); Astor Wax (Titusville, Pa.); BASF Wyandotte Corporation (Parsippany, N.J.); Data Sciences, Inc. (St. Paul, Minn.); DuPont (DuPont Co., Wilmington, Del.); Exxon Chemical (Houston, Tex.); GAF Corporation (New York, N.Y.); Markwell Medical (Racine, Wis.); Meadox Medical, Inc. (Oakland, N.J.); Mobay (Mobay Corporation, Pittsburgh, Pa.); NuSil Technologies (Carpenteria, Calif.) Sandoz (East Hanover, N.J.); and Union Carbide (Union Carbide Corporation; Chicago, Ill.).

EXAMPLE 1

Preparation of the Multi-Region Membrane

A. Preparation of the First Region

The cell disruptive domain may be an ePTFE filtration membrane and the cell impermeable domain may then be coated on this domain layer. The cell impermeable domain was prepared by placing approximately 706 gm of dimethylacetamide (DMAC) into a 3 L stainless steel bowl to which a polycarbonateurethane solution (1325 g, Chronoflex AR 25% solids in DMAC and 5100 cp) and polyvinylpyrrolidone (125 g, Plasdone K-90 D) are added. The bowl was then fitted to a planetary mixer with a paddle type blade and the contents were stirred for 1 hour at room temperature. This solution was then coated on the cell disruptive domain by knife edge drawn at a gap of 0.006" and dried at 60° C. for 24 hours.

Alternatively, the polyurethane polyvinylpyrrolidone solution prepared above can be coated onto a PET release liner using a knife over roll coating machine. This material is then dried at 305° F. for approximately 2 minutes. Next the ePTFE membrane is immersed in 50:50 (w/v) mixture of THF/DMAC and then placed atop the coated polyurethane polyvinylpyrrolidone material. Light pressure atop the assembly intimately embeds the ePTFE into the polyurethane polyvinylpyrrolidone. The membrane is then dried at 60° C. for 24 hours.

B. Preparation of the Glucose Exclusion Domain

An oxime cured silicone dispersion (NuSil Technologies, MED-6607) was cast onto a polypropylene sheet and cured at 40° C. for three days.

C. Preparation of the Third Region

The "third region" or "further region" includes a resistance domain, an immobilized enzyme domain, an interference domain and a hydrogel domain. The resistance domain was prepared by placing approximately 281 gm of dimethylacetamide into a 3 L stainless steel bowl to which a solution of polyetherurethaneurea (344 gm of Chronothane H, 29,750 cp at 25% solids in DMAC). To this mixture was added another polyetherurethaneurea (312 gm, Chronothane 1020, 6275 cp at 25% solids in DMAC.) The bowl was fitted to a planetary mixer with a paddle type blade and the contents were stirred for 30 minutes at room temperature. The resistance domain coating solutions produced is coated onto a PET release liner (Douglas Hansen Co., Inc. Minneapolis, Minn.) using a knife over roll set at a 0.012" gap. This film is then dried at 305° F. The final film is approximately 0.0015" thick.

The immobilized enzyme domain was prepared by placing 304 gm polyurethane latex (Bayhydrol 140 AQ, Bayer, Pittsburgh, Pa.) into a 3 L stainless steel bowl to which 51 gm of pyrogen free water and 5.85 gm of glucose oxidase (Sigma type VII from *Aspergillus niger*) is added. The bowl was then fitted to a planetary mixer with a whisk type blade and the mixture was stirred for 15 minutes. Approximately 24 hr prior to coating a solution of glutaraldehyde (15.4 mL of a 2.5% solution in pyrogen free water) and 14 mL of pyrogen free water was added to the mixture. The solution was mixed by inverting a capped glass bottle by hand for about 3 minutes at room temperature. This mixture was then coated over the resistance domain with a #10 Mayer rod and dried above room temperature preferably at about 50° C.

The interference domain was prepared by placing 187 gm of tetrahydrofuran into a 500 mL glass bottle to which an 18.7 gm aliphatic polyetherurethane (Tecoflex SG-85A, Thermedics Inc., Woburn, Mass.) was added. The bottle was placed onto a roller at approximately 3 rpm within an oven set at 37° C. The mixture was allowed to roll for 24 hr. This mixture was coated over the dried enzyme domain using a flexible knife and dried above room temperature preferably at about 50° C.

The hydrogel domain was prepared by placing 388 gm of polyurethane latex (Bayhydrol 123, Bayer, Pittsburgh, Pa. in a 3 L stainless steel bowl to which 125 gm of pyrogen free water and 12.5 gm polyvinylpyrrolidone (Plasdone K-90D) was added. The bowl was then fitted to a planetary mixer with a paddle type blade and stirred for 1 hr at room temperature. Within 30 minutes of coating approximately 13.1 mL of carbodiimide (UCARLNK) was added and the solution was mixed by inverting a capped polyethylene jar by hand for about 3 min at room temperature. This mixture was coated over the dried interference domain with a #10 Mayer rod and dried above room temperature preferably at about 50° C.

In order to affix this multi-region membrane to a sensor head, it is first placed into buffer for about 2 minutes. It is then stretched over the nonconductive body of sensor head and affixed into place with an o-ring.

EXAMPLE 2

In Vitro Evaluation of Sensor Devices

This example describes experiments directed at sensor function of several sensor devices contemplated by the present invention.

In vitro testing of the sensor devices was accomplished in a manner similar to that previously described. [Gilligan et al., Diabetes Care 17:882-887 (1994)]. Briefly, devices were powered on and placed into a polyethylene container containing phosphate buffer (450 ml, pH 7.30) at 37° C. The container was placed onto a shaker (Lab Line Rotator, model 1314) set to speed 2. The sensors were allowed to equilibrate for at least 30 minutes and their output value recorded. After this time, a glucose solution (9.2 ml of 100 mg/ml glucose in buffer) was added in order to raise the glucose concentration to 200 mg/dl within the container. The sensors were allowed to equilibrate for at least 30 minutes and their output value recorded. Again, a glucose solution (9.4 ml of 100 mg/ml glucose in buffer) was added in order to raise the glucose concentration to 400 mg/dl within the container. The sensors were allowed to equilibrate for at least 30 minutes and their output value recorded. In this way, the sensitivity of the sensor to glucose is given as the slope of sensor output versus glucose concentration. The container was then fitted with an $O_2$ meter (WTW, model Oxi-340) and a gas purge. A mixture of compressed air and nitrogen was used to decrease the $O_2$ concentration. Sensor output was recorded at an ambient $O_2$ level, then sensor output was recorded for the following $O_2$ concentrations; 1 mg/L, 0.85 to 0.75 mg/L, 0.65 to 0.55 mg/L and 0.40 to 0.30 mg/L. In this way, the function of the sensor could be compared to its function at ambient $O_2$.

Sensor devices like the one shown in FIGS. 6A and 6B, which included inventive sensor heads having a multi-region membrane with the architecture shown in FIG. 2B, were tested in vitro. Eight of these devices were fitted with membranes that possessed a 0.020" diameter hole, four with a 0.0015" thick polyurethane (Chronoflex AR, CardioTech International Inc.) and four with a 0.032" thick silicone (MED-1511, NuSil Technologies Inc.). The hole was positioned above the working electrode and both membranes were secured to the device with an o-ring. Four control devices were also tested which were fitted with a multi-region membrane which lacked region 31 shown in FIG. 2B.

As discussed above, for oxygen to be consumed in the sensing region 32 above the electrodes, glucose is required. By placing region 31 shown in FIG. 2B, which includes a glucose blocking domain, above all areas other than above the working electrode 21, oxygen consumption in areas other than working electrode areas is limited. In contrast, by eliminating region 31 in the control devices, less overall oxygen becomes available to electrode surfaces due to the increased availability of glucose.

The devices were activated, placed into a 500 ml-polyethylene container with sodium phosphate buffered solution (300 ml, pH 7.3) and allowed to equilibrate. Each device's baseline value was recorded. Then 12 ml of glucose solution (100 mg/ml in sodium phosphate buffer) was added to the container so that the total glucose concentration became 400 mg/dL. After this, the container was covered and fitted with an oxygen sensor and a source of nitrogen and compressed air. In this way, the oxygen concentration was controlled with a gas sparge. A glucose value was recorded for each device at decreasing oxygen concentrations from ambient to approximately 0.1 mg/L.

Figure 7:
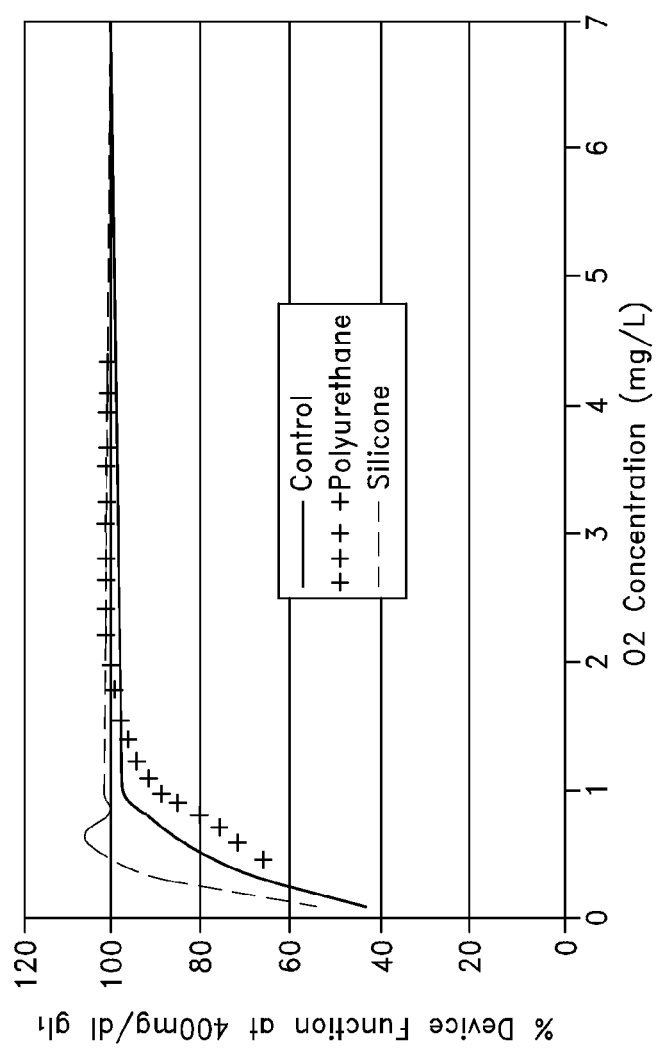
FIG. 7 Graphical representation of the function of a device of the present invention utilizing the multi-region membrane architecture of FIG. 2B in vitro at 400 mg/dL glucose.

FIG. 7 graphically represents the formation of a device of the present invention utilizing the multi-region membrane architecture in FIG. 2B in vitro. The data is expressed in percent Device Function at 400 mg/dL glucose vs. oxygen concentration. The percent function of the device is simply the device output at any given oxygen concentration divided by that device's output at ambient oxygen. The results from FIG. 7 indicate that inventive sensor devices containing the silicone membrane have better function at lower oxygen concentrations relative to both the control devices and the devices containing the polyurethane membrane. For example, at an oxygen concentration of about 0.5 mg/L, devices containing the silicone membrane are providing 100% output as compared to 80% output for the control devices.

EXAMPLE 3

Figure 8:
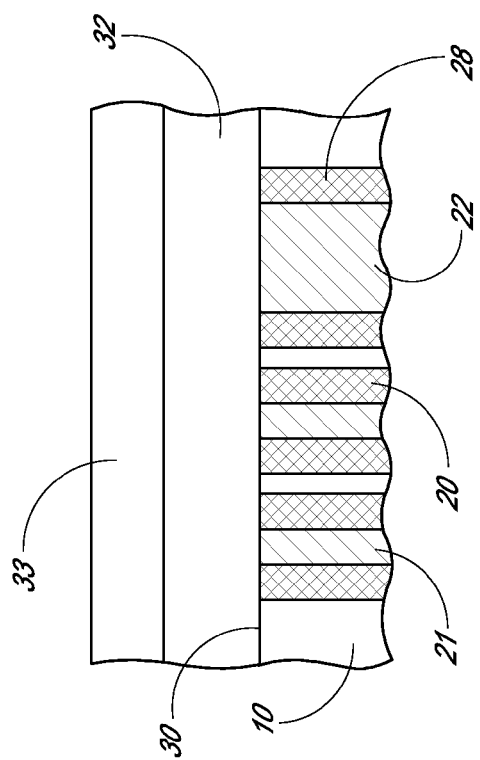
FIG. 8 depicts a cross-sectional exploded view of the electrode and membrane regions of a prior sensor device where the electrochemical reactive surface of the counter electrode is substantially equal to the surface area of the working electrode.

The Effect of Varying the Size and Material of the Counter Electrode on Sensor Response and Accuracy An in vitro testing procedure used in this example was similar to that described in Example 2. Six devices similar to the one shown in FIGS. 6A and 6B were fitted with the multi-region membrane described herein. Two of these tested devices were comparative devices that possessed Pt counter electrodes having a 0.020" diameter; this diameter provided for an electrochemically reactive surface of the counter electrode which was substantially equal to the surface area of the working electrode, as schematically shown in FIG. 8. In FIG.

8, the electrode-membrane region includes two distinct regions, the compositions and functions of which have already been described. Region 32 includes an immobilized enzyme. Region 33 includes a cell disruptive domain and a cell impermeable domain. The top ends of electrodes 21 (working), 20 (reference) and 22 (counter) are in contact with an electrolyte phase 30, a free-flowing phase. Two other tested devices possessed Pt counter electrodes having a 0.060" diameter. Finally, two additional devices possessed Au counter electrodes having a 0.060" diameter. The 0.006" diameter devices provided for an electrochemically reactive surface of the counter electrode which was approximately six times the surface area of the working electrode. Each of the devices including counter electrodes of 0.060" diameter include a multi-region membrane above the electrode region which is similar to that shown in FIG. 8.

The devices were activated, placed into a 500 ml-polyethylene container with sodium phosphate buffered solution (300 ml, pH 7.3) and allowed to equilibrate. Each device's baseline value was recorded. Then 12 ml of glucose solution (100 mg/ml in sodium phosphate buffer) was added to the container so that the total glucose concentration became 400 mg/dL. After this, the container was covered and fitted with an oxygen sensor and a source of nitrogen and compressed air. In this way, the oxygen concentration was controlled with a gas sparge. A counter electrode voltage was recorded for each device at decreasing oxygen concentrations from ambient to approximately 0.1 mg/L.

Figure 9:
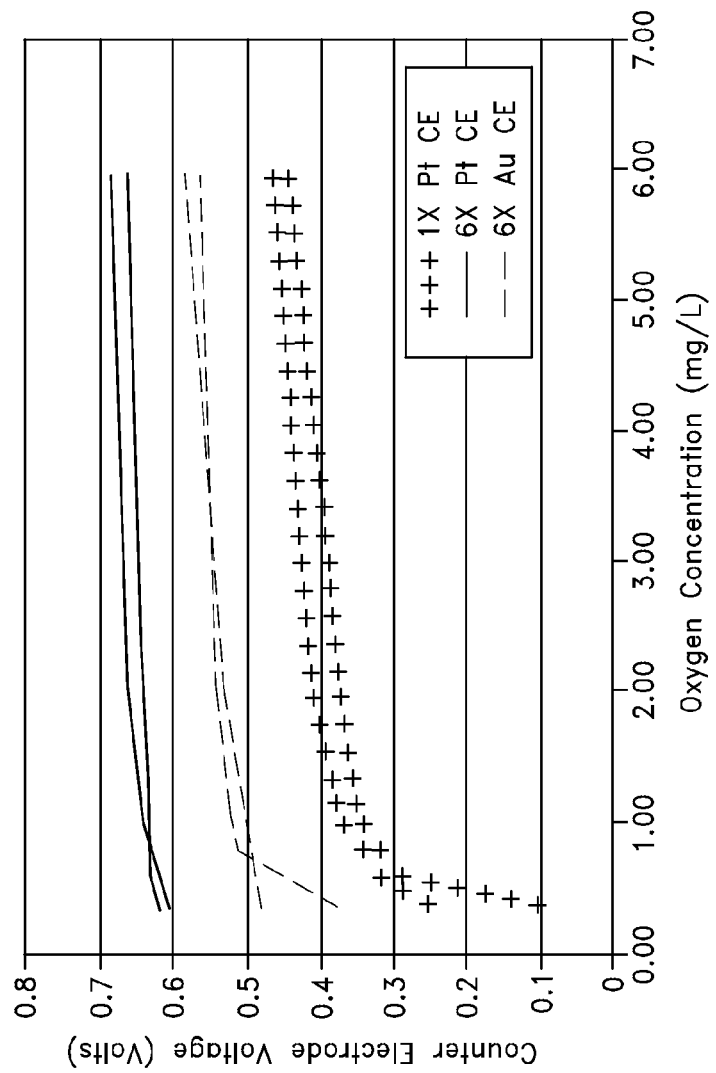
FIG. 9 Graphical representation of the counter electrode voltage as a function of oxygen concentration at 400 mg/dL glucose for sensor devices including the membrane shown in FIG. 8.

FIG. 9 graphically presents the counter electrode voltage as a function of oxygen concentration and 400 mg/dL glucose. This figure demonstrates that both the large Pt and Au counter electrode devices do not begin to reach the circuitry limits at low oxygen concentrations. Therefore, increased performance and accuracy can be obtained from a counter electrode that has an electrochemical reactive surface greater than the surface area of the working electrode.

The description and experimental materials presented above are intended to be illustrative of the present invention while not limiting the scope thereof. It will be apparent to those skilled in the art that variations and modifications can be made without departing from the spirit and scope of the present invention.

What is claimed is:

1. A continuous glucose sensor system comprising:
an implantable body comprising an electrode configured to measure a glucose concentration in a host, wherein the electrode is configured to generate a current output;
a membrane disposed over the electrode, the membrane comprising silicone and an enzyme configured to catalyze a reaction of glucose and oxygen from a biological fluid surrounding the membrane; and
sensor electronics operably connected to the electrode and configured to measure a current from the electrode;
wherein the continuous glucose sensor system is configured to maintain a 100% current output from the electrode in a fluid with an oxygen concentration of about 0.5 mg/L and a glucose concentration of 400 mg/dL, wherein the 100% current output corresponds to a current output of the system in a fluid with a glucose concentration of 400 mg/dL and an ambient oxygen concentration.

2. The continuous glucose sensor system of claim 1, wherein the membrane comprises a glucose blocking domain.

3. The continuous glucose sensor system of claim 1, wherein the electrode is a working electrode, and wherein the implantable body further comprises a reference electrode.

4. The continuous glucose sensor system of claim 1, wherein the membrane comprises polyurethane.

5. The continuous glucose sensor system of claim 1, wherein the membrane is configured to control a flux of oxygen and glucose therethrough.

6. The continuous glucose sensor system of claim 1, wherein the membrane is configured to reduce passage therethrough of interfering species.

7. The continuous glucose sensor system of claim 1, wherein a portion of the membrane is configured to limit diffusion of species that have a molecular weight greater than 34 kD.

8. The continuous glucose sensor system of claim 1, wherein the continuous glucose sensor system is configured to maintain a 100% current output in a fluid with an oxygen concentration of 0.5 mg/L and a glucose concentration of 400 mg/dL.

9. A continuous glucose sensor system comprising:
an implantable body comprising an electrode configured to measure a glucose concentration in a host, wherein the electrode is configured to generate a current output;
a membrane disposed over the electrode, the membrane comprising silicone and an enzyme configured to catalyze a reaction of glucose and oxygen from a biological fluid surrounding the membrane; and
sensor electronics operably connected to the electrode and configured to measure a current from the electrode;
wherein the continuous glucose sensor system is configured to maintain a 100% current output from the electrode in a fluid with a glucose concentration of 400 mg/dL when an oxygen concentration in the fluid is decreased from about 7 mg/L to an oxygen concentration of about 0.5 mg/L.

10. The continuous glucose sensor system of claim 9, wherein the 100% current output corresponds to the current output of the system in a fluid with a glucose concentration of 400 mg/dL and an ambient oxygen concentration.

11. A continuous glucose sensor system comprising:
an implantable body comprising an electrode configured to measure a glucose concentration in a host, wherein the electrode is configured to generate a current output;
a membrane disposed over the electrode, the membrane comprising a first domain that comprises silicone and a second domain that comprises an enzyme configured to catalyze a reaction of glucose and oxygen from a biological fluid surrounding the membrane, wherein the first domain has a thickness of about 0.032 inches or less; and
sensor electronics operably connected to the electrode and configured to measure a current from the electrode;
wherein the continuous glucose sensor system is configured to maintain a 100% signal current output from the electrode in a fluid with an oxygen concentration of about 0.5 mg/L and a glucose concentration of 400 mg/dL, wherein the 100% current output corresponds to a current output of the system in a fluid with a glucose concentration of 400 mg/dL and an ambient oxygen concentration.

12. The system of claim 11, wherein the first domain is configured to allow passage of glucose therethrough.

13. A continuous glucose sensor system comprising:
an implantable body comprising an electrode configured to measure a glucose concentration in a host, wherein the electrode is configured to generate a current output;
a membrane disposed over the electrode, the membrane comprising a first domain that comprises silicone and a second domain that comprises an enzyme configured to catalyze a reaction of glucose and oxygen from a biological fluid surrounding the membrane, wherein the first domain has a thickness of about 0.032 inches or less; and sensor electronics operably connected to the electrode and configured to measure a current from the electrode;

wherein the continuous glucose sensor system is configured to maintain a 100% current output from the electrode in a fluid with a glucose concentration of 400 mg/dL when an oxygen concentration in the fluid is decreased from an oxygen concentration of about 7 mg/L to an oxygen concentration of about 0.5 mg/L.

14. The continuous glucose sensor system of claim 13, wherein the 100% current output corresponds to a current output of the system in a fluid with a glucose concentration of 400 mg/dL and an ambient oxygen concentration.

15. The system of claim 13, wherein the first domain is configured to allow passage of glucose therethrough.

\* \* \* \* \*

UNITED STATES PATENT AND TRADEMARK OFFICE
CERTIFICATE OF CORRECTION

PATENT NO.           : 8,509,871 B2
APPLICATION NO.      : 12/260017
DATED                : August 13, 2013
INVENTOR(S)          : Rhodes et al.

Page 1 of 4

It is certified that error appears in the above-identified patent and that said Letters Patent is hereby corrected as shown below:

On the Title Page

In column 1 (page 9 item 56) at line 43, Under Other Publications, change "Membran," to --Membrane,--.

In column 2 (page 9 item 56) at line 29, Under Other Publications, change "Senso" to --Sensor--.

In column 2 (page 9 item 56) at line 32, Under Other Publications, change "heoglobin:" to --hemoglobin:--.

In column 2 (page 10 item 56) at line 3, Under Other Publications, change "Aniodic" to --Anodic--.

In column 1 (page 11 item 56) at line 62, Under Other Publications, change "Bromedical" to --Biomedical--.

In column 2 (page 11 item 56) at line 47, Under Other Publications, change "pancrease" to --pancreas--.

In column 2 (page 12 item 56) at line 54, Under Other Publications, change "hypoglycaemic" to --hypoglycemic--.

In column 2 (page 12 item 56) at line 61, Under Other Publications, change "reliablity" to --reliability--.

In column 2 (page 12 item 56) at line 62, Under Other Publications, change "Biollogy" to --Biology--.

In column 2 (page 12 item 56) at line 66, Under Other Publications, change "Hypoglycaemia" to --Hypoglycemia--.

In column 1 (page 13 item 56) at line 42, Under Other Publications, change "impleated" to --implanted--.

Signed and Sealed this
First Day of April, 2014

Michelle K. Lee
*Deputy Director of the United States Patent and Trademark Office*

CERTIFICATE OF CORRECTION (continued)
U.S. Pat. No. 8,509,871 B2

In column 2 (page 13 item 56) at line 48, Under Other Publications, change "artifical" to --artificial--.

In column 2 (page 13 item 56) at line 68, Under Other Publications, change "Thechnol." to --Technol.--.

In column 1 (page 14 item 56) at line 17, Under Other Publications, change "basedon" to --based--.

In column 1 (page 14 item 56) at line 43, Under Other Publications, change "Enzymlology," to --Enzymology,--.

In column 1 (page 14 item 56) at line 50, Under Other Publications, change "artifical" to --artificial--.

In column 1 (page 14 item 56) at line 60, Under Other Publications, change "your and your" to --you and your--.

In column 1 (page 14 item 56) at line 67, Under Other Publications, change "glocuse" to --glucose--.

In column 1 (page 14 item 56) at line 68, Under Other Publications, change "Diabetese" to --Diabetes--.

In column 2 (page 14 item 56) at line 5, Under Other Publications, change "Thechnol." to --Technol.--.

In column 2 (page 14 item 56) at line 10, Under Other Publications, change "Diabetese" to --Diabetes--.

In column 2 (page 14 item 56) at line 15, Under Other Publications, change "inactiviation" to --inactivation--.

In column 2 (page 14 item 56) at line 20, Under Other Publications, change "patents" to --patients--.

In column 2 (page 14 item 56) at line 49, Under Other Publications, change "activitiy," to --activity,--.

In column 2 (page 14 item 56) at line 58, Under Other Publications, change "Beioelectronics," to --Bioelectronics,--.

In column 2 (page 14 item 56) at line 59, Under Other Publications, change "glocuse" to --glucose--.

In column 2 (page 14 item 56) at line 68, Under Other Publications, change "valication" to --validation--.

In column 2 (page 14 item 56) at line 69, Under Other Publications, change "glucose-iunsulin interaaction in tyhpe 1" to --glucose-insulin interaction in type 1--.

In column 1 (page 15 item 56) at line 8, Under Other Publications, change "Electronanalysis" to --Electroanalysis--.

In column 1 (page 15 item 56) at line 12, Under Other Publications, change "artifical" to --artificial--.

In column 1 (page 15 item 56) at line 16, Under Other Publications, change "amperometeric" to --amperometric--.

In column 1 (page 15 item 56) at line 23, Under Other Publications, change "Thechnol." to --Technol.--.

In column 1 (page 15 item 56) at line 36, Under Other Publications, change "enzyme termistor" to --enzyme thermistor--.

In column 1 (page 15 item 56) at line 37, Under Other Publications, change "metobolites," to --metabolites,--.

In column 1 (page 15 item 56) at line 39, Under Other Publications, change "cholesteral and cholesteral" to --cholesterol and cholesterol--.

In column 1 (page 15 item 56) at line 41, Under Other Publications, change "Apllied" to --Applied--.

In column 2 (page 15 item 56) at line 9, Under Other Publications, change "Subcutaenous" to --Subcutaneous--.

In column 2 (page 15 item 56) at line 15, Under Other Publications, change "assitance" to --assistance--.

In column 2 (page 15 item 56) at line 16, Under Other Publications, change "Thechnol." to --Technol.--.

In column 2 (page 15 item 56) at line 31, Under Other Publications, change "Aced Sci U S A1998," to --Acad Sci U S A 1998,--.

In column 2 (page 15 item 56) at line 44, Under Other Publications, change "Thechnol." to --Technol.--.

In column 2 (page 15 item 56) at line 53, Under Other Publications, change "Membrance" to --Membrane--.

In column 2 (page 15 item 56) at line 55, Under Other Publications, change "cholesteral" to --cholesterol--.

In column 2 (page 15 item 56) at line 58, Under Other Publications, change "Deabetes" to --Diabetes--.

In column 2 (page 15 item 56) at line 65, Under Other Publications, change "Tranducers" to --Transducers--.

CERTIFICATE OF CORRECTION (continued)
U.S. Pat. No. 8,509,871 B2

In column 2 (page 16 item 56) at line 11, Under Other Publications, change "Polym" to --Polymer--.

In column 2 (page 16 item 56) at line 20, Under Other Publications, change "Tedh" to --Tech--.

In the Specification

In column 4 at line 64, change "by product," to --byproduct,--.

In column 12 at line 65, change "techniques" to --techniques.--.

In column 15 at line 14, change "larger that" to --larger than--.

In column 16 at line 17, change "(Carpenteria," to --(Carpinteria,--.

In the Claims

In column 20 at line 9, In Claim 7, change "claim 1," to --claim 6,--.

In column 20 at line 52, In Claim 11, change "100% signal" to --100%--.